(12) United States Patent
DeLeon et al.

(10) Patent No.: US 12,728,018 B2
(45) Date of Patent: Sep. 8, 2026

(54) ORTHOPAEDIC TRANSFER GUIDES AND METHODS OF REPAIR

(71) Applicant: ARTHREX, INC., Naples, FL (US)

(72) Inventors: Steven Jim DeLeon, San Antonio, TX (US); Nick Metcalfe, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 211 days.

(21) Appl. No.: 18/405,070

(22) Filed: Jan. 5, 2024

(65) Prior Publication Data

US 2024/0225858 A1 Jul. 11, 2024

Related U.S. Application Data

(60) Provisional application No. 63/478,700, filed on Jan. 6, 2023.

(51) Int. Cl.
*A61F 2/46* (2006.01)
*A61B 17/17* (2006.01)
(Continued)

(52) U.S. Cl.
CPC ........ *A61F 2/4612* (2013.01); *A61B 17/1778* (2016.11); *A61B 2017/564* (2013.01); *A61F 2002/30331* (2013.01); *A61F 2002/3054* (2013.01); *A61F 2002/30785* (2013.01); *A61F 2002/30892* (2013.01); *A61F 2002/4622* (2013.01); *A61F 2002/4627* (2013.01); *A61F 2002/4658* (2013.01)

(58) Field of Classification Search
CPC .......... A61B 2090/067; A61B 17/1778; A61B 17/8872; A61B 2017/0046; A61B 2017/00469; A61B 2017/564; A61F 2002/3054; A61F 2002/4658; A61F 2002/4627; A61F 2/4081; A61F 2/4612
See application file for complete search history.

(56) References Cited

U.S. PATENT DOCUMENTS 6,193,724 B1 2/2001 Chan
6,231,611 B1 5/2001 Mosseri
(Continued)

FOREIGN PATENT DOCUMENTS

EP 1273269 A2 1/2003
EP 3498227 A1 6/2019
(Continued)

OTHER PUBLICATIONS

International Preliminary Report on Patentability for International Application No. PCT/US2022/024795 mailed Nov. 9, 2023.
(Continued)

*Primary Examiner* — Samuel S Hanna
(74) *Attorney, Agent, or Firm* — Carlson, Gaskey & Olds, P.C.

(57) ABSTRACT

This disclosure relates to planning systems, assemblies and methods. The planning systems, assemblies and methods disclosed herein may be utilized for planning and implementing orthopaedic procedures to restore functionality to a joint, and may include one or more transfer members for positioning implants and other surgical devices relative to patient anatomy.

18 Claims, 35 Drawing Sheets

(51) Int. Cl.
*A61B 17/56* (2006.01)
*A61F 2/30* (2006.01)

(56) References Cited

U.S. PATENT DOCUMENTS 6,395,005 B1 5/2002 Lovell
7,931,690 B1 4/2011 Bonutti
8,303,665 B2 11/2012 Tornier et al.
8,361,076 B2 1/2013 Roose et al.
8,594,395 B2 11/2013 Roose et al.
8,632,597 B2 1/2014 Lappin
8,696,680 B2 4/2014 Iannotti et al.
8,702,717 B2 4/2014 Rauscher et al.
8,747,418 B2 6/2014 Qureshi et al.
8,801,725 B2 8/2014 Ritter et al.
8,852,283 B2 10/2014 Tornier et al.
8,926,627 B2 1/2015 Iannotti et al.
8,940,054 B2 1/2015 Wiley et al.
8,986,309 B1 3/2015 Murphy
8,992,538 B2 3/2015 Keefer
9,033,990 B2 5/2015 Iannotti et al.
9,114,017 B2 8/2015 Lappin
9,198,732 B2 12/2015 Iannotti et al.
9,226,830 B2 1/2016 De Wilde et al.
9,233,003 B2 1/2016 Roche et al.
9,283,083 B2 3/2016 Winslow et al.
9,345,497 B2 5/2016 Gonzalvez et al.
9,452,055 B2 9/2016 Lappin
9,480,580 B2 11/2016 White et al.
9,492,182 B2 11/2016 Keefer
9,526,514 B2 12/2016 Kelley et al.
9,532,880 B2 1/2017 Lappin
9,545,312 B2 1/2017 Tornier et al.
9,579,107 B2 2/2017 Schoenefeld
9,629,725 B2 4/2017 Gargac et al.
9,700,325 B2 7/2017 Schoenefeld
9,717,508 B2 8/2017 Iannotti et al.
9,741,263 B2 8/2017 Iannotti et al.
9,826,994 B2 11/2017 Eash et al.
9,844,440 B2 12/2017 Kovacs et al.
9,931,168 B2 4/2018 Brown et al.
10,028,803 B2 7/2018 O'Neill et al.
10,034,757 B2 7/2018 Kovacs et al.
10,130,378 B2 11/2018 Bryan
10,265,184 B2 4/2019 Lappin
10,271,858 B2 4/2019 Guilloux et al.
10,299,807 B2 5/2019 Murphy
10,357,373 B2 7/2019 Gargac et al.
10,357,378 B2 7/2019 Borries et al.
10,376,270 B2 8/2019 Eash
10,383,735 B2 8/2019 Wiley et al.
10,405,928 B2 9/2019 Falardeau et al.
10,426,624 B2 10/2019 Van Kampen et al.
10,433,983 B1 * 10/2019 Khosla .................. A61F 2/4612
10,617,434 B2 4/2020 Theiss et al.
10,813,774 B2 10/2020 Davenport et al.
10,828,111 B2 11/2020 Frank et al.
10,925,658 B2 2/2021 Hopkins
11,013,619 B2 5/2021 Cardon et al.
11,432,934 B2 9/2022 Couture et al.
2013/0245632 A1 9/2013 Iannotti et al.
2015/0105696 A1 4/2015 Litke et al.
2015/0140507 A1 5/2015 Moffson et al.
2015/0190151 A1 7/2015 Budhabhatti et al.
2015/0305891 A1 10/2015 Bergin et al.
2016/0184109 A1 6/2016 Davenport et al.
2016/0242933 A1 8/2016 Deransart et al.
2017/0000626 A1 1/2017 White et al.
2017/0079742 A1 3/2017 O'Neill et al.
2017/0095336 A1 4/2017 Tornier et al.
2017/0265873 A1 9/2017 Schoenefeld
2018/0049897 A1 2/2018 Lathers et al.
2018/0125509 A1 5/2018 Iannotti et al.
2018/0303618 A1 10/2018 Kovacs et al.
2018/0333263 A1 11/2018 Roby et al.
2018/0333268 A1 11/2018 Cardon et al.
2018/0360512 A1 12/2018 Mari
2019/0015116 A1 1/2019 Gargac et al.
2019/0015117 A1 1/2019 Neichel et al.
2019/0015118 A1 1/2019 Neichel et al.
2019/0015221 A1 1/2019 Neichel et al.
2019/0151106 A1 5/2019 Kovacs et al.
2019/0159848 A1 5/2019 Quaid et al.
2019/0159907 A1 5/2019 Roche et al.
2019/0240035 A1 8/2019 Lappin
2019/0298537 A1 10/2019 Gargac et al.
2019/0343658 A1 11/2019 Deransart et al.
2019/0380792 A1 12/2019 Poltaretskyi et al.
2020/0197185 A1 6/2020 Mahfouz
2021/0177441 A1 6/2021 Madier-Vigneux et al.
2022/0338933 A1 10/2022 Metcalfe et al.

FOREIGN PATENT DOCUMENTS

KR 102053599 B1 1/2020
WO 2012166888 A2 12/2012
WO 2013152182 A1 10/2013
WO 2014089291 A1 6/2014
WO 2017007565 A2 1/2017
WO 2017165346 A1 9/2017
WO 2018052965 A1 3/2018
WO 2018081073 A1 5/2018
WO 2019014278 A1 1/2019
WO 2020102886 A1 5/2020
WO 2021021247 A1 2/2021
WO 2022231853 A1 11/2022

OTHER PUBLICATIONS

International Search Report and Written Opinion for International Search Report PCT/US2022/038126 mailed Dec. 23, 2022.
International Search Report for International Application No. PCT/US2022/024795 mailed Sep. 19, 2022.
Musculoskeletal Key. Arthrex Univers Revers (TM) shoulder prosthesis. Retrieve from: https://musculoskeletalkey.com/arthrex-univers-revers-shoulder-prosthesis/.
International Search Report and Written Opinion for International Application No. PCT/US2024/010462 mailed Jun. 14, 2024.

* cited by examiner

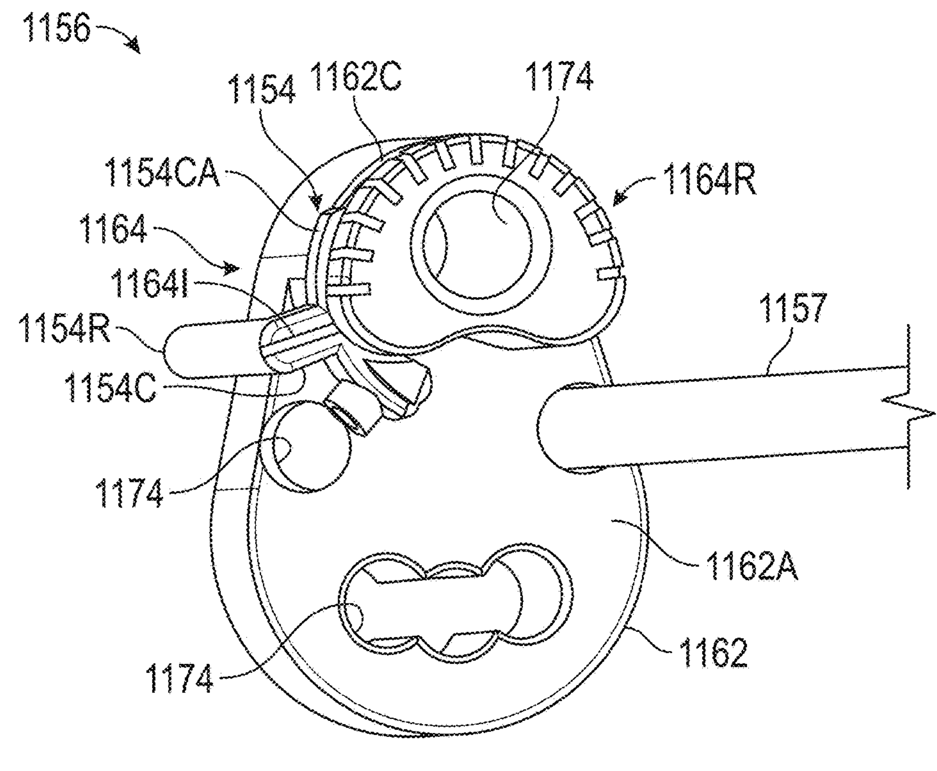
FIG. 41
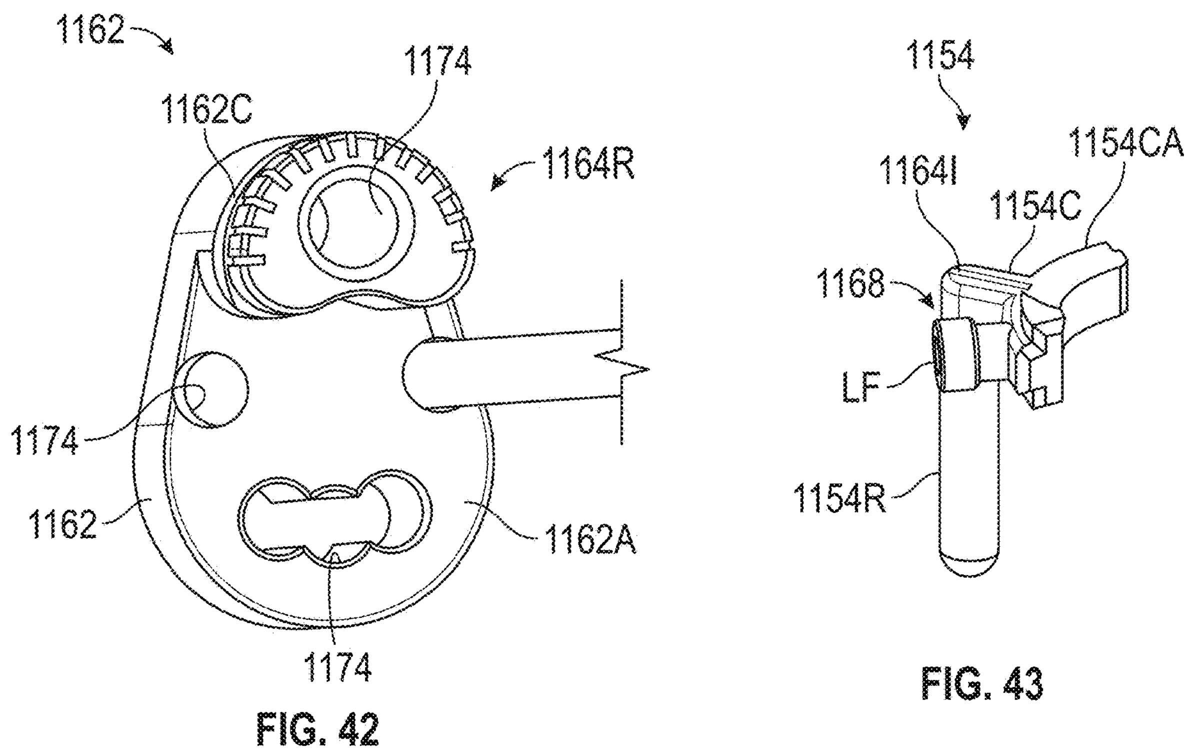
FIG. 42
FIG. 43

ORTHOPAEDIC TRANSFER GUIDES AND METHODS OF REPAIR

CROSS-REFERENCE TO RELATED APPLICATION

The present disclosure claims priority to U.S. Provisional Application No. 63/478,700 filed Jan. 6, 2023.

BACKGROUND

This disclosure relates to orthopaedic procedures and, more particularly, to systems and methods for planning and implementing the repair of bone defects and restoration of functionality to a joint, including positioning implants at a surgical site based on a surgical plan.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces. Some techniques utilize a bone graft and/or implant to repair a defect adjacent the articular surfaces. The surgeon may utilize a guide pin to position the implant.

SUMMARY

This disclosure relates to planning systems, assemblies and methods.

The planning systems, assemblies and methods disclosed herein may be utilized for planning and implementing orthopaedic procedures to restore functionality to a joint. Implants and various surgical devices may be positioned utilizing one or more transfer members associated with a surgical plan.

A transfer guide for an orthopaedic procedure of the present disclosure may include a guide body. At least one transfer member may be coupled to the guide body. The at least one transfer member may include a carrier and an outrigger which may extend from the carrier. The carrier may be rotatable about a periphery of the guide body to set a position of the outrigger. The outrigger may be configured to contact tissue to set an orientation of the guide body.

A kit for an orthopaedic procedure of the present disclosure may include at least one implant including a baseplate. The baseplate may include a main body and an anchor member that may extend outwardly from the main body. The anchor member may be securable to bone. A transfer guide may include a guide body including an interface securable to the main body. At least one transfer member may include a carrier and an outrigger that may extend from the carrier such that the outrigger may be spaced apart from a periphery of the at least one implant. The carrier may be rotatable about a periphery of the guide body to set a position of the outrigger. The outrigger may be configured to contact tissue to set an orientation of the baseplate relative to bone.

A transfer guide for an orthopaedic procedure according to the present disclosure may include a guide body extending along a guide axis between a front face and a rear face. The guide body may include at least one aperture dimensioned to receive a surgical device insertable in bone. The at least one transfer member may include a carrier and an outrigger that may extend from the carrier. The carrier may be moveable along a periphery of the guide body to set a position of the outrigger relative to the guide axis. The outrigger may be configured to contact tissue to set an orientation of the guide body.

A method of performing an orthopaedic procedure according to the present disclosure may include configuring a transfer guide. The transfer guide may include a guide body that may extend along a guide axis and a transfer member coupled to the guide body. The transfer member may include a carrier and an outrigger that may extend from the carrier. The configuring step may include rotating the carrier about a periphery of the guide body to set an orientation of the outrigger relative to the guide axis. The method may include positioning the transfer guide, which may include establishing contact between the outrigger and tissue to set an orientation of the transfer guide relative to a bone.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 41 illustrates a perspective view of portions of the transfer guide of FIG. 40 including a transfer member in a first position relative to a guide body.

FIG. 42 illustrates a perspective view of the guide body of FIG. 41.

FIG. 43 illustrates a perspective view of the transfer member of FIG. 41.

Like reference numbers and designations in the various drawings indicate like elements.

DETAILED DESCRIPTION

Figure 1:
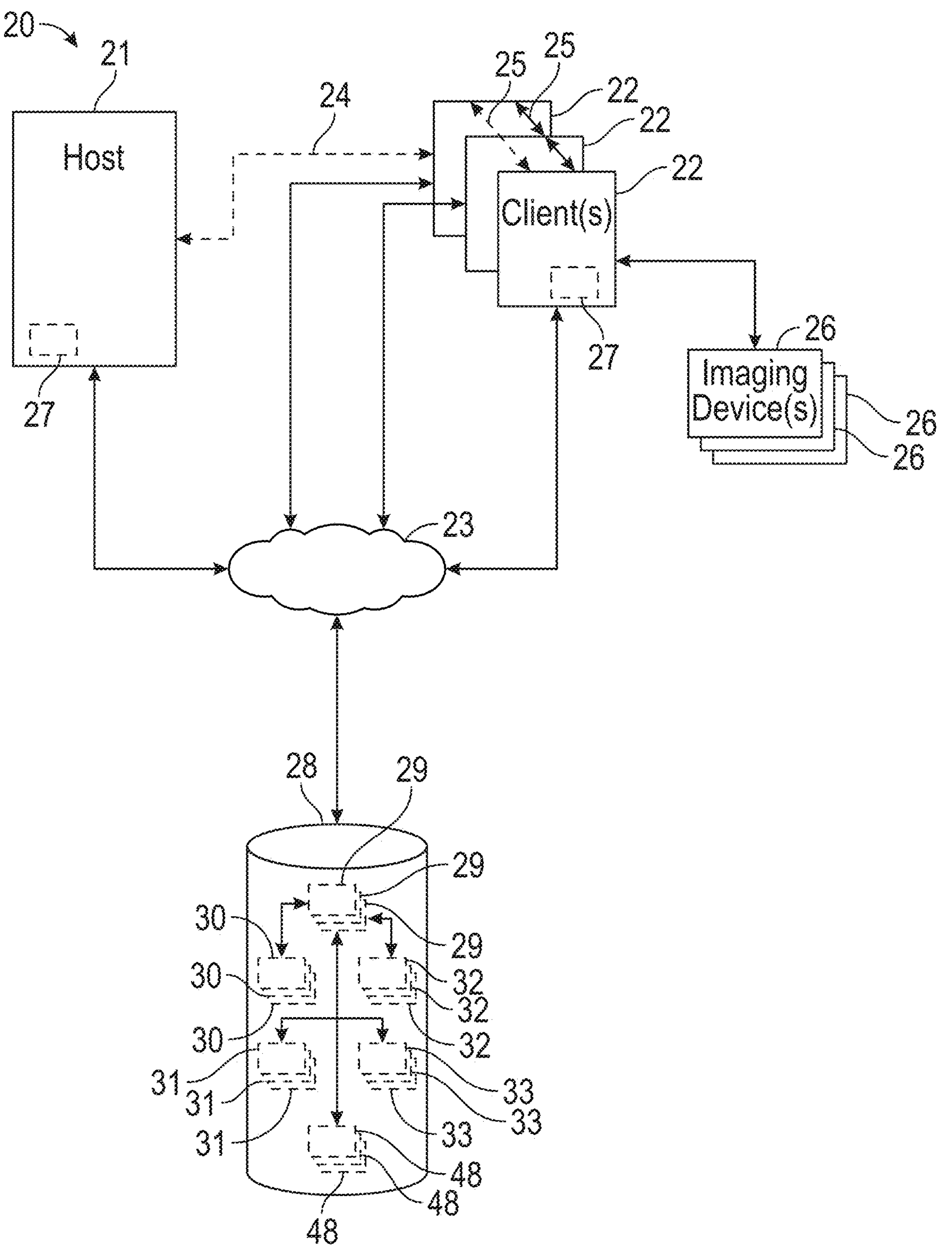
FIG. 1 illustrates an exemplary planning system.

This disclosure relates to surgical planning and implementation, including positioning implants relative to patient anatomy. The planning systems, assemblies and methods disclosed herein may be utilized for planning and implementing orthopaedic procedures to restore functionality to a joint. Implants and other surgical devices may be positioned utilizing one or more transfer members.

The transfer guides disclosed herein may be utilized to establish a rotational alignment (e.g., roll position) of various surgical devices, including orthopaedic implants and instruments situated relative to the patient anatomy. The transfer guide may include one or more transfer members. The transfer member may include a carrier and an outrigger (e.g., elongated leg). The carrier may be secured to a guide body of the transfer guide. The surgeon may configure a position of the outrigger relative to the guide body based on one or more parameters or settings specified in a preoperative plan. The outrigger may contact bone or other tissue at a respective contact point, which may be specified in the preoperative plan.

Utilizing the techniques disclosed herein, the surgeon may accurately transfer the rotational alignment of an orthopaedic implant from a preoperative plan to orthopaedic surgery with a calibratable surgical device.

The implant may be secured with one or more fasteners to the bone. The fasteners may be compression screws. Utilizing the techniques disclosed herein, a trajectory of the fastener may be established to improve fastener to bone contact (e.g., “screw purchase”). The trajectory of the fastener may be established to limit perforation of the fastener along an opposite side of the bone.

A rear face of the implant may include one or more regions that may be non-perpendicular to an axis of the implant. The implant may include a non-planar rear surface, which may have a patient-specific contour. The implant may include an augment portion to at least partially fill a void along an articular surface of a bone. The augment portion may establish the rear face of the implant. Utilizing the techniques disclosed herein, the implant may be positioned such that contact between the rear face of the implant and the bone may be improved, which may improve fixation and healing.

Transfer members may be associated with a predetermined surgical plan. One or more parameters of the surgical plan may be transferred to or by the transfer members for implementing a predetermined position of the respective implant and/or other surgical devices. The surgical plan may be tailored to the individual patient, which may improve healing. The surgeon or clinical assistant may configure or calibrate the transfer guide to set a (e.g., roll) position of the transfer member based on one or more parameters specified in the surgical plan. The transfer member may establish an angular stop to limit rotation of the transfer guide and associated implant and/or other surgical device relative to the patient anatomy. The transfer members may improve accuracy in positioning implants and other surgical devices according to surgical plans. The disclosed techniques may reduce complexity in implementing surgical plans, including reduced packaging and instrumentation. The transfer members may be single use and/or reusable, which may provide the surgeon flexibility in implementing surgical plans.

A transfer guide for an orthopaedic procedure of the present disclosure may include a guide body. At least one transfer member may be coupled to the guide body. The at least one transfer member may include a carrier and an outrigger which may extend from the carrier. The carrier may be rotatable about a periphery of the guide body to set a position of the outrigger. The outrigger may be configured to contact tissue to set an orientation of the guide body.

In implementations, the transfer guide may include an indicator and a ruler. The indicator may be moveable relative to the ruler to indicate a circumferential position of the outrigger relative to a guide axis of the guide body.

In implementations, the guide body may include an interface portion. The outrigger may be configured to set an orientation of a surgical device securable to the interface portion.

In implementations, the surgical device ma be an implant securable to a bone.

In implementations, the guide body may include an elongated guide shaft extending along a guide axis between a proximal end and a distal end; and In implementations the interface portion may be established adjacent the distal end of the guide shaft.

In implementations, the interface portion may include an array of protrusions circumferentially distributed about the guide axis. The array of protrusions may be dimensioned to mate with an array of insertion apertures of the implant to limit relative rotation between the guide shaft and the implant with respect to the guide axis.

In implementations, a coupling including a first coupling component and a second coupling component may be configured to mate with each other to capture a portion of the guide shaft. The carrier may be securable to the coupling.

In implementations, the coupling may be moveable along the guide axis to set an axial position of the outrigger relative to the guide axis.

In implementations, a groove may extend along one of the coupling and the guide shaft. A protrusion may extend along another one of the coupling and the guide shaft. The protrusion may be moveable along a length of the groove. The protrusion may be engageable with a wall bounding the groove to limit rotation of the coupling about the guide axis.

In implementations, a clamp may be releasably securable to the first coupling component to capture a portion of the carrier along a periphery of the first coupling component. The clamp may include a lock mechanism configured to set a position of the outrigger with respect to the guide axis.

In implementations, the carrier may include at least one aperture. The outrigger may be slidably received in the at least one aperture to set a position of the outrigger relative to the guide body.

In implementations, the at least one aperture may include a plurality of apertures distributed in a radial direction and/or circumferential direction relative to a guide axis of the guide body. The outrigger may be insertable in a selectable one of the plurality of apertures to set a position of the outrigger relative to the guide axis.

In implementations, the at least one transfer member may include a set of transfer members releasably securable to the guide body. The set of transfer members may be dimensioned such that a distribution of the plurality of apertures may differ for each transfer member of the set of transfer members.

In implementations, the guide body may include an elongated guide shaft extending along a guide axis. A coupling may include a first coupling component and a second coupling component that may be configured to mate with each other to capture a portion of the guide shaft. The carrier may be securable to the coupling.

In implementations, a clamp may be releasably securable to the first coupling component to capture a portion of the carrier of a selectable one of the transfer members along a periphery of the first coupling component. The clamp may include a lock mechanism configured to set a position of the outrigger with respect to the guide axis.

In implementations, the guide body may be dimensioned to contact an articular surface and/or a non-articular surface of a bone.

In implementations, the guide body may be rotatable about a guide element insertable in bone. The guide body may include one or more guide apertures dimensioned to receive a surgical instrument insertable in bone. The one or more guide apertures may be spaced apart from an axis of the guide element.

In implementations, the guide body may include an anchor member that may establish the guide element.

A kit for an orthopaedic procedure of the present disclosure may include at least one implant including a baseplate. The baseplate may include a main body and an anchor member that may extend outwardly from the main body. The anchor member may be securable to bone. A transfer guide may include a guide body including an interface securable to the main body. At least one transfer member may include a carrier and an outrigger that may extend from the carrier such that the outrigger may be spaced apart from a periphery of the at least one implant. The carrier may be rotatable about a periphery of the guide body to set a position of the outrigger. The outrigger may be configured to contact tissue to set an orientation of the baseplate relative to bone.

In implementations, the baseplate may include a plurality of peripheral apertures distributed about an axis of the main body. The outrigger may be configured to set a position of the peripheral apertures in response to contact with tissue.

In implementations, the implant may include an articulation member securable to the baseplate. The articulation member may include an articulation surface configured to engage an articular surface of an opposed bone or implant.

In implementations, the at least one transfer member may include a set of transfer members releasably securable to the guide body. The carrier of each transfer member of the set of transfer members may include a plurality of apertures. The outrigger may be insertable in a selectable one of the plurality of apertures to set a position of the outrigger relative to an axis of the guide body. The set of transfer members may be dimensioned such that a distribution of the plurality of apertures may differ for each transfer member of the set of transfer members.

A transfer guide for an orthopaedic procedure of the present disclosure may include a guide body extending along a guide axis between a front face and a rear face. The guide body may include at least one aperture dimensioned to receive a surgical device insertable in bone. The at least one transfer member may include a carrier and an outrigger that may extend from the carrier. The carrier may be moveable along a periphery of the guide body to set a position of the outrigger relative to the guide axis. The outrigger may be configured to contact tissue to set an orientation of the guide body.

In implementations, the rear face of the guide body may be dimensioned to contact an articular surface and/or a non-articular surface of a bone.

In implementations, the surgical device may be a drill configured to remove bone.

In implementations, the guide body may include a guide aperture along the guide axis. The guide body may be rotatable about a guide element receivable in the guide aperture and insertable in bone.

In implementations, the guide body may include a protrusion that may extend outwardly from the rear face along the guide axis. The protrusion may be configured to secure the guide body to bone. The guide body may be rotatable about the guide axis.

In implementations, the guide body may include an arcuate channel along the periphery of the guide body. The carrier may be movable along the arcuate channel to set the position of the outrigger relative to the guide axis.

In implementations, a lock mechanism may be configured to limit movement of the carrier along the arcuate channel.

A method of performing an orthopaedic procedure of the present disclosure may include configuring a transfer guide. The transfer guide may include a guide body that may extend along a guide axis and a transfer member coupled to the guide body. The transfer member may include a carrier and an outrigger that may extend from the carrier. The configuring step may include rotating the carrier about a periphery of the guide body to set an orientation of the outrigger relative to the guide axis. The method may include positioning the transfer guide, which may include establishing contact between the outrigger and tissue to set an orientation of the transfer guide relative to a bone.

In implementations, the configuring step may include moving the transfer member between a first position and a second position relative to the guide body based on at least one parameter of a preoperative plan.

In implementations, the method may include coupling the transfer guide and an implant to each other. The method may include positioning the implant in contact with the bone, which may include orienting the implant relative to the bone based on the orientation of the transfer guide.

In implementations, the implant may include a plurality of peripheral apertures which may be circumferentially distributed about an implant axis of the implant. The method may include positioning respective fasteners in the peripheral apertures and then into the bone to secure the implant which may occur subsequent to the step of positioning the implant.

In implementations, the transfer guide may include an array of protrusions that may be circumferentially distributed about the guide axis. The implant may include an array of insertion apertures that may be circumferentially distributed about the implant axis. The coupling step may include inserting the protrusions into respective ones of the insertion apertures at an interface to set the orientation of the implant relative to the transfer guide which may be based on at least one parameter of a preoperative plan.

In implementations, the carrier may include at least one aperture. The configuring step may include inserting the outrigger through the at least one aperture.

In implementations, the at least one aperture may include a plurality of apertures distributed in a radial direction and/or circumferential direction relative to the guide axis. The inserting step may include inserting the outrigger through a selected one of the plurality of apertures to set a position of the outrigger relative to the guide axis.

In implementations, the guide body may extend along the guide axis between a front face and a rear face. The guide body may include at least one aperture. The method may include positioning a surgical device through the at least one aperture, and then causing the surgical device to remove a portion of the bone.

In implementations, the guide body may include an arcuate channel along the periphery of the guide body. The configuring step may include moving the carrier along the arcuate channel to set the position of the outrigger relative to the guide axis.

The guide body may include a guide aperture. The method may include positioning a guide element through the guide aperture and into the bone. The step of positioning the transfer guide may include rotating the guide body about the guide element to establish the orientation of the transfer guide.

In implementations, the bone may be a portion of a glenoid.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans. The system 20 may be utilized for various orthopaedic and other surgical procedures, such as an arthroplasty to repair a joint. The system 20 may be utilized in the placement of an implant, such as an implant incorporated into a shoulder prosthesis. Although the planning systems and methods disclosed herein primarily refer to repair of a glenoid or humerus during an anatomic or reverse shoulder reconstruction, it should be understood that the planning system 20 may be utilized in the repair of other locations of the patient and other surgical procedures including repair of other bones and joints such as a wrist, hand, hip, knee or ankle and repair of fractures and other deformities.

The system 20 may include a host computer 21 and one or more client computers 22. The host computer 21 may be configured to execute one or more software programs. In some implementations, the host computer 21 may be more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may include UVPROM, EEPROM, FLASH, RAM, ROM, DVD, CD, a hard drive, or other computer readable medium which may store data and/or other information relating to the planning and implementation techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. In another implementation, the client computers 22 may be configured to communicate with each other directly via a peer-to-peer interface 25.

The system 20 may include, or may be coupled to, one or more imaging devices 26. Each client computer 22 may be coupled to one or more imaging devices 26. Each imaging device 26 may be configured to capture or acquire one or more images 30 of patient anatomy residing within a scan field (e.g., window) of the imaging device 26. The imaging device 26 may be configured to capture or acquire two dimensional (2D) and/or three dimensional (3D) greyscale and/or color images 30. Various imaging devices 26 may be utilized, such as an X-ray machine, computerized tomography (CT) machine or magnetic resonance imaging (MRI) machine that may be configured to obtain one or more images of a patient.

The client computers 22 may be configured to execute one or more software programs, such as various surgical tools. Each client computer 22 may be operable to access and locally and/or remotely execute a planning environment 27. The planning environment 27 may be a standalone software package or may be incorporated into another surgical tool. The planning environment 27 may be configured to communicate with the host computer 21 either over the network 23 or directly through the direct client interface 24.

The planning environment 27 may be configured to interact with one or more of the imaging devices 26 to capture or acquire images 30 of patient anatomy. The planning environment 27 may provide a display or visualization of one or more images 30, anatomical (e.g., bone) models 31, implant models 32 and/or transfer models 48 via one or more graphical user interfaces (GUI). Each image 30, bone model 31, implant model 32, transfer model 48 and other data and information may be stored in one or more files or records according to a specified data structure.

The system 20 may include at least one storage system 28, which may be operable to store or otherwise provide data to other computing devices. The storage system 28 may be a storage area network device (SAN) configured to communicate with the host computer 21 and/or the client computers 22 over the network 23. In implementations, the storage system 28 may be incorporated within or directly coupled to the host computer 21 and/or client computers 22. The storage system 28 may be configured to store one or more of computer software instructions, data, database files, configuration information, etc.

In some implementations, the system 20 may be a client-server architecture configured to execute computer software on the host computer 21, which may be accessible by the client computers 22 using either a thin client application or a web browser executing on the client computers 22. The host computer 21 may load the computer software instructions from local storage, or from the storage system 28, into memory and may execute the computer software using the one or more computer processors.

The system 20 may include one or more databases 29. The databases 29 may be stored at a central location, such as the storage system 28. In another implementation, one or more databases 29 may be stored at the host computer 21 and/or may be a distributed database provided by one or more of the client computers 22. Each database 29 may be a relational database configured to associate one or more images 30, bone models 31, implant models 32 and/or transfer models 48 to each other and/or a surgical plan 33. Each surgical plan 33 may be associated with the anatomy of a respective patient. Each image 30, bone model 31, implant model 32, transfer model 48 and surgical plan 33 may be assigned a unique identifier or database entry. The database 29 may be configured to store data and other information corresponding to the images 30, bone models 31, implant models 32, transfer models 48 and surgical plans 33 in one or more database records or entries, and/or may be configured to link or otherwise associate one or more files corresponding to each respective image 30, bone model 31, implant model 32, transfer model 48 and surgical plan 33. Images 30, bone models 31, implant models 32, transfer models 48 and associated surgical plans 33 stored in the database(s) 29 may correspond to respective patient anatomies from prior surgical cases, and may be arranged into one or more predefined categories such as sex, age, ethnicity, defect category, procedure type, surgeon, facility or organization, etc.

Each image 30 and bone model 31 may include data and other information obtained from one or more medical devices or tools, such as the imaging devices 26. The bone model 31 may include coordinate information relating to an anatomy of the patient obtained or derived from image(s) 30 captured or otherwise obtained by the imaging device(s) 26. Each implant model 32, transfer model 48 may include coordinate information associated with a predefined design or a design established or modified by the planning environment 27. The planning environment 27 may incorporate and/or interface with one or more modeling packages, such as a computer aided design (CAD) package, to render the models 31, 32, 48 as two-dimensional (2D) and/or three-dimensional (3D) volumes or constructs, which may overlay one or more of the images 30 in a display screen of a GUI.

The implant models 32 may correspond to implants and components of various shapes and sizes. Each implant may include one or more components that may be situated at a surgical site including screws, anchors and/or grafts. Each implant model 32 may correspond to a single component or may include two or more components that may be configured to establish an assembly. Each implant and associated component(s) may be formed of various materials, including metallic and/or non-metallic materials. Each bone model 31, implant model 32 and transfer model 48 may correspond to 2D and/or 3D geometry and may be utilized to generate a wireframe, mesh and/or solid construct in a display.

Each surgical plan 33 may be associated with one or more of the images 30, bone models 31, implant models 32 and/or transfer models 48. The surgical plan 33 may include various parameters associated with the images 30, bone models 31, implant models 32 and/or transfer models 48. In implementations, the surgical plan 33 may include parameters relating to bone density and bone quality associated with patient anatomy captured in the image(s) 30. The surgical plan 33 may include parameters including spatial information relating to relative positioning and coordinate information of the selected bone model(s) 30, implant model(s) 32 and/or transfer model(s) 48.

The surgical plan 33 may include one or more revisions to a bone model 31 and information relating to a position of an implant model 32 and/or transfer model 48 relative to the original and/or revised bone model 31. The surgical plan 33 may include coordinate information relating to the revised bone model 31 and a relative position of the implant model 32 and/or transfer model 48 in predefined data structure(s).

The planning environment 27 may be configured to make one or more revisions to a transfer model 48 automatically or in response to user interaction with the user interface. Revisions to each bone model 31, implant model 32, transfer model 48 and/or surgical plan 33 may be stored in the database 29 automatically and/or in response to user interaction with the system 20.

One or more surgeons and other users may be provided with a planning environment 27 via the client computers 22 and may simultaneously access each image 30, bone model 31, implant model 32, transfer model 48 and surgical plan 33 stored in the database(s) 29. Each user may interact with the planning environment 27 to create, view and/or modify various aspects of the surgical plan 33. Each client computer 22 may be configured to store local instances of the images 30, bone models 31, implant models 32, transfer models 48 and/or surgical plans 33, which may be synchronized in real-time or periodically with the database(s) 29. The planning environment 27 may be a standalone software package executed on a client computer 22 or may be provided as one or more services executed on the host computer 21, for example.

Figure 2:
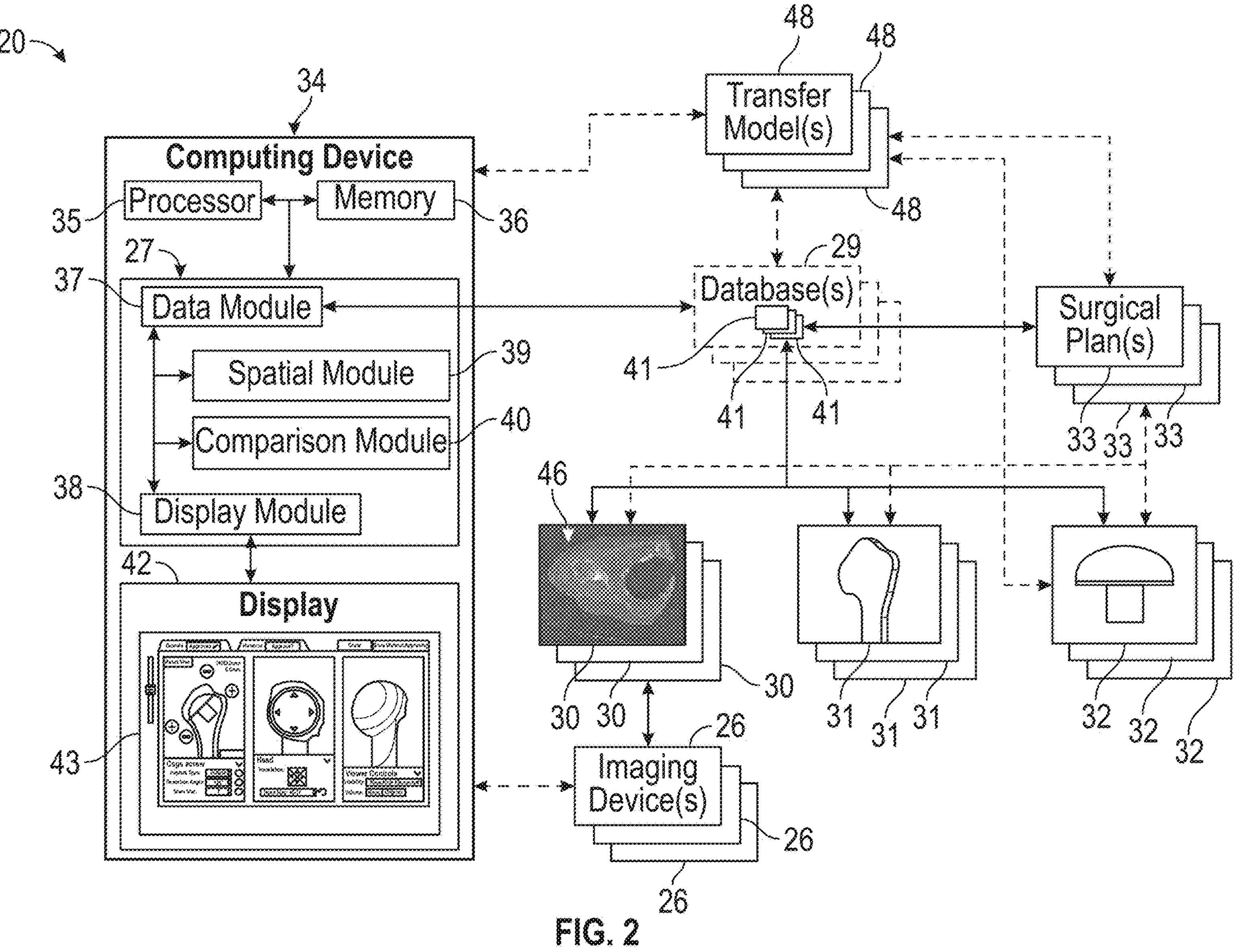
FIG. 2 illustrates aspects of the exemplary planning system of FIG. 1.

Referring to FIG. 2, with continuing reference to FIG. 1, the system 20 may include a computing device 34 including at least one processor 35 coupled to memory 36. The computing device 34 may include any of the computing devices disclosed herein, including the host computer 21 and/or client computer 22. The processor 35 may be configured to execute a planning environment 27 for creating, editing, executing and/or reviewing one or more surgical plans 33 and any associated bone models 31, implant models 32 and transfer models 48 during pre-operative, intra-operative and/or post-operative phases of a surgery.

The planning environment 27 may include at least a data module 37, a display module 38, a spatial module 39 and a comparison module 40. Although four modules are shown, it should be understood that fewer or more than four modules may be utilized and/or one or more of the modules may be combined to provide the disclosed functionality.

The data module 37 may be configured to access, retrieve and/or store data and other information in the database(s) 29 corresponding to one or more images 30 of patient anatomy, bone model(s) 31, implant model(s) 32, transfer model(s) 48 and/or surgical plan(s) 33. The data and other information may be stored in one or more databases 29 as one or more records or entries 41. In some implementations, the data and other information may be stored in one or more files that are accessible by referencing one or more objects or memory locations referenced by the records 41.

The memory 36 may be configured to access, load, edit and/or store instances of one or more images 30, bone models 31, implant models 32, transfer models 48 and/or surgical plans 33 in response to one or more commands from the data module 37. The data module 37 may be configured to cause the memory 36 to store a local instance of the image(s) 30, bone model(s) 31, implant model(s) 32, transfer model(s) 48 and/or surgical plan(s) 33, which may be synchronized with the records 41 in the database(s) 29.

The data module 37 may be configured to receive data and other information corresponding to at least one or more images 30 of patient anatomy from various sources such as the imaging device(s) 26. The data module 37 may be configured to command the imaging device 26 to capture or acquire the images 30 automatically or in response to user interaction.

The display module 38 may be configured to display data and other information relating to one or more surgical plans 33 in at least one graphical user interface (GUI) 43, including one or more of the images 30, bone models 31, implant models 32 and/or transfer models 48. The computing device 34 may incorporate or be coupled to a display device 42. The display module 38 may be configured to cause the display device 42 to display information in the user interface 43. A surgeon or other user may interact with the user interface 43 via the planning environment 27 to view one or more images 30 of patient anatomy 46 and/or any associated bone models 31, implant models 32 and transfer models 48. The surgeon or other user may interact with the user interface 43 via the planning environment 27 to create, edit, execute and/or review one or more surgical plans 33.

Figure 3A:
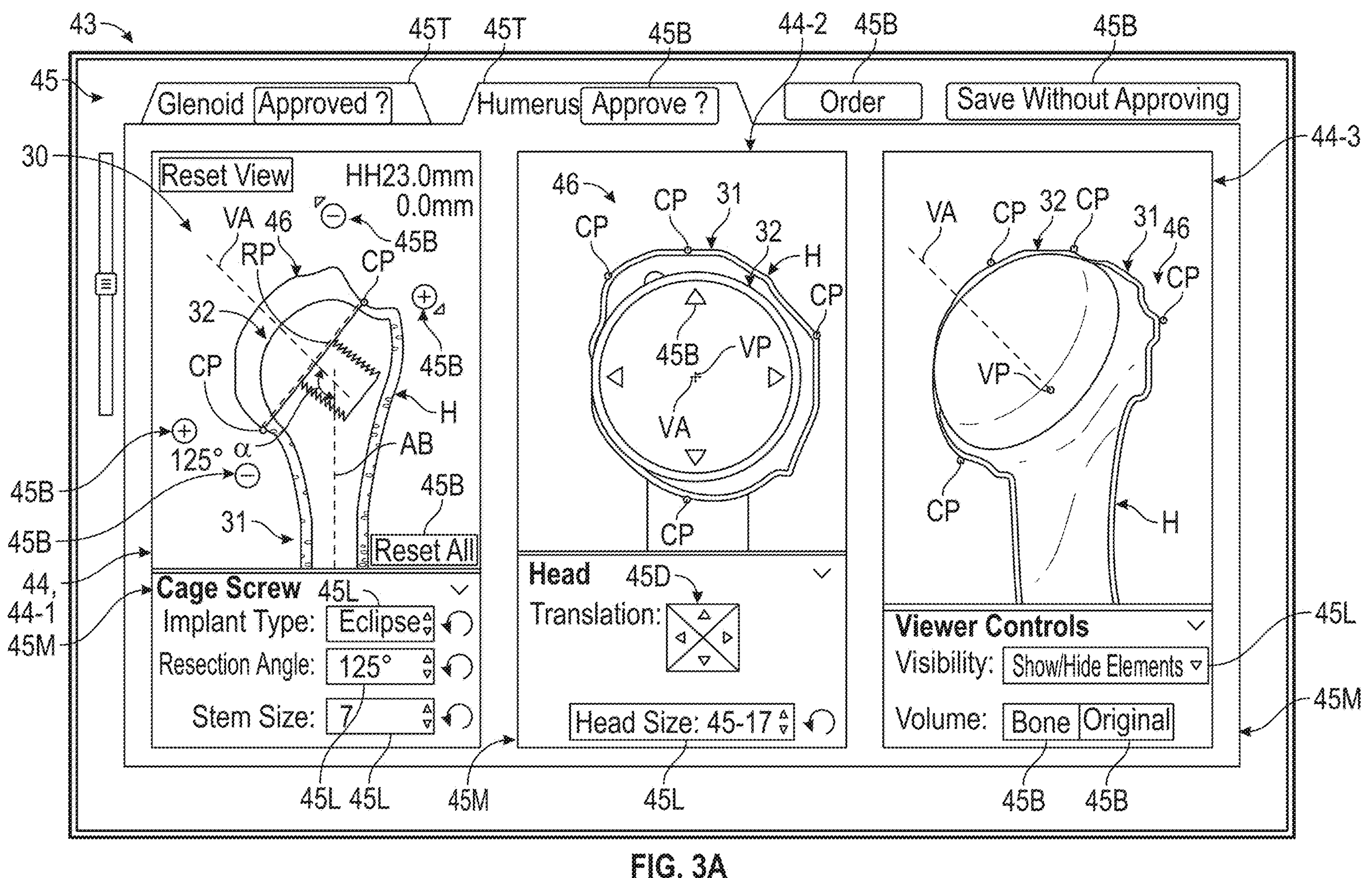
FIG. 3A illustrates an implementation of a user interface of the planning system of FIG. 2.
Figure 3B:
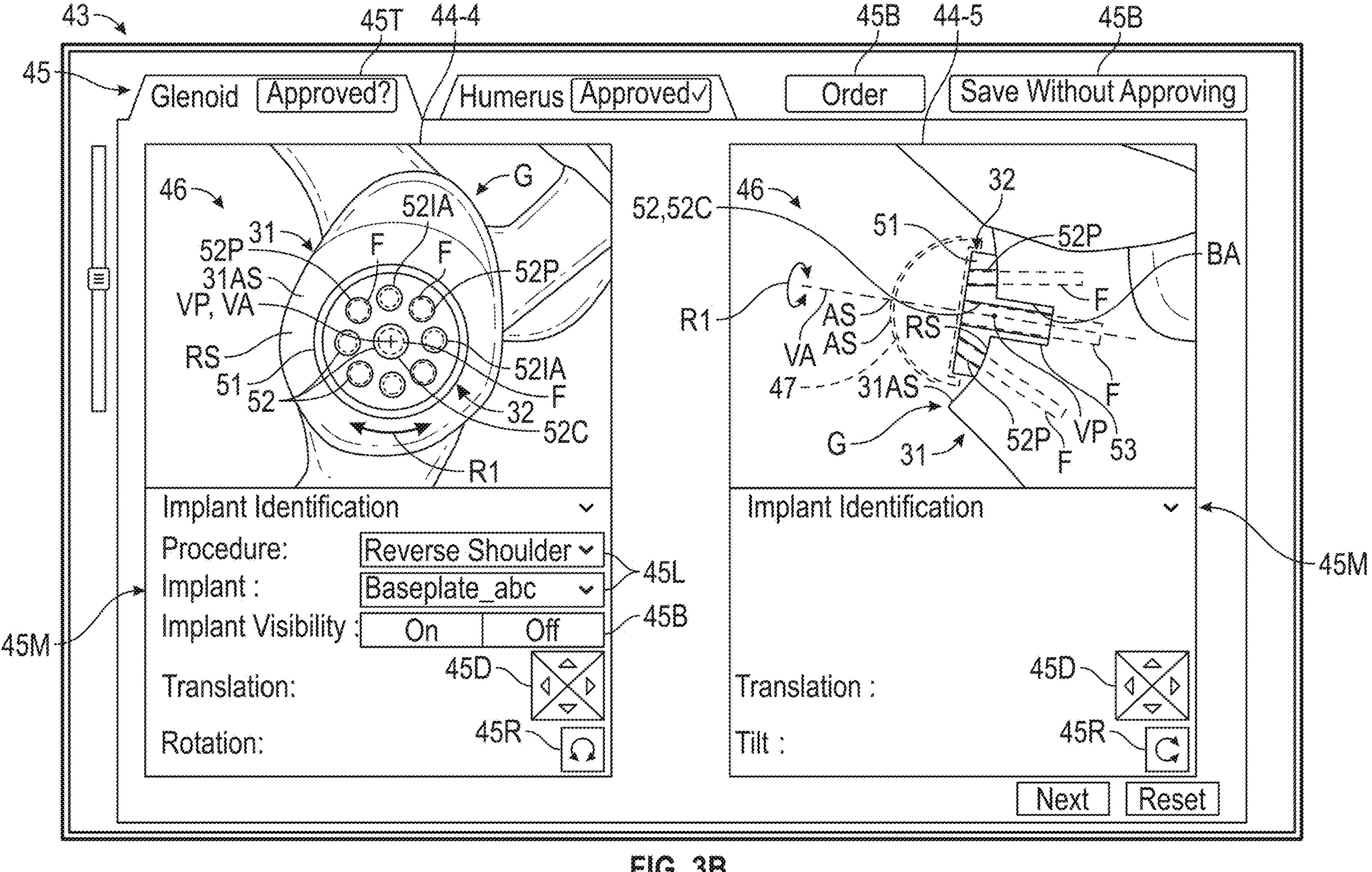
FIG. 3B illustrates another implementation of a user interface of the planning system of FIG. 2.
Figure 3C:
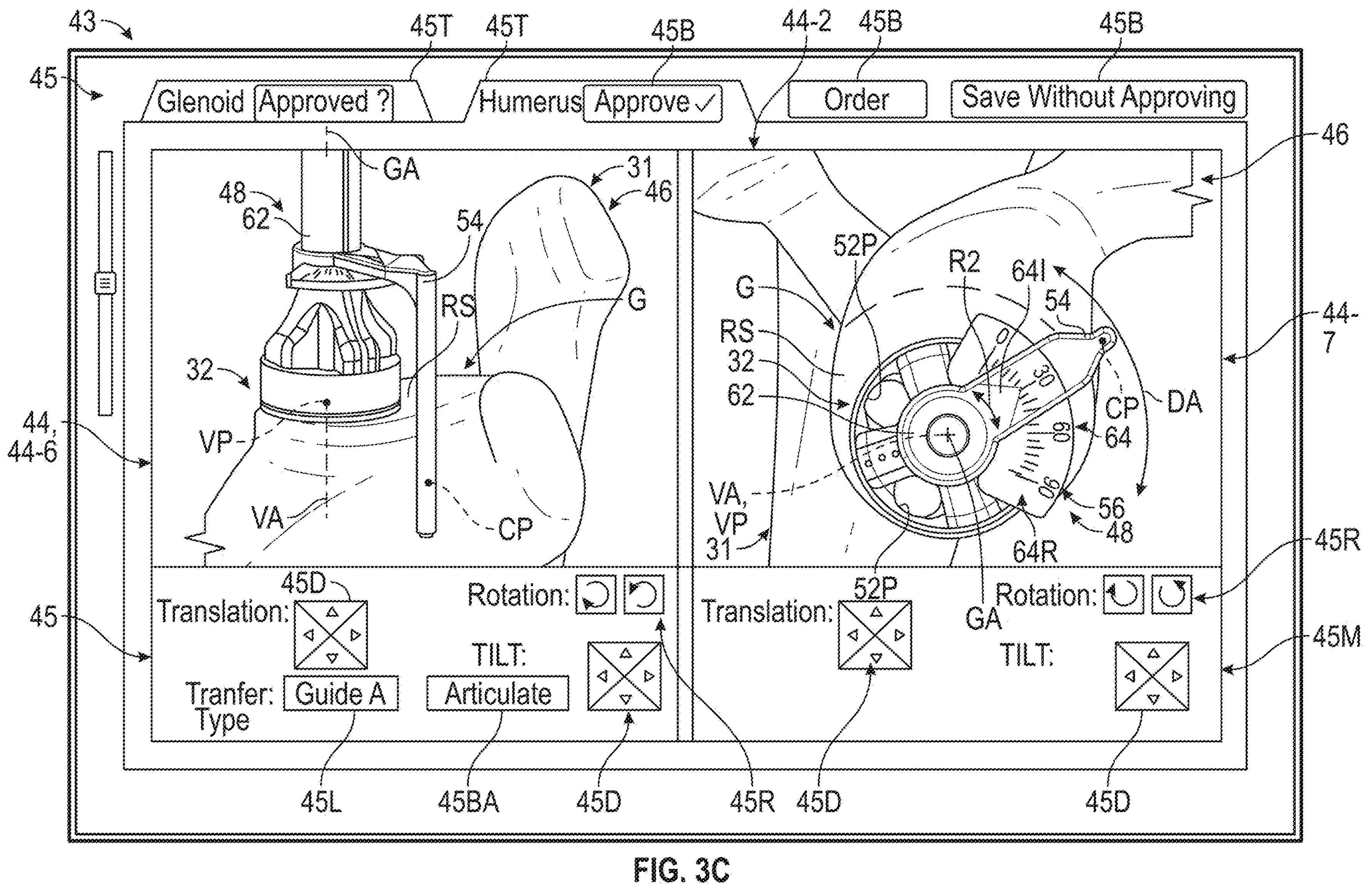
FIG. 3C illustrates another implementation of a user interface of the planning system of FIG. 2.

Referring to FIG. 3A-3C, with continuing reference to FIG. 2, the user interface 43 may include one or more display windows 44 and one or more objects 45. The display windows 44 may include first, second and third display windows 44-1, 44-2, 44-3 (FIG. 3A), may include fourth and fifth display windows 44-4, 44-5 (FIG. 3B), and may include sixth and seventh display windows 44-6, 44-7 (FIG. 3C). Although seven display windows 44 are shown, it should be understood that fewer or more than seven display windows 44 may be utilized in accordance with the teachings disclosed herein.

A surgeon or clinical user may interact with the user interface 43 including the objects 45 and/or display windows 44 to retrieve, view, edit, store, etc. various aspects of a surgical plan 33, such as the selected image(s) 30, bone model(s) 31, implant model(s) 32 and/or transfer model(s) 48. The objects 45 may include graphics such as menus, tabs and buttons accessible by user interaction, such as tabs 45T, buttons 45B, drop-down lists 45L, and directional indicators 45D. The objects 45 may be organized in one or more menu items 45M associated with the respective display windows 44. Geometric objects, including selected image(s) 30, bone model(s) 31, implant model(s) 32, transfer model(s) 48 and/or other information relating to the surgical plan 33, may be displayed in one or more of the display windows 44.

Each transfer model 48 may include at least one transfer member 54, which may be associated with a transfer guide 56 (see, e.g., windows 44-6, 44-7). The transfer model 48 may be secured to, or otherwise positioned in contact with, a respective implant model 32. The transfer model 48 may be configured to set an orientation of the implant model 32 relative to the bone model 31. In implementations, the transfer model 48 may be seated against the bone model 31.

The surgeon may interact with the objects 45 to specify various aspects of a surgical plan 33. In implementations, the surgeon may select one of the tabs 45T to view or specify aspects of the surgical plan 33 for one portion of a joint, such as a glenoid G (see, e.g., FIGS. 3B-3C), and may select another one of the tabs 45T to view or specify aspects of the surgical plan 33 for another portion of the joint, such as a humerus H (see, e.g., FIG. 3A).

The surgeon may interact with the menu items 45M to select and specify various aspects of the bone models 31, implant models 32 and/or transfer models 48 from the database 29. In the implementation of FIG. 3A, the display module 38 may be configured to display one or more bone models 31 together with the respective image(s) 30 of the patient anatomy 46 and implant models 32 selected in response to user interaction with the user interface 43. The user may interact with the drop-down lists 45L associated with the first display window 44-1 to specify implant type, resection angle and implant size. The resection angle menu item may be associated with a resection plane RP (shown in dashed lines in window 44-1).

The user may interact with buttons 45B to change (e.g., increase or decrease) the resection angle. The user may interact with buttons 45B adjacent the selected implant model 32 to change (e.g., increase or decrease) a size of a component of the selected implant model 32. The buttons 45B may be overlaid onto or may be situated adjacent to the display windows 44. The user may interact with the directional indicator 45D to move a portion of the selected implant model 32 in different directions (e.g., up, down, left, right) in the second display window 44-2. The surgeon may drag or otherwise move the selected implant model 32 to a desired position in the second display window 44-2 utilizing a mouse or other input device. The surgeon may interact with one of the drop-down lists 45L to specify a type and/or size of a component of the selected implant model 32.

The display module 38 may be configured to superimpose one or more of the bone models 31, and implant models 32 over one or more of the images 30 (see, e.g., window 44-1). The implant models 32 may be associated with implants of various configurations, shapes, sizes, procedures, instrumentation, etc. The implant model 32 may include one or more components that establish an assembly. Exemplary implants may include baseplates coupled to a respective articulation member, bone plates configured to interconnect adjacent bones or bone fragments, intermedullary nails, suture anchors, etc. The articulation member may have an articular surface dimensioned to mate with an articular surface of an opposed bone or implant. At least a portion of the implant model 32 may be configured to be at least partially received in a volume of a selected one of the bone models 31. The implant model 32 may have an articulation surface dimensioned to mate with an articular surface of an opposed bone or implant.

The display windows 44 may be configured to display the images 30, bone models 31, implant models 32 and/or transfer model(s) 48 at various orientations. The display module 38 may be configured to display two dimensional (2D) representation(s) of the selected bone model(s) 31, implant model(s) 32 and/or transfer model(s) 48 in the first and/or second display windows 44-1, 44-2, and may be configured to display 3D representation(s) of the selected bone model 31, implant model 32 and/or transfer model(s) 48 in the third display window 44-3. The surgeon may interact with the user interface 43 to move the selected bone model 31, selected implant model 32 and/or selected transfer model 48 in 2D space (e.g., up, down, left, right) and/or 3D space. In other implementations, the display module 38 may be configured to display a 2D representation of the selected bone model(s) 31, selected implant model(s) 32 in the third display window 44-3.

The display module 38 may be configured such that the selected image(s) 30, bone model(s) 31, implant model(s) 32 and/or transfer model(s) 48 may be selectively displayed and hidden (e.g., toggled) in one or more of the display windows 44 in response to user interaction with the user interface 43, which may provide the surgeon with enhanced flexibility in reviewing aspects of the surgical plan 33. The surgeon may interact with the drop-down lists 45L to selectively display and hide components of the selected implant model 32 in the third display window 44-3.

The selected bone model 31 may correspond to a bone associated with a joint, including any of the exemplary joints disclosed herein, such as a humerus H (see, e.g., FIG. 3A). The display module 38 may be configured to display a sectional view of the selected bone model 31 and selected implant model 32 in the first viewing window 44-1. The sectional view of the bone model(s) 31 may be presented or displayed together with the associated image(s) 30 of the patient anatomy 46.

The spatial module 39 may be configured to establish the resection plane RP along the selected bone model 31. A volume of the selected implant model 32 may be at least partially received in a volume of the selected bone model 31 along the resection plane RP. The resection plane RP may be defined by a resection angle α.

In the implementation of FIG. 3B, the spatial module 39 may be configured to define a resection surface RS along the selected bone model 31. The resection surface RS may be defined utilizing any of the techniques disclosed herein. In implementations, the resection surface RS may be defined automatically by the spatial module 39 in response to selection of the bone model 31 and/or implant model 32. In implementations, the surgeon or user may interact with one or more of the objects 45, directly with the display window 44 and/or another portion of the user interface 43 to define the resection surface RS. The resection surface RS may have various geometries, such as a substantially planar or concave geometry, or a complex geometry. A volume of the selected implant model 32 may be at least partially received in a volume of the selected bone model 31 along the resection surface RS (see, e.g., display window 44-5). In implementations, the implant model 32 may be positioned along a surface contour of the selected bone model 31.

The spatial module 39 may be configured to cause the display module 38 to display an excised portion of the selected bone model 31 to be displayed in the first display window 44-1 in a different manner than a remainder of the bone model 31 on an opposed side of the resection plane RP. For example, the excised portion of the bone model 31 may be hidden from display in the first display window 44-1 such that the respective portion of the image 30 of the patient anatomy 46 is shown (see, e.g., FIG. 3A. In other implementations, the excised portion of the selected bone model 31 may be displayed in a relatively darker shade. The spatial module 39 may determine the excised portion by comparing coordinates of the bone model 31 with respect to a position of the resection plane RP. The user may interact with one or more buttons 45B to toggle between a volume of previous and revised (e.g., resected) states of the selected bone model 31.

The planning environment 27 may be configured such that changes in one of the display windows 44 are synchronized with each of the other respective window(s) 44. The changes may be synchronized between the display windows 44 automatically and/or manually in response to user interaction.

Referring to FIG. 3B, with continuing reference to FIG. 2, the spatial module 39 may be configured to position the selected implant model(s) 32 into contact with the bone model(s) 31 at a specified or defined position and orientation automatically and/or in response to user input. The surgeon, assistant or other user may interact with the menu 45M or another portion of the user interface 43 to position and/or orient the implant model 32 relative to the bone model 31. The surgeon, assistant or other user may interact with the menu 45M or another portion of the user interface 43 to adjust a position and/or orientation of the implant model 32 relative to the bone model 31.

The implant model 32 may be positioned relative to a surface of the bone model 31, such as an articulation surface 31AS which may be associated with an articular surface of a bone. The user may interact with the menus 45M, directly with the display windows 44-4, 44-5, or with another portion of the user interface 43 to position and orient the selected implant model 32 relative to the bone model 31, including a virtual axis VA of the implant model 32. The user may interact with the menu 45M, the display windows 44-4, 44-5 or another portion of the user interface 43 to move the selected bone model 31 and/or selected implant model 32 in 2D space (e.g., up, down, left, right) and/or 3D space (e.g., rotation, tilt, zoom, etc.), which may occur in response to interaction with directional indicators 45D, 45R. The implant model 32 may be movable in a first rotational direction R1 about the virtual axis VA automatically and/or in response to user interaction with the user interface 43 to set an orientation of the implant model 32 relative to the patient anatomy 46.

The implant model 32 may include a baseplate 51 securable to bone. The baseplate 51 may include a main (e.g., plate) body and an alignment member (e.g., anchor or stem) 53. The alignment member 53 may be insertable in bone. The baseplate 51 may include one or more apertures 52. The apertures 52 may include a central aperture 52C, an array of peripheral apertures 52P and/or an array of interface apertures 52IA. The peripheral apertures 52P and/or interface apertures 52IA may be circumferentially distributed about the virtual (e.g., plate) axis VA. The central aperture 52C may be established along the virtual axis VA. The baseplate 51 may be securable to an articulation member 47 (shown in dashed lines). The articulation member 47 may be configured to engage an articular surface AS of an opposed bone or implant (shown in dashed lines). The interface apertures 52IA may be configured to engage one or more features of the selected transfer model 48.

The display module 38 may be configured to display one or more fastener models F (shown in dashed lines). The fastener models F may be associated with respective fasteners configured to secure an implant associated with a selected implant model 32.

The surgeon may utilize various instrumentation and devices to implement each surgical plan 33, including preparing the surgical site and securing one or more implants to bone or other tissue to restore functionality to the respective joint. Each of the transfer models 48 may be associated with a respective instrument or device (e.g., transfer guide) or a respective implant model 32.

The surgical plan 33 may be associated with one or more positioning objects such as a guide element (e.g., guide pin, guide wire or Kirschner wire) dimensioned to be secured in tissue to position and orient the various instrumentation, devices and/or implants. The display module 38 may be configured to display a virtual position VP and virtual axis VA in one or more of the display windows 44. The virtual position VP may be associated with a specified position of the positioning object relative to the patient anatomy 46. In implementations, a portion of the implant model 32 and/or transfer model 48 may serve as a positioning object (see, e.g., FIG. 3C). The positioning object may be associated with an anchor member (e.g., elongated stem) receivable in bone to secure the respective implant (see, e.g., FIG. 3B).

The virtual axis VA may extend through the virtual position VP and may be associated with a specified orientation of the positioning object relative to the patient anatomy 46. The spatial module 39 may be configured to set the virtual position VP and/or virtual axis VA in response to placement of a respective implant model 32 relative to the bone model 31 and associated patient anatomy 46. The virtual position VP and/or virtual axis VA may be set and/or adjusted automatically based on a position and orientation of the selected implant model 32 relative to the selected bone model 31 and/or in response to user interaction with the user interface 43.

Referring to FIGS. 3A and 3C, with continuing reference to FIG. 2, the spatial module 39 may be configured to determine one or more contact points CP associated with the patient anatomy 46. The contact points CP may be associated with one or more landmarks or other surface features along the bone model 31 and/or other portions of the patient anatomy 46. Each contact point CP may be established along an articular surface or non-articular surface of a bone. The spatial module 39 may be configured to set the contact points CP based on the virtual position VP, virtual axis VA and/or position and orientation of the respective implant model 32 relative to the patient anatomy 46. The spatial module 39 may be configured to cause the display module 38 to display the contact points CP in one or more of the display windows 44. In implementations, the contact points CP may be set and/or adjusted automatically based on a position of the implant model 32 and/or in response to user interaction with the user interface 43. The virtual position VP, virtual axis VA and/or contact points CP may be stored in one or more records 41 in the database 29 and may be associated with the respective surgical plan 33.

Referring to FIG. 3C, with continuing reference to FIGS. 2 and 3A-3B, the comparison module 40 may be configured to generate or set one or more parameters associated with implementing the surgical plan 33. The parameters may include one or more settings or dimensions associated with the respective transfer model 48. The parameters may be based on the virtual position VP, virtual axis VA and/or contact points CP. The comparison module 40 may be configured to determine one or more settings or dimensions associated with the respective transfer model 48 relative to the patient anatomy 46, bone model(s) 31, implant model(s) 46, virtual position VP, virtual axis VA and/or contact points CP. The dimensions and settings may be utilized to configure a physical instance of each respective transfer model 48. The settings may be utilized to specify a position and orientation of each respective transfer model 48 relative to the implant model 32 and/or bone model 31. The settings may be utilized to configure one or more transfer members (e.g., objects) and related instrumentation or devices associated with the transfer model 48. The comparison module 40 may be configured to generate the settings and/or dimensions such that the transfer model 48 contacts one or more predetermined positions along the bone model 31 or patient anatomy 46 in an installed position when coupled or otherwise positioned relative to the respective implant model 32. The predetermined positions may include one or more of the contact points CP. The settings and dimensions may be communicated utilizing various techniques, including one or more graphics in the user interface 43 or output files. The settings and/or dimensions may be stored in one or more records 41 in the database 29 associated with the transfer models 48.

The user may interact with a list 45L associated with the display window 44-6 to select a transfer model 48 from the database 29. The display model 38 may be configured to display the selected transfer model 48 in the windows 44-6 and/or 44-7 at various positions and orientations. The spatial module 39 may be configured to set an initial position of the selected transfer model 48 according to the virtual position VP, virtual axis VA and/or contact points CP.

The user may interact with the user interface 43 to set or adjust a position and/or orientation of the selected transfer model 48. The user may interact with directional indicators 45D to move the selected transfer model 48 and/or virtual position VP in different directions (e.g., up, down, left, right) in the display windows 44-6, 44-7. The surgeon may drag or otherwise move the selected transfer model 48 and/or virtual position VP to a desired position in the windows 44-6, 44-7 utilizing a mouse or other input device. The user may interact with rotational indicators 45R to adjust a position and/or orientation of the transfer model 48 about the virtual axis VA relative to the selected bone model 31 and/or implant model 32. The user may interact with directional (e.g., tilt) indicators 45D to adjust an orientation of the selected transfer model 48 and associated virtual axis VA at the virtual position VP relative to the selected bone model 31 and/or implant model 32. The user may interact with an articulation button 45BA and/or directional indicator DA (e.g., window 44-7) to cause the transfer member 54 to articulate or otherwise move to relative to a guide body 62 of the transfer guide 56. The guide body 62 may extend along a guide axis GA. The guide axis GA may substantially coincide with or may otherwise parallel to the virtual axis VA of the respective implant model 32. For the purposes of this disclosure, the terms "approximately," "about" and "substantially" mean±10% of the stated value or relationship unless otherwise indicated.

Each transfer member 54 may be articulated or otherwise moved manually in response to user interaction and/or automatically in response to situating the transfer member 54 relative to the bone model 31 and/or implant model 32. Articulation or movement of the transfer member 54 may occur such that the transfer member 54 may contact a surface of the bone model 31. Movement of the transfer member 54 may cause an adjustment to the respective contact points CP.

The transfer model 48 may include an alignment mechanism 64. The alignment mechanism 64 may configured to indicate a circumferential position of the transfer member 54 relative to the guide axis GA. The alignment mechanism 64 may include an indicator 64I and a ruler 64R. The ruler 64R may include indicia in discrete increments. In implementations, the indicia may be associated with respective circumferential positions of the transfer member 54 relative to the guide axis GA. The indicia may include increments of approximately 5 degrees associated with circumferential positions about the guide axis GA, although increments of greater or less than 5 degrees may be utilized. The increments along the ruler 64R may be less than a circumferential spacing between directly adjacent pairs of the peripheral apertures 52P with respect to the virtual axis VA.

The indicator 64I may be aligned with a selected position along the ruler 64R. The indicator 64I may be movable relative to the ruler 64R to indicate a circumferential position of the transfer member 54 relative to the guide axis GA of the guide body 62. The indicator 64I may be rotatable or otherwise moveable in a second rotational direction R2 relative to the guide axis GA to set a position of the indicator 64I relative to the ruler 64R. The selected position may establish, or may otherwise be associated with, one or more settings or parameters specified in a respective surgical plan 33.

Various transfer guides may be utilized with the planning environment 27 to implement the surgical plan(s) 33, including any of the transfer guides disclosed herein. Each transfer guide may be associated with a respective transfer model 48. The disclosed transfer guides may be configured to set a position and orientation of the respective implant prior to fixing or otherwise securing the implant at a surgical site. The disclosed transfer guides may be configured to orient or otherwise position one or more surgical devices relative to the patient anatomy, including articular and/or non-articular surfaces of bones.

Figure 4:
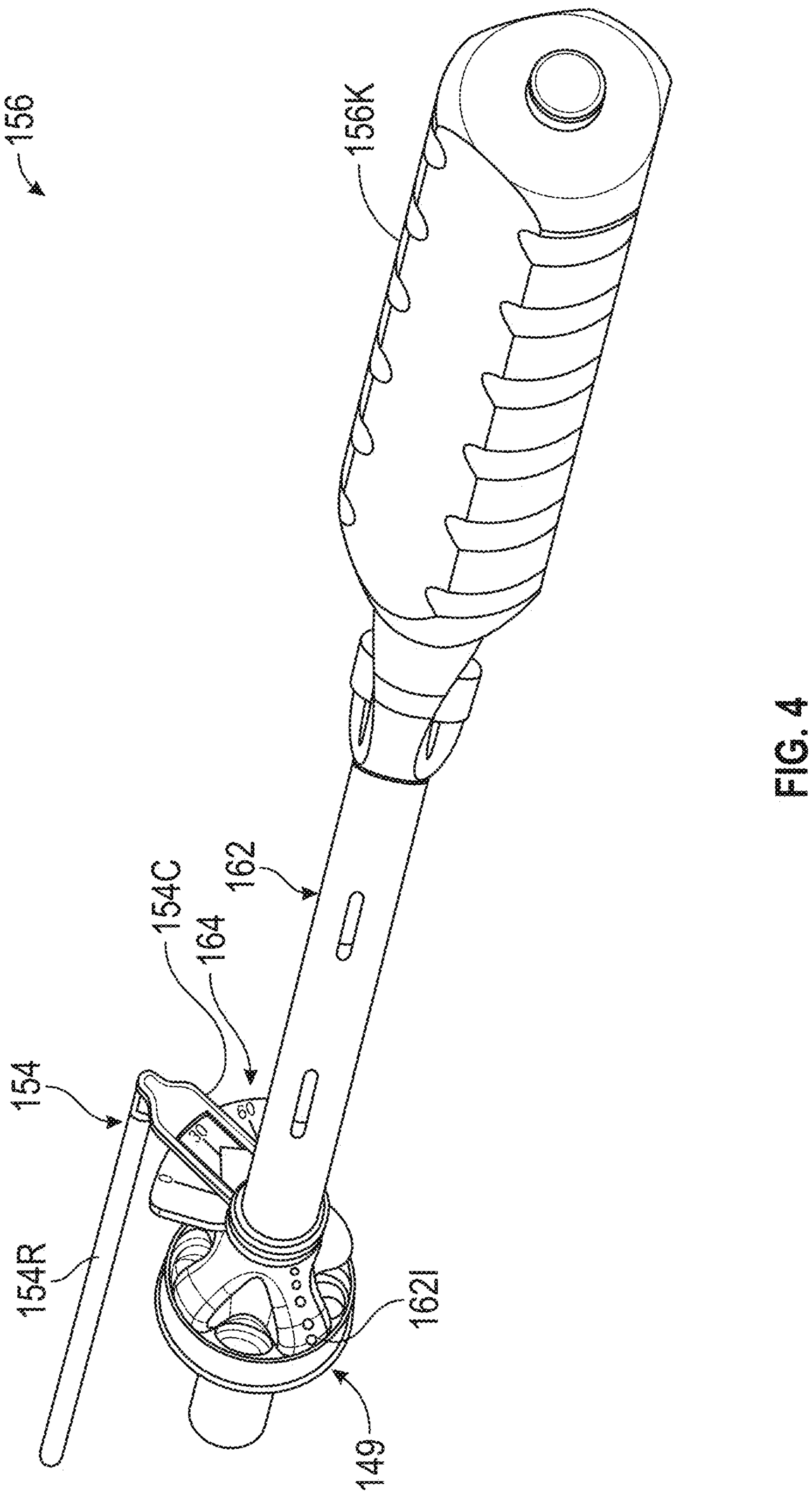
FIG. 4 illustrates a perspective view of a transfer guide coupled to an implant.

FIG. 4 illustrates a transfer guide 156 that may be utilized for an orthopedic procedure. In this disclosure, like reference numerals designate like elements where appropriate and reference numerals with the addition of one-hundred or multiples thereof designate modified elements that are understood to incorporate the same features and benefits of the corresponding original elements. The transfer guide 156 may be associated with a respective transfer model 48 (FIG. 2). The transfer guide 156 may be configured to mount or otherwise secure a surgical device such as an implant 149. The implant 149 may be secured or otherwise positioned relative to an articular surface and/or non-articular surface of a bone. The implant 149 may be utilized to restore functionality to a joint, such as a shoulder, hip, knee or ankle joint. The transfer guide 156 may be utilized to establish a position and/or orientation of the implant 149 or other surgical device relative to the patient anatomy, such as an articular and/or non-articular surface of a bone. The implant 149 may be associated with a respective implant model 32 (FIG. 2).

Figure 5:
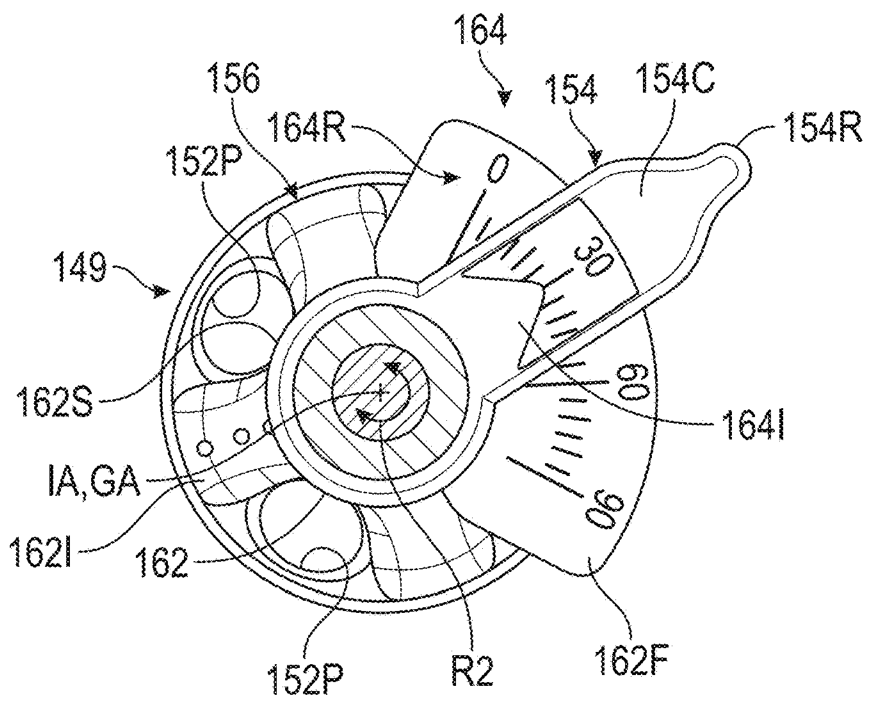
FIG. 5 illustrates a sectioned, axial view of the transfer guide of FIG. 4.
Figure 6:
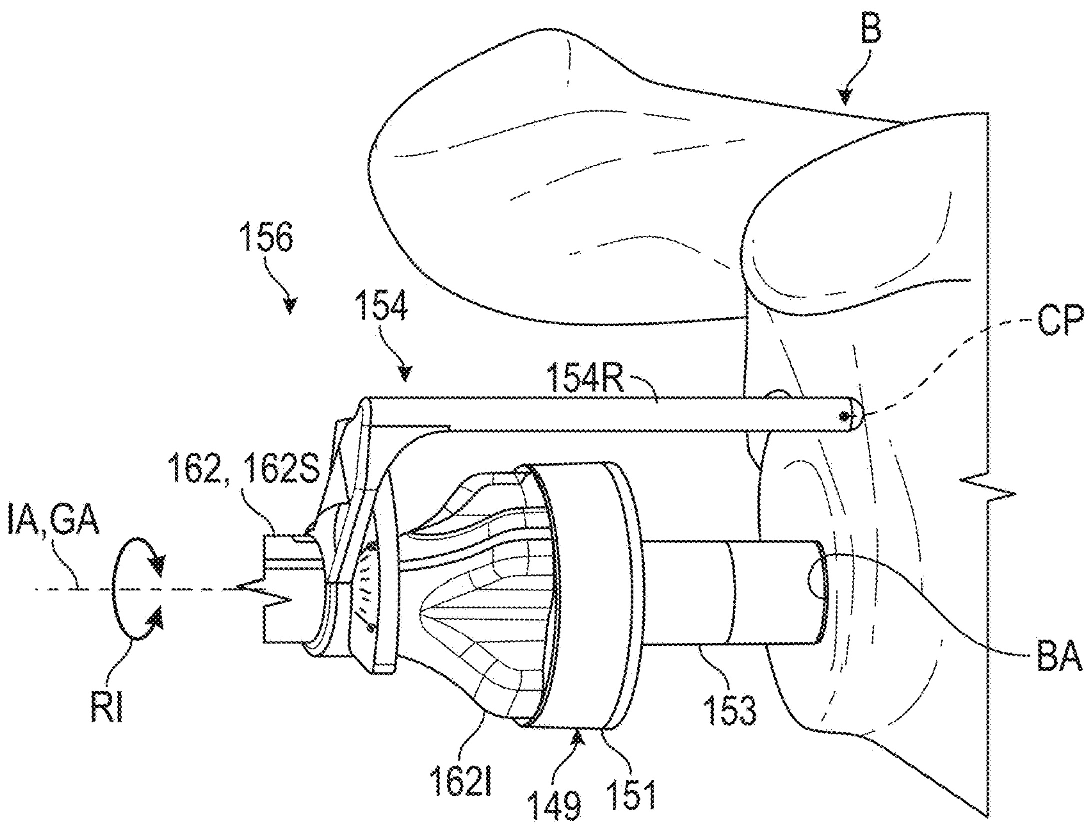
FIG. 6 illustrates a perspective view of portions of the transfer guide of FIG. 4 with the implant situated relative to a bone.

Referring to FIGS. 5-6, with continuing reference to FIG. 4, the transfer guide 156 may include a guide body 162. The guide body 162 may include an elongated guide shaft 162S. The guide shaft 162S may extend along a guide axis GA between a proximal end and a distal end. The transfer guide 156 may include a handle 156H (FIGS. 4 and 6). The handle 156H may be manipulated by the surgeon to position the transfer guide 156 relative to the surgical site. The handle 156H may be established adjacent to the proximal end of the guide shaft 162S. The guide body 162 may include an interface portion (e.g., inserter) 1621. The interface portion 1621 may be established adjacent to the distal end of the guide shaft 162S. The implant 149 or other surgical device may be securable to the interface portion 1621. The interface portion 1621 may be dimensioned such that the guide axis GA may substantially coincide with, or may otherwise be substantially parallel to, an implant axis IA of the implant 149 when coupled to the transfer guide 156.

The transfer guide 156 may have at least one transfer member 154 to establish an orientation of the transfer guide 156 relative to the patient anatomy. In implementations, the transfer guide 156 may have more than one transfer member 154, such as two or three transfer members 154 distributed about the guide axis GA. Each transfer member 154 may be coupled to the guide body 162. The transfer member 154 may be moveable relative to the guide axis GA and/or guide body 162.

The transfer member 154 may have various configurations to establish an orientation of the transfer guide 156 relative to the patient anatomy. The transfer member 154 may include a carrier 154C and an outrigger 154R. The outrigger 154R may extend distally from the carrier 154C relative to the guide axis GA. The outrigger 154R may be configured to set an orientation of the implant 149 or other surgical device relative to the patient anatomy. In implementations, the carrier 154C and outrigger 154R may be integrally formed. In other implementations, the carrier 154C and outrigger 154R may be separate and distinct components fixedly attached or otherwise secured to each other. The outrigger 154R may be configured to have various lengths and diameters to accommodate the patient anatomy.

The carrier 154C may be rotatable about a periphery of the guide body 162 to set a position of the outrigger 154R. The carrier 154C may be rotatable in a second rotational direction R2 (FIG. 5) about the guide axis GA to set a position of the outrigger 154R. The outrigger 154R may be configured to contact bone and/or other tissue at a respective contact point CP to set an orientation of the guide body 162 (see, e.g., FIGS. 6-8).

The transfer guide 156 may include an alignment mechanism 164 for indicating a position of the transfer member 154 relative to the guide body 162. The alignment mechanism 164 may be established according to any of the techniques disclosed herein. The alignment mechanism 164 may be configured to indicate a circumferential position of the outrigger 154R relative to the guide axis GA. The alignment mechanism 164 may include a ruler 164R and an indicator 164I adjacent the ruler 164R that may cooperate to establish a protractor. The ruler 164R may include indicia associated with respective circumferential positions of the outrigger 154R relative to the guide axis GA. The indicator 164 may be established along a portion of the carrier 154C, and the ruler 164R may be fixedly attached or otherwise secured to the guide body 162, although an opposite configuration may be utilized. In implementations, the ruler 164R may be established along a flange 162F. The flange 162F may extend outwardly from a periphery of the shaft 162S or another portion of the guide body 162.

The indicator 164I may be movable relative to the ruler 164R to indicate a circumferential position of the outrigger 154R relative to the guide axis GA of the guide body 162. In implementations, the indicator 164I may be movable in a second rotational direction R2 (FIG. 5) relative to the guide axis GA to set a position of the indicator 164I relative to the ruler 164R. The indicator 164I may be aligned with a selected position along the ruler 164R. The selected position may be associated with one or more settings or parameters specified in a respective surgical plan 33, such as a circumferential position of an outrigger 54R of a respective transfer member 48 associated with the surgical plan 33 (see, e.g., FIG. 3B).

Referring to FIG. 6, with continuing reference to FIGS. 4-5, in use the surgeon or clinical assistant may configure the transfer guide 156. The surgeon or assistant may set a circumferential position of the outrigger 154R relative to the guide axis GA of the guide body 162. The circumferential position of the outrigger 154R may substantially correspond to one or more settings or parameters specified in a surgical plan 33 for a patient. The surgeon or clinical assistant may secure a selected implant 149 to the transfer guide 156, prior to, during or subsequent to configuring the transfer guide 156. The surgeon may position the implant 149 relative to a bone B. A portion of the implant 149 may be at least partially inserted in an aperture BA that may be pre-piloted or otherwise formed in the bone B.

Situating the implant 149 relative to the bone B may cause the outrigger 154R to contact the bone B along a respective contact point CP. Contact between the outrigger 154R and the bone B at the contact point CP may occur in response to rotating the implant 149 together with the transfer guide 156 as a unit in a first rotational direction R1 about the implant axis IA. The position of the implant 149 relative to the contact point CP may be associated with an orientation of an implant model 32 specified in a respective surgical plan 33.

Figure 7:
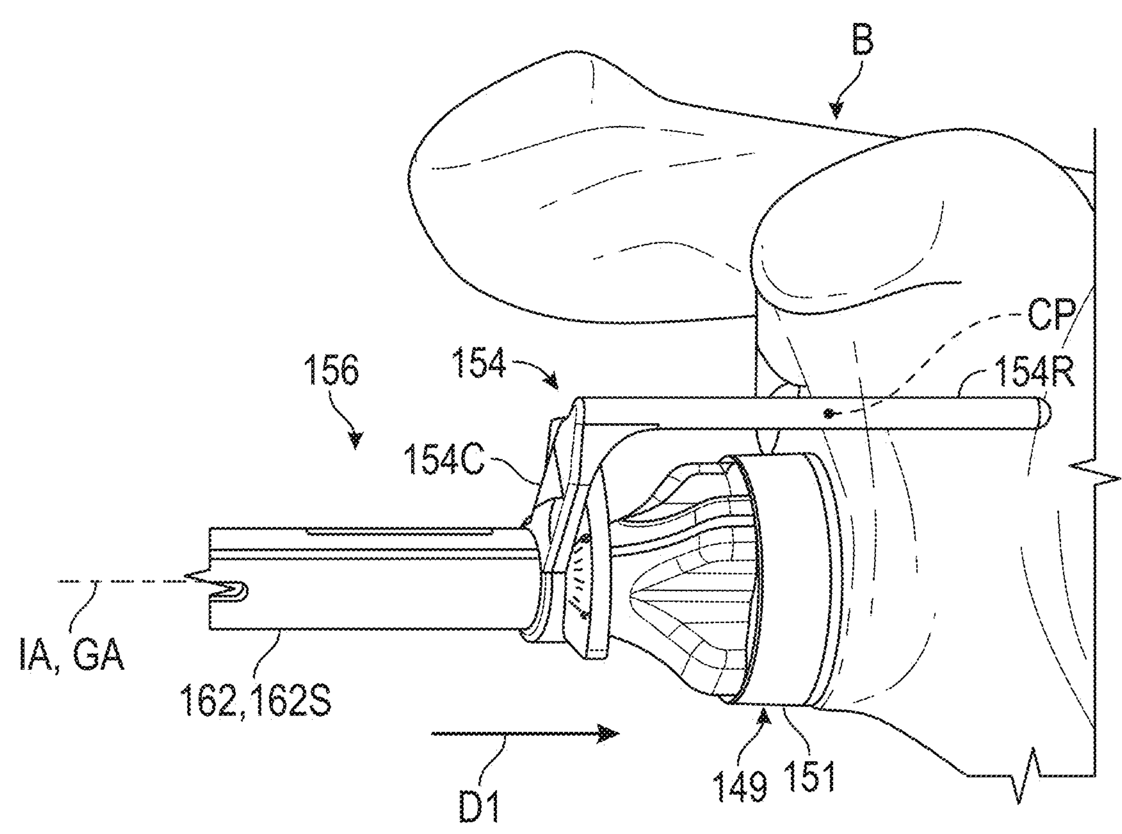
FIG. 7 illustrates a perspective view of the transfer guide of FIG. 6 with the implant seated against the bone.
Figure 8:
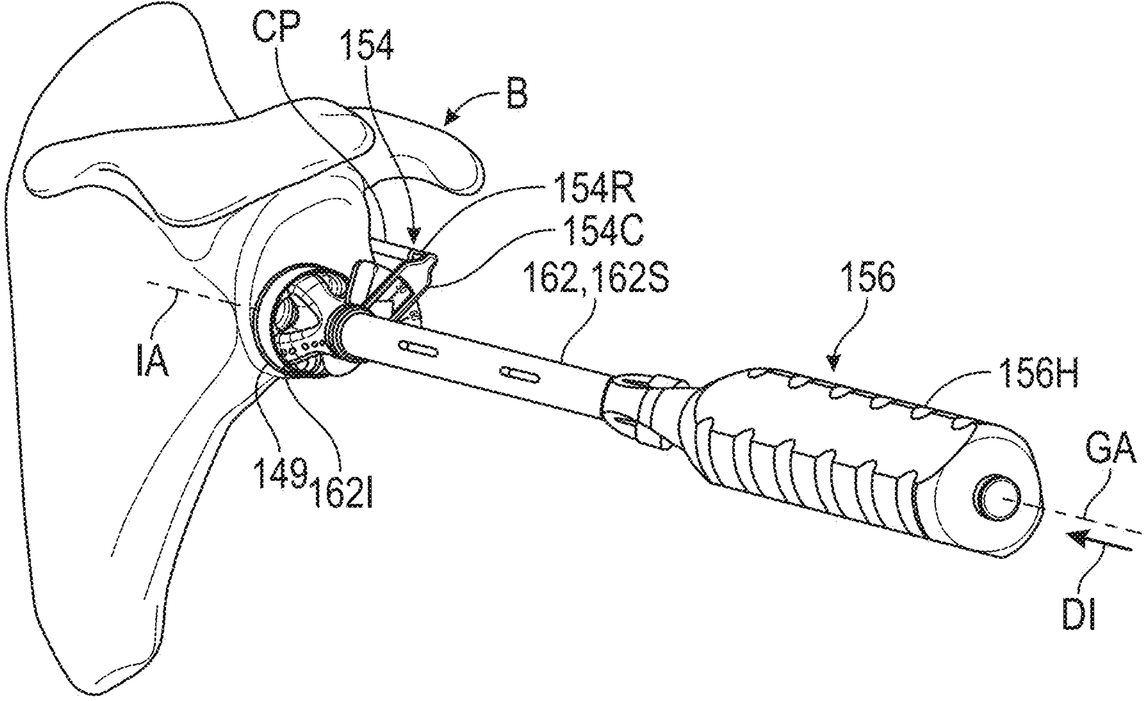
FIG. 8 illustrates a perspective view of the transfer guide of FIG. 7.

Referring to FIGS. 7-8, with continuing reference to FIG. 6, the implant 149 and transfer guide 156 may be moved together in a first direction D1 to seat the implant 149 relative to the bone B. The first direction D1 may be substantially parallel to the guide axis GA. The implant 149 may be positioned along the bone B at a circumferential position associated with the contact point CP established by the outrigger 154R. In the implementation of FIGS. 7-8, the carrier 154C may be secured to the guide body 162 at a fixed axial position relative to the guide axis GA such that the contact point CP is established at different positions along a length of the outrigger 154R in response to movement of the transfer guide 156 in the first direction D1 towards the bone B.

Figure 9:
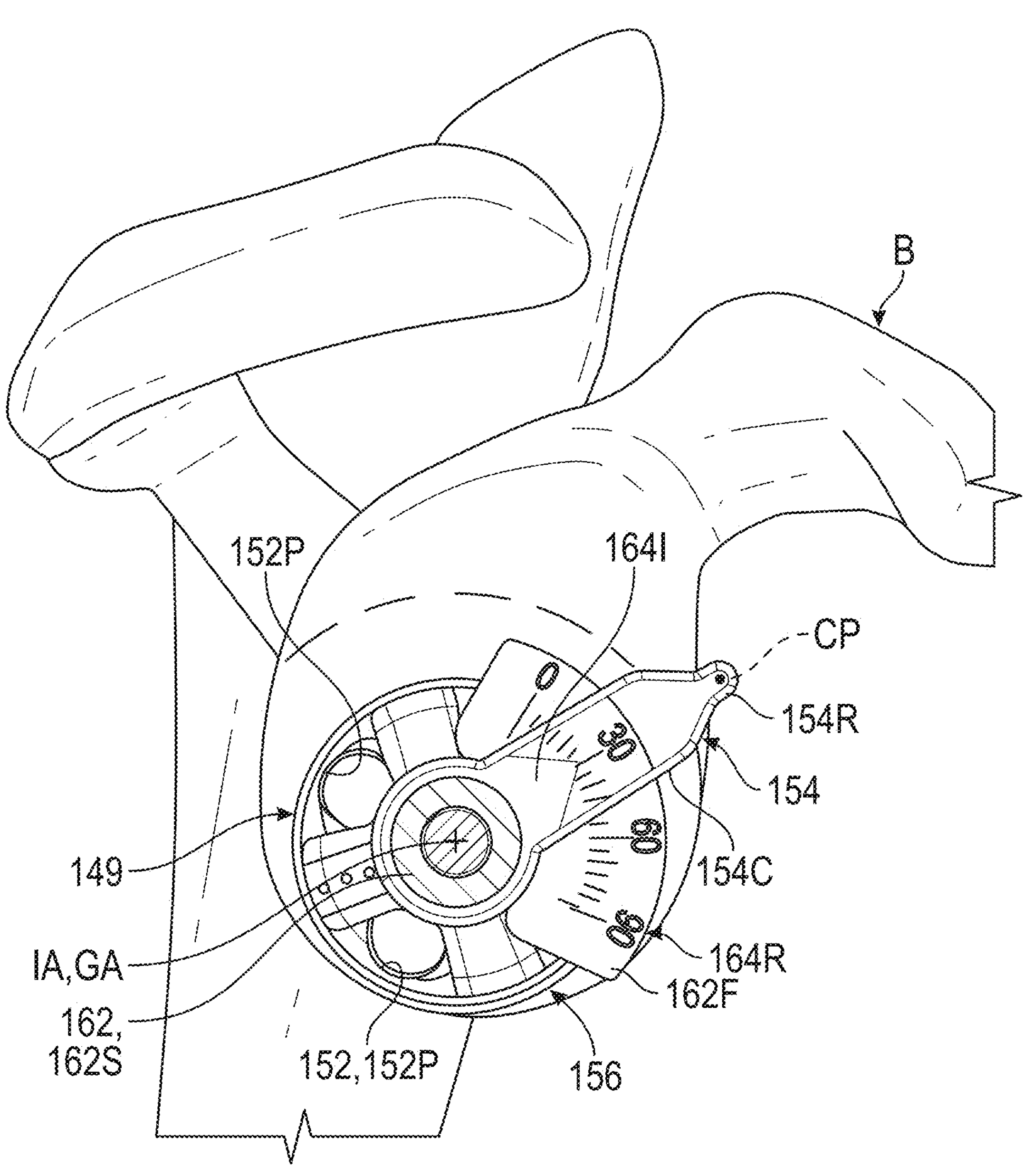
FIG. 9 illustrates a sectioned, axial view of the transfer guide of FIG. 8.

Referring to FIG. 9, with continuing reference to FIGS. 7-8, the implant 149 may include a plurality of apertures 152. Thee apertures 152 may include one or more peripheral apertures 152P (see also FIG. 5). The peripheral apertures 152P may be uniformly or non-uniformly distributed about the implant axis IA of the implant 149. The implant 149 may be oriented relative to the bone B such that the peripheral apertures 152P may be oriented relative to the guide axis GA according to one or more settings or parameters specified in a respective surgical plan 33. The orientation of the peripheral apertures 152P may be established according to an orientation of the contact point CP relative to the guide axis GA.

Figure 10:
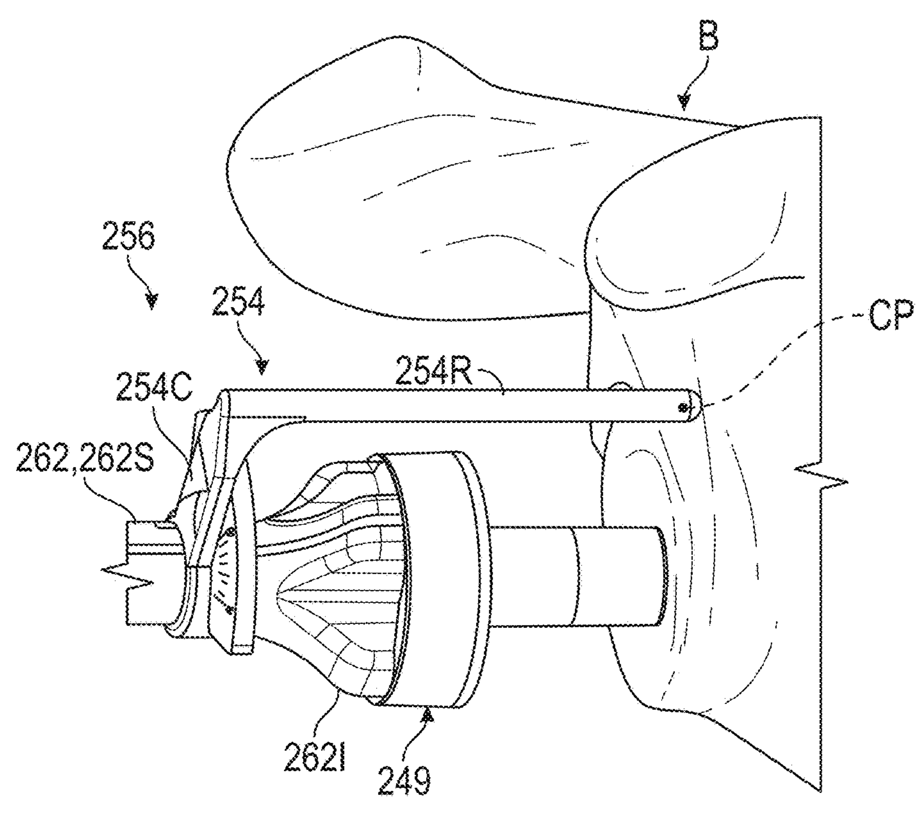
FIG. 10 illustrates a perspective view of a transfer guide according to another implementation including a guide body at a first axial position.
Figure 11:
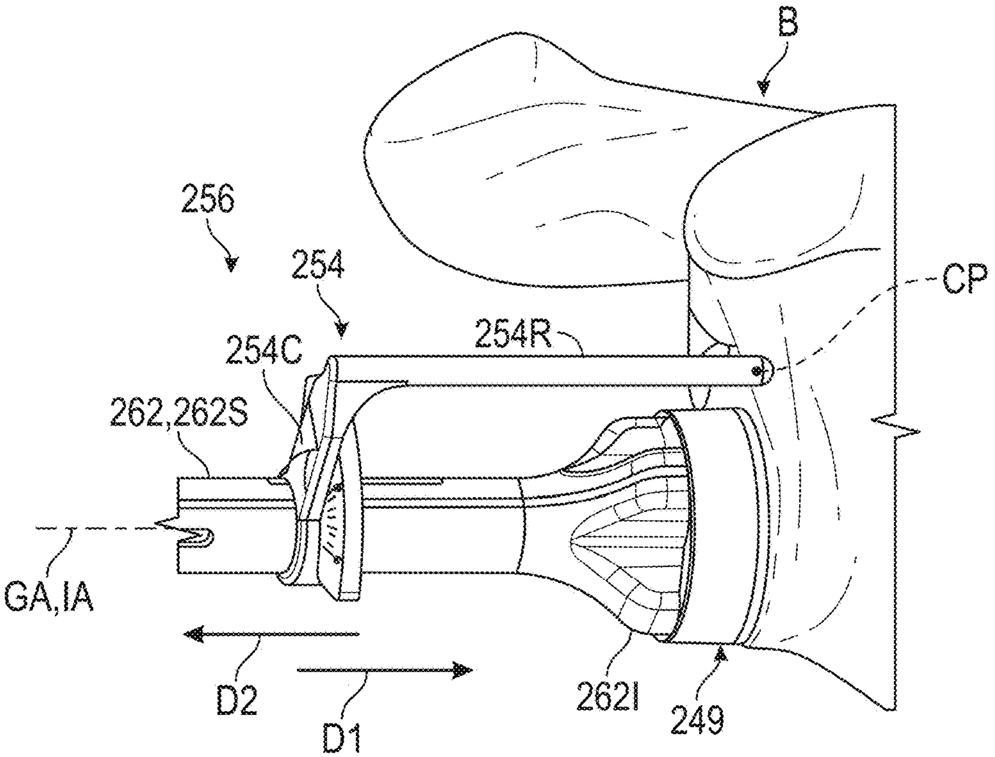
FIG. 11 illustrates a perspective view of the transfer guide of FIG. 10 including the guide body at a second axial position.

FIGS. 10-11 disclose another implementation of a transfer guide 256 for an orthopaedic procedure. The transfer guide 256 may include at least one transfer member 254 secured to a guide body 262. An interface portion 2621 of the transfer guide 256 may be securable to an implant 249. The transfer member 254 may include a carrier 254C and outrigger 254R. The outrigger 254R may be configured to establish contact with bone B at a contact point CP. The carrier 254C may be movable along a periphery of the guide body 262 relative to a guide axis GA. The transfer guide 256 may be moveable in a first direction D1 to position the implant 249 along the bone B. The carrier 254C may be movable in a second direction D2 along the periphery of the guide body 262 relative to the guide axis GA in response to moving the guide body 262 in the first direction D1 subsequent to establishing contact between the outrigger 254R and bone B at the contact point CP. The second direction D2 may be substantially parallel to the guide axis GA and may be opposed to the first direction D1.

Figure 12:
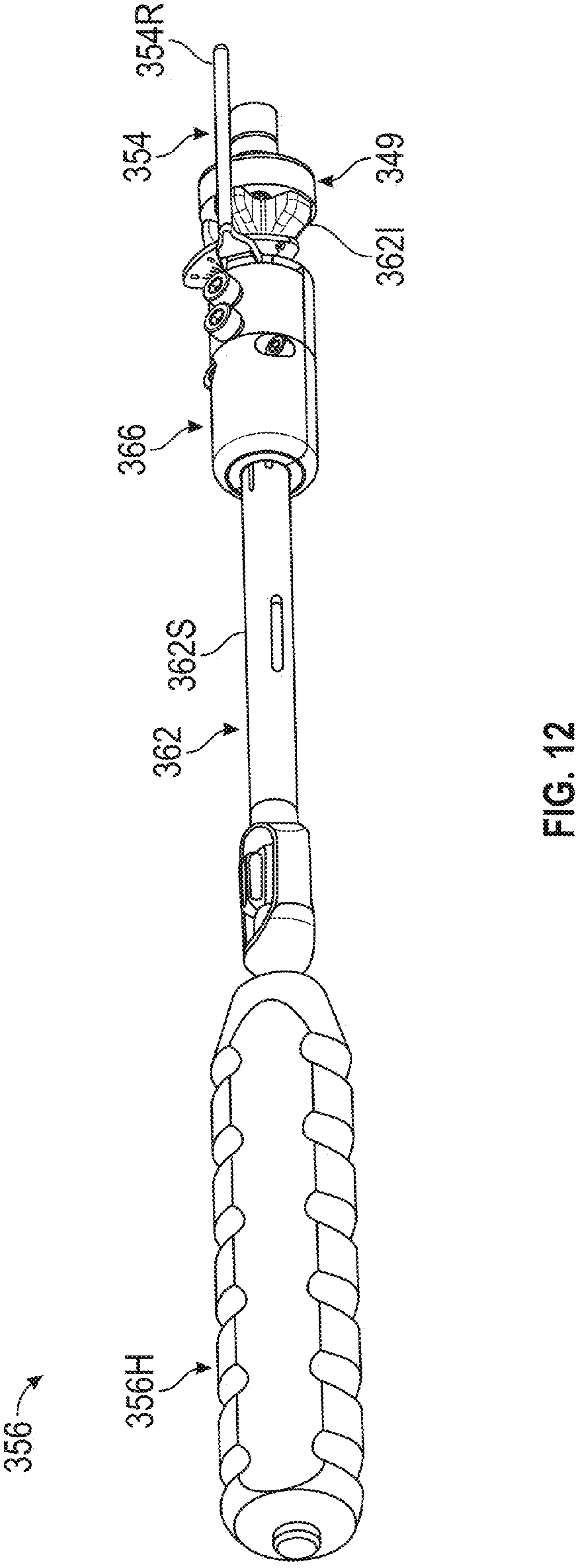
FIG. 12 illustrates a perspective view of a transfer guide coupled to an implant according to another implementation.

FIG. 12 illustrates another implementation of a transfer guide 356 for an orthopedic procedure. The transfer guide 356 may include a transfer member 354 coupled to a guide body 362. The guide body 362 may include a guide shaft 362S. A handle 356H may be secured to the guide shaft 362S. The guide body 362 may include an interface portion 362I. The interface portion 362I may be configured to mount, or may otherwise be secured to, an implant 349.

Figures 13, 14:
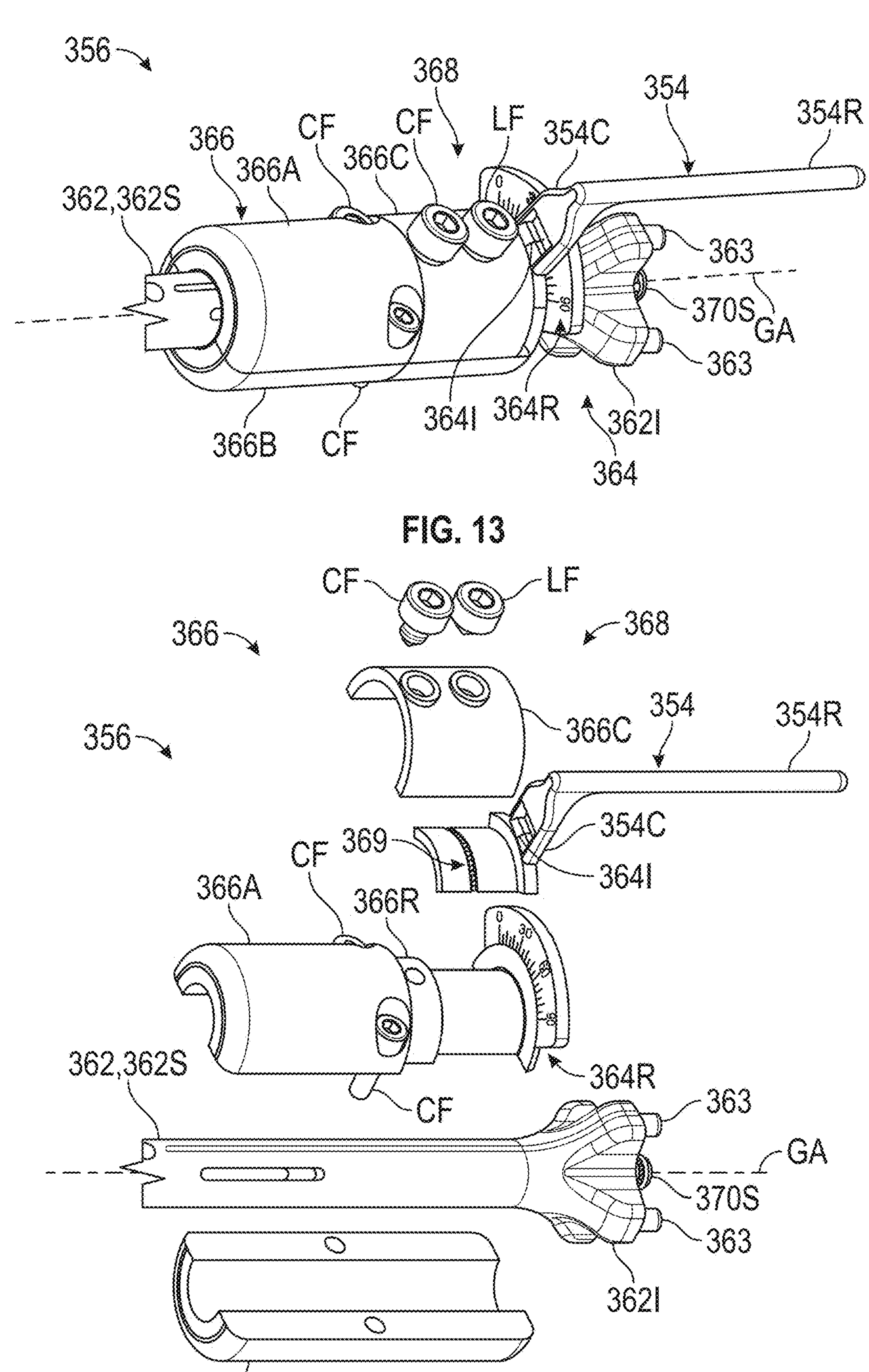
FIG. 13 illustrates a perspective view of portions of the transfer guide of FIG. 12.
FIG. 14 illustrates an exploded view of the transfer guide of FIG. 13.

Referring to FIGS. 13-14, with continuing reference to FIG. 12, the interface portion 362I may include a plurality of protrusions 363. In implementations, the protrusions 363 may be an array of protrusions 363 circumferentially distributed about the guide axis GA. The protrusions 363 may be dimensioned to mate with an array with insertion apertures 352IA of the implant 349 to limit relative rotation between the guide shaft 362S and the implant 349 with respect to the guide axis GA (see, e.g., FIGS. 33A-33B). In other implementations, the protrusions 363 may be incorporated into the implant 349, and the insertion apertures 352IA may be incorporated into the interface portion 362I of the transfer guide 356.

The transfer guide 356 may include a coupling 366. The coupling 366 may be configured to fixedly attach or otherwise secure the transfer member 354 and guide body 362 to each other. The coupling 366 may include a first coupling component 366A and a second coupling component 366B. Each of the coupling components 366A, 366B may be dimensioned to extend approximately 180 degrees about the guide axis GA. The coupling components 366A, 366B may be configured to mate with each other to capture a portion of the guide shaft 362S. The coupling components 366A, 366B may cooperate to establish an elongated passage 366P (see, e.g., FIGS. 15-16). The passage 366P may be dimensioned to receive a length of the guide shaft 362S. The coupling components 366A, 366B may be secured to each other using various techniques, such as with one or more fasteners CF.

The carrier 354C of a selected transfer member 354 may be releasably securable to the coupling 366. In implementations, the coupling 366 may include a third coupling component (e.g., clamp) 366C. The clamp 366C may be configured to be releasably secured to the carrier 354C. The clamp 366C may be releasably securable to the first coupling component 366A to capture a portion of the carrier 354C of a selectable one of the transfer members 354 along a periphery of the first coupling component 366A. The clamp 366C may be dimensioned to extend approximately 180 degrees about the guide axis GA. The clamp 366C may be at least partially received in a recess 366R established along a periphery of the first coupling component 366A (see, e.g., FIGS. 14-16). The clamp 366C may be securable to the first coupling component 366A utilizing various techniques, such as with a fastener CF.

Figure 15:
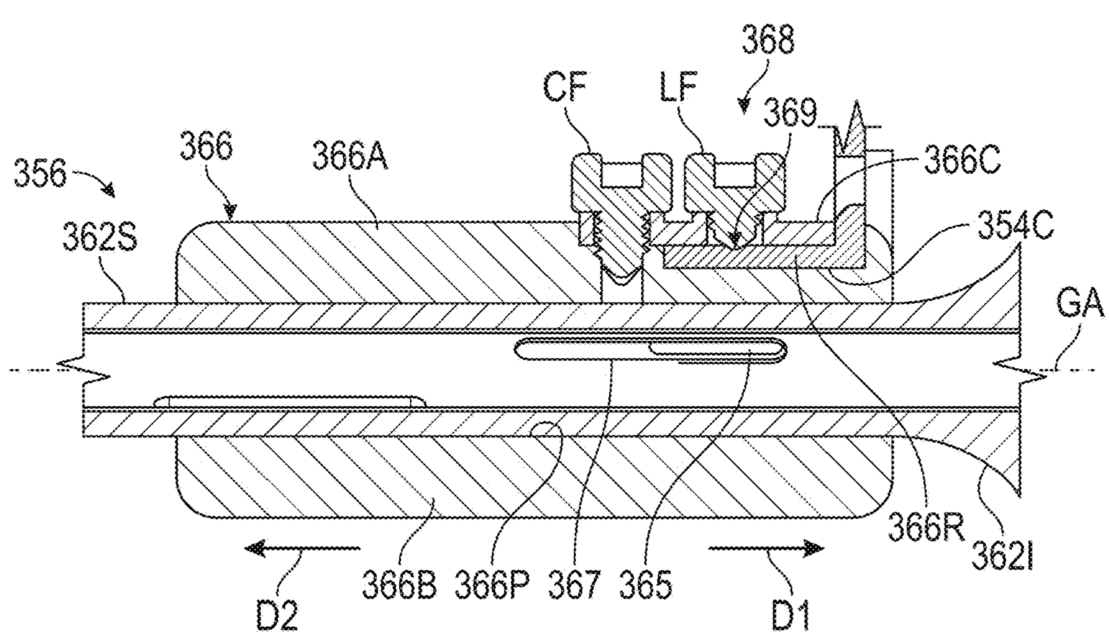
FIG. 15 illustrates a sectional view of the transfer guide of FIG. 13 including a coupling at a first axial position.

The clamp 366C may include a lock mechanism 368. The lock mechanism 368 may be configured to set a position of the outrigger 354R with respect to the guide axis GA. The lock mechanism 368 may be configured to lock the outrigger 354R at a preplanned value along the ruler 364R. In implementations, the lock mechanism 368 may include a lock fastener (e.g., set screw) LF. The lock fastener LF may be configured to engage a surface of the carrier 354C to limit or otherwise oppose rotation of the carrier 354C about the guide axis GA. In the implementation of FIGS. 14-15, the carrier 354C may include one or more depressions (e.g., notches) 369. The depressions 369 may be associated with respective circumferential positions about the guide axis GA. The fastener LF may be configured to engage a selectable one of the depressions 369 to set or establish the circumferential position of the carrier 354C relative to the guide axis GA. Engagement between the lock fastener LF and the selected depression 369 may limit or otherwise oppose relative rotation between the carrier 354C and guide axis GA.

The coupling 366 may be moveable along the guide axis GA to set an axial position of the outrigger 354R relative to the guide axis GA. Axial movement of the coupling 366 along the guide shaft 362S may limit an axial length of the outrigger 354R that may extend past the contact point CP and may reduce a likelihood that the outrigger 354R may cause trauma to soft tissue adjacent the bone B.

Figure 16:
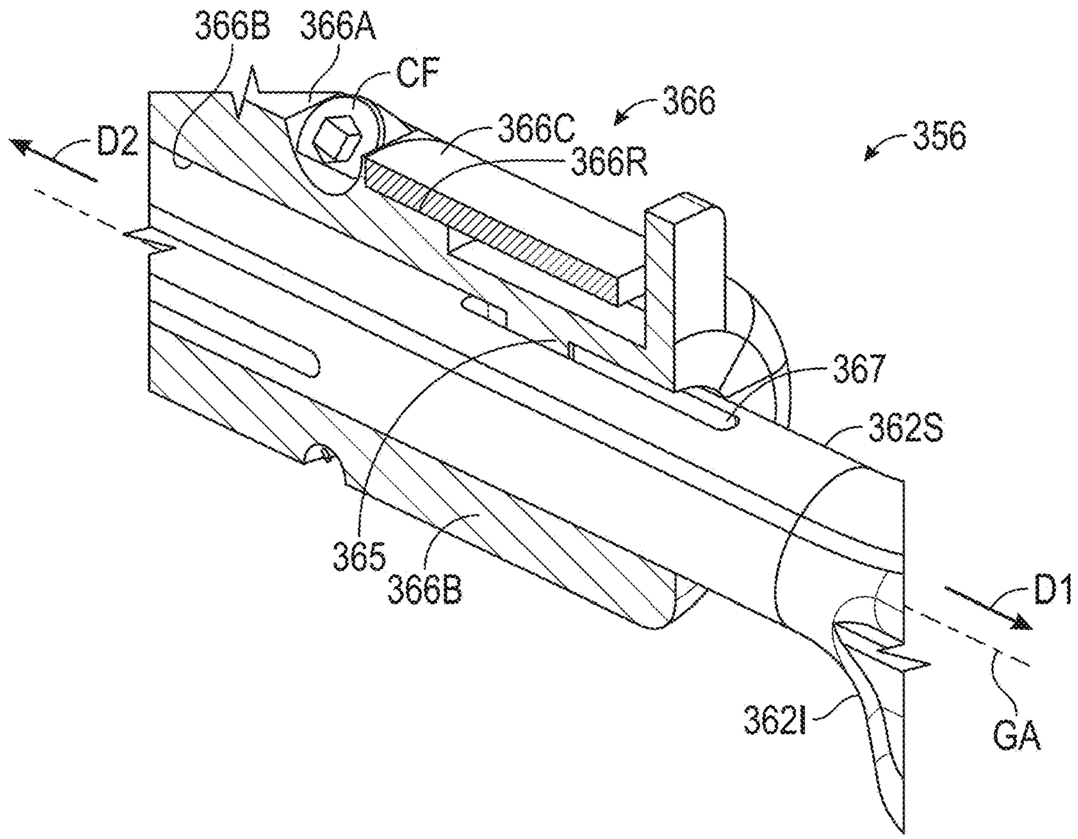
FIG. 16 illustrates a sectional view of the transfer guide of FIG. 13 including the coupling at a second axial position.

The transfer guide 356 may be configured to limit or otherwise oppose circumferential and/or axial movement between the guide shaft 362S and coupling 366. Referring to FIGS. 15-16, a groove 367 may extend along one of the coupling 366 and the guide shaft 362S, and a protrusion 365 may extend along another one of the coupling 366 and the guide shaft 362S. The protrusion 365 may be at least partially received in the groove 367. In the implementation of FIGS. 15-16, the groove 367 may extend along the guide shaft 362S, and the protrusion 365 may extend along the coupling 366. The protrusion 365 may be established along the first coupling component 366A of the coupling 366. The protrusion 365 may be moveable along a length of the groove 365. The protrusion 365 may be engageable with opposed circumferential walls bounding the groove 367 to limit rotation of the coupling 366 about the guide axis GA. The protrusion 365 may be moveable in the first direction D1 and/or the second direction D2 relative to the guide axis GA. A length of the groove 367 may be dimensioned to limit axial movement of the coupling 366 relative to the guide axis GA. The protrusion 365 may be engageable with opposed axial walls bounding the groove 367 to limit axial movement of the coupling 366 along the guide axis GA.

Figure 17:
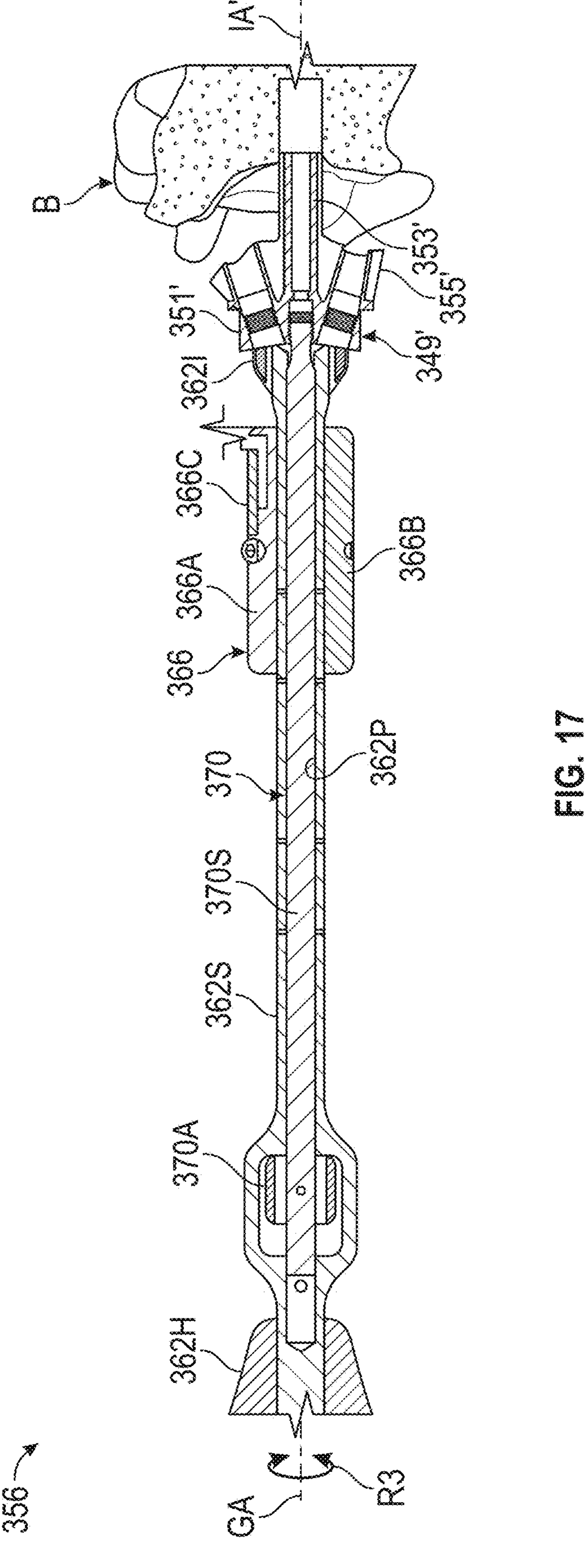
FIG. 17 illustrates a sectional view of the transfer guide of FIG. 12 coupled to another implant positioned relative to bone.

Referring to FIG. 17, with continuing reference to FIGS. 12-16, the transfer guide 356 may include a coupling mechanism 370. The coupling mechanism 370 may include a coupling shaft 370S secured to an actuator 370A. The actuator 370A may be a knob or other device that may be rotatable in a third rotational direction R3 to rotate the coupling shaft 370S about the guide axis GA.

Figure 18:
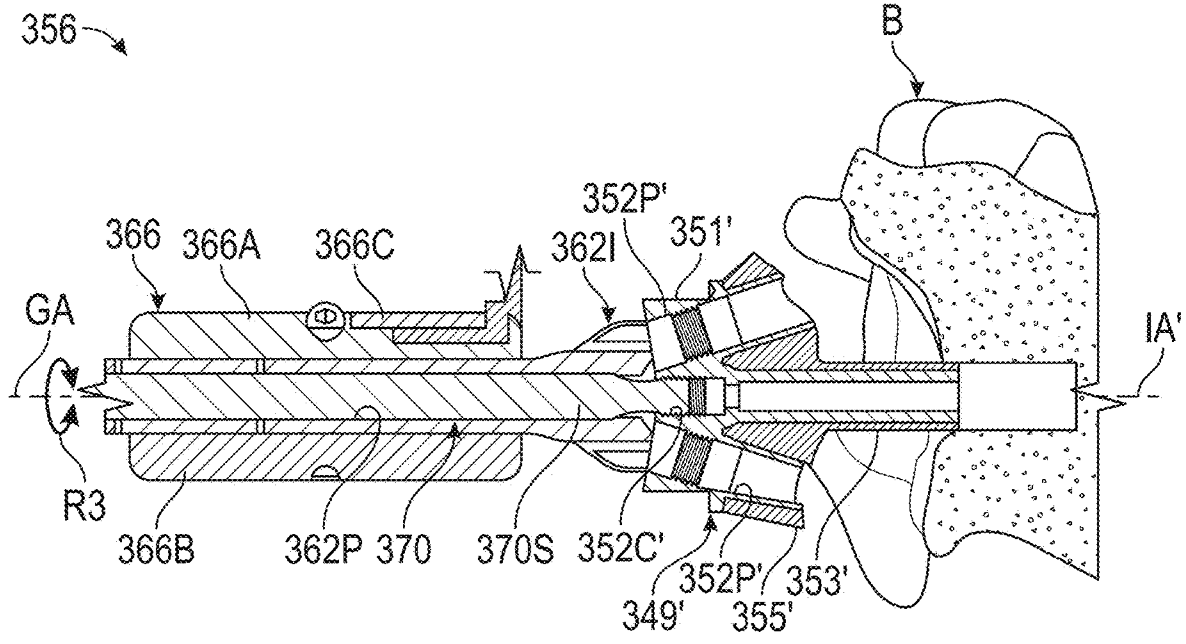
FIG. 18 illustrates a sectional view of portions of the transfer guide of FIG. 17.
Figure 19:
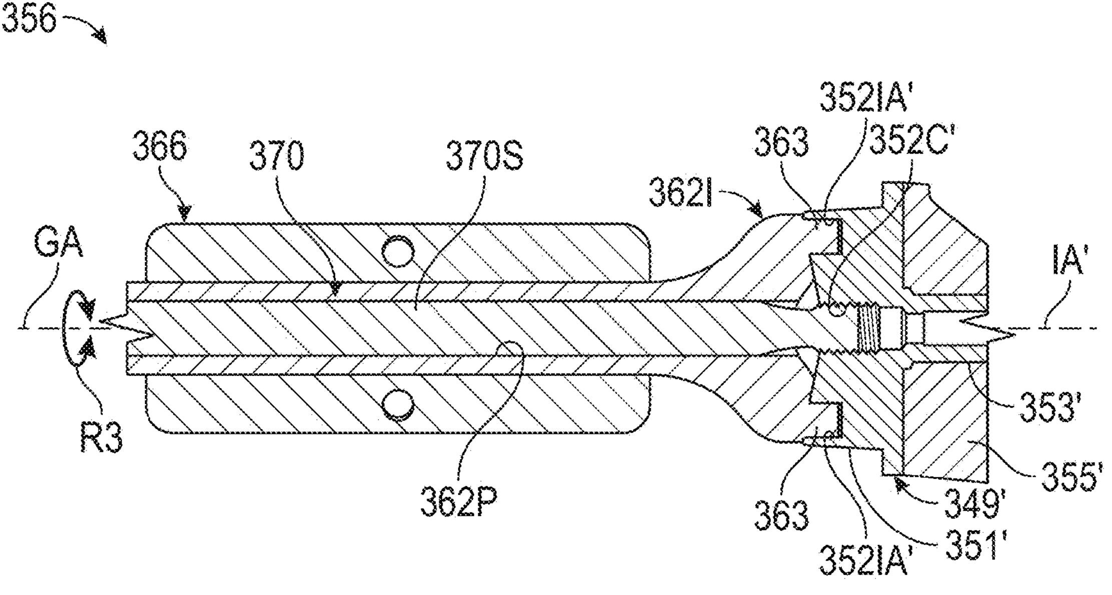
FIG. 19 illustrates another sectional view of portions of the transfer guide of FIG. 17.

Referring to FIGS. 18-19, with continuing reference to FIG. 17, the coupling shaft 370S may be at least partially received in a passage 362P established within the guide shafts 362S. A distal end portion of the coupling shaft 370S may be coupled to a respective implant 349'. The implant 349' may include a baseplate 351' and a plurality of apertures 352'. The baseplate 351' may include a main (e.g., plate) body. The apertures 352' may include a central aperture 352C', an array of peripheral apertures 352P', and an array of interface apertures 352IA'. The central aperture 352C' may be dimensioned to extend along an implant axis IA' of the implant 349'. The implant 349' may include an anchor member (e.g., alignment member or stem) 353'. The anchor member 353' may extend outwardly from a rear face of the baseplate 351'. A rear face of the implant 349' may have a non-symmetrical surface profile. In implementations, the implant 349' may include an augment 355' extending along the baseplate 351'. The augment 355' and/or another portion of the implant 349' may be dimensioned with respect to a preoperative, patient-specific surface contour of the bone B. In implementations, the implant 349' may have a rear surface established by the augment 355' that may substantially correspond to a surface contour of a respective bone B (see, e.g., FIG. 18). Utilizing the techniques disclosed herein, the rear surface of the implant 349' may be substantially seated against the surface of the bone B, which may improve fixation.

The distal end portion of the coupling shaft 370S and the respective aperture 352C' may be threadably connected to each other to secure the implant 349' and the transfer guide 356 to each other in response to rotation of the coupling shaft 370S in the third rotational direction R3. The implant 349' may be secured to the coupling shaft 370S in response to rotating the coupling shaft 370S in a clockwise direction, and may be released from the coupling shaft 370S in response to rotating the coupling shaft 370S in a counter-clockwise direction, or vice versa.

The interface portion 362I of the transfer guide 356 may include one or more protrusions 363. The protrusions 363 may be dimensioned to engage with respective interface apertures 352IA' of the implant 349' to limit or otherwise oppose relative rotation between the transfer guide 356 and the implant 349'. In implementations, the set of protrusions 363 may be registered with the set of interface apertures 352IA' in a plurality of configurations to establish an orientation of the implant 349' relative to the guide axis GA. The interface apertures 352IA' may be uniquely identified with indicia. Insertion of the protrusions 363 into the respective interface apertures 352IA' may be specified by one or more settings or parameters of a surgical plan 33. Insertion of the protrusions 363 into the respective interface apertures 352IA' may establish an orientation of the implant 349' relative to the guide axis GA and outrigger 354R (see also FIGS. 12 and 33A-33B). Pairings of the protrusions 363 and respective interface apertures 352IA' may be specified in the surgical plan 33 to establish a predetermined orientation of the implant 349' relative to the transfer guide 356.

Figure 20:
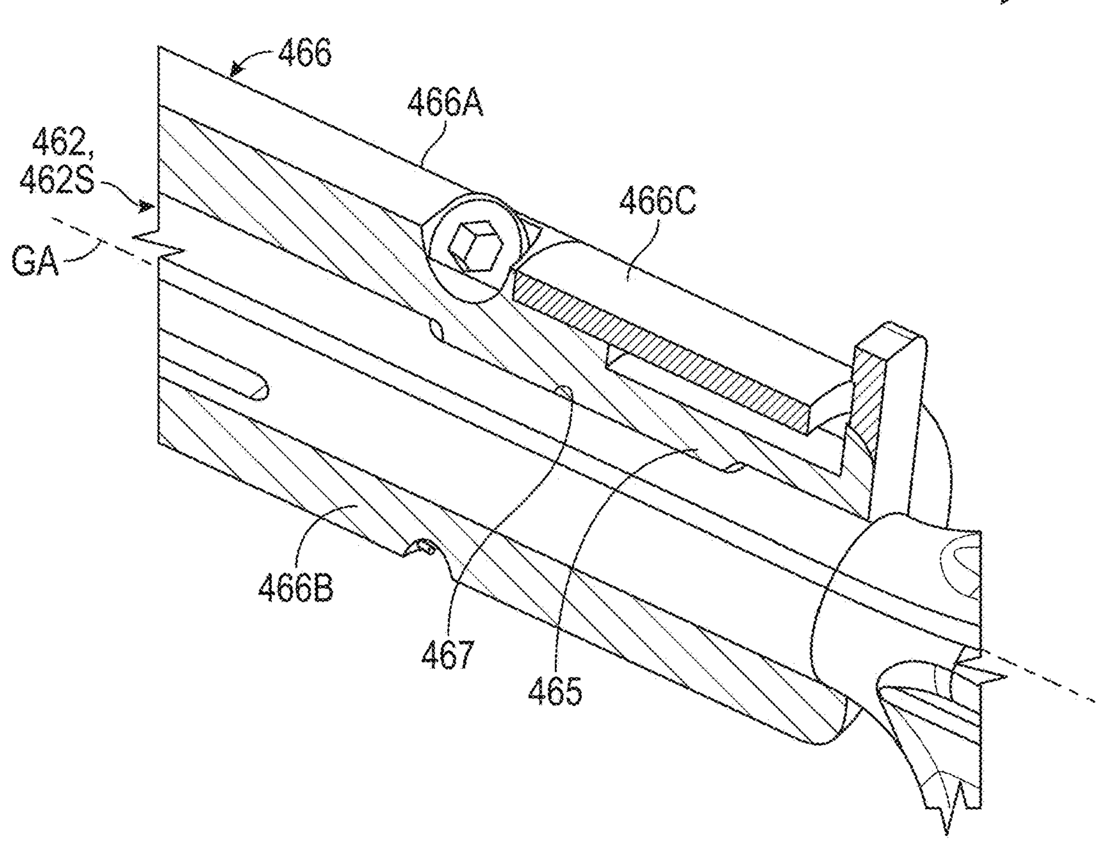
FIG. 20 illustrates a perspective, cutaway view of a transfer guide coupled to an implant according to another implementation.
Figure 21:
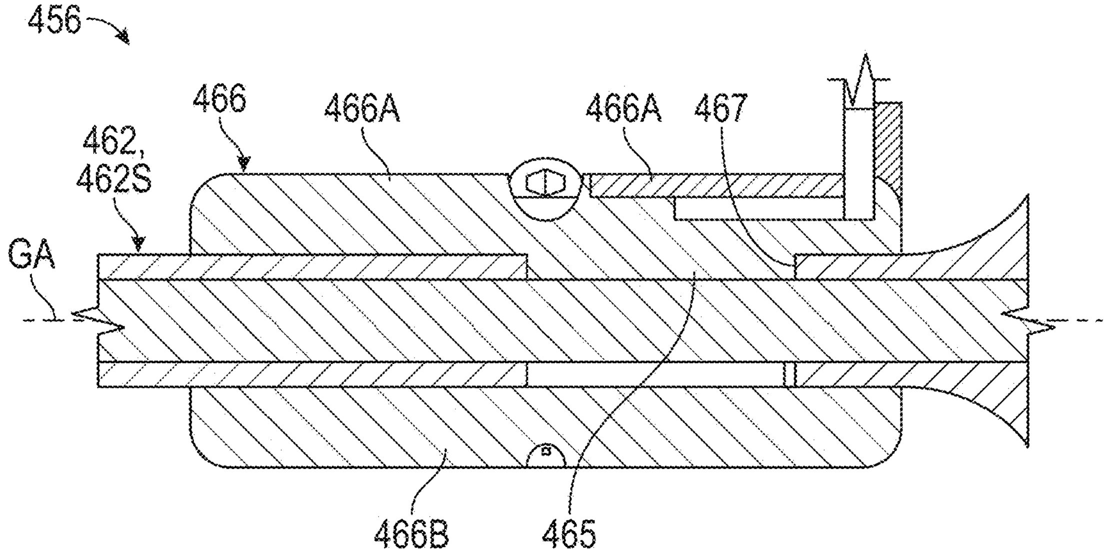
FIG. 21 illustrates a sectional view of the transfer guide of FIG. 20.

FIGS. 20-21 disclose another implementation of a transfer guide 456. The transfer guide 456 may include a protrusion 465 that may cooperate with a groove 467 to limit or otherwise oppose relative circumferential and/or axial movement of coupling 466 relative to guide shaft 462S. A length of the protrusion 465 may be dimensioned to substantially correspond to a length of the groove 467. The length of the groove 467 may be dimensioned to limit relative axial movement between the guide body 462 and coupling 466 relative to guide axis GA.

Figure 22:
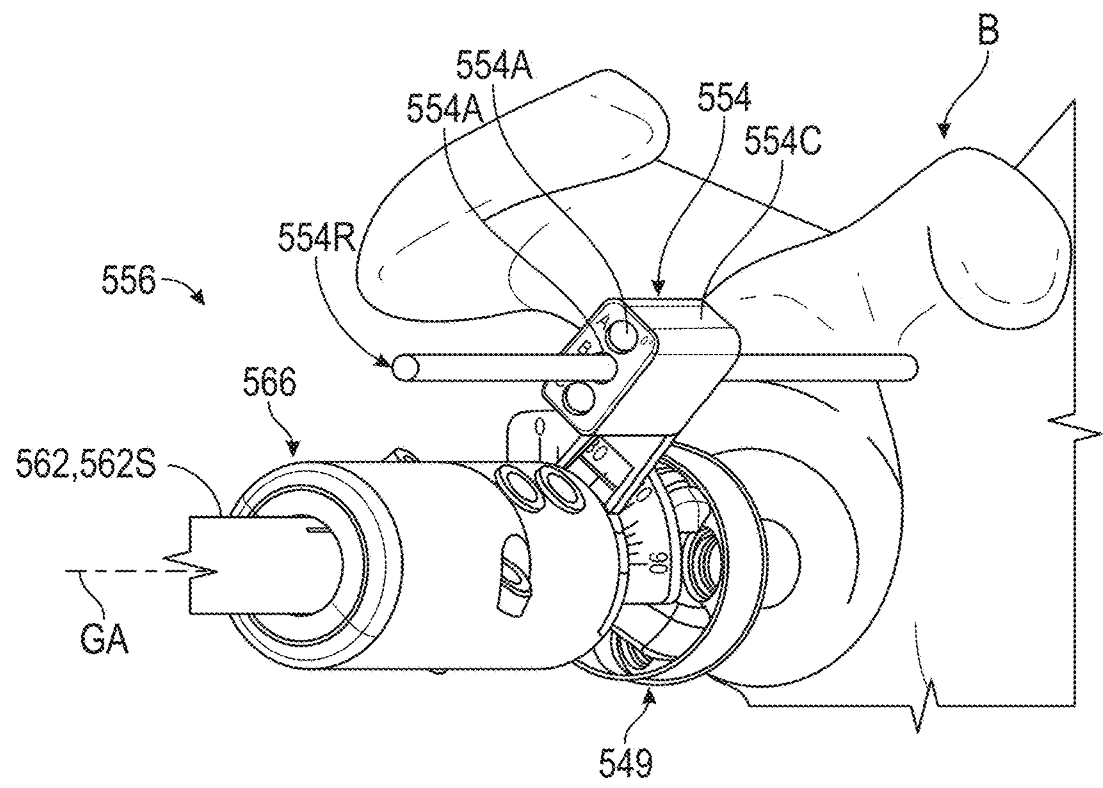
FIG. 22 illustrates a perspective view of a transfer guide coupled to an implant according to another implementation.
Figure 23:
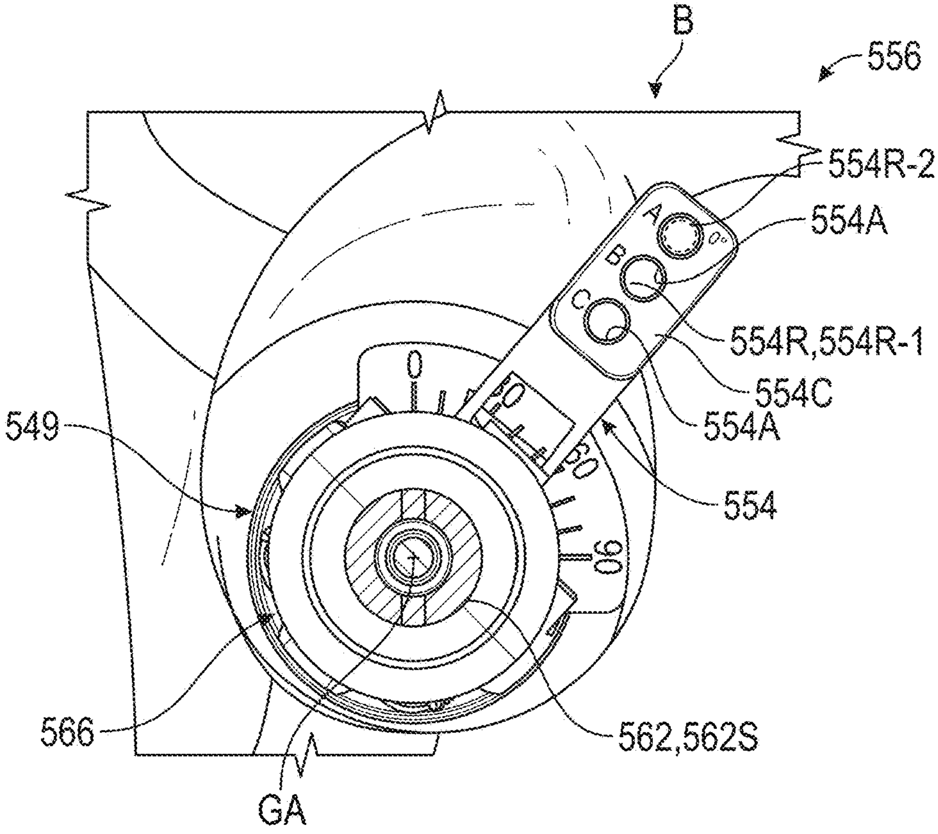
FIG. 23 illustrates a sectioned, axial view of the transfer guide of FIG. 22.
Figure 24:
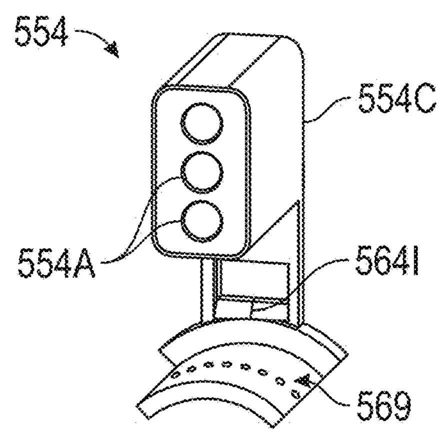
FIG. 24 illustrates a transfer member that may be coupled to the transfer guide of FIG. 22.

The transfer member may include other configurations to establish an orientation of the transfer guide relative to the patient anatomy. FIGS. 22-23 illustrate a transfer guide 556 according to another implementation. The transfer guide 556 may include at least one transfer member 554 and guide body 562. The transfer member 554 may include a carrier 554C and outrigger 554R. The outrigger 554R may be separate and distinct from the carrier 554C. The carrier 554C may be releasably secured to the guide body 562 (see also FIG. 24). The carrier 554C may be secured to the guide body 562 at a selectable position relative to a guide axis GA. The selectable position may be specified in the surgical plan 33.

The carrier 554C may include at least one aperture 554A dimensioned to receive the outrigger 554R. In implementations, the carrier 554C may include a plurality of apertures 554A. The apertures 554A may be distributed in a radial and/or circumferential direction relative to the guide axis GA of the guide body 562. The apertures 554A may be arranged in one or more columns and/or rows relative to the guide axis GA.

The outrigger 554R may be insertable or otherwise positioned in a selectable one of the apertures 554A to set a position of the outrigger 554A relative to the guide axis GA. The apertures 554A may be uniquely identified by indicia. The surgeon or clinical assistant may position the outrigger 554R in a selected one of the apertures 554A based on one or more settings or parameters specified in a surgical plan 33. Selection of the aperture 554A may be based on various parameters, such as a size and/or shape of the patient anatomy. In implementations, the outrigger 554R may be an elongated pin dimensioned to contact bone or other tissue at the surgical site. The outrigger 554R may be slidably received in a selected one of the apertures 554A to set a relative position of the outrigger 554R and guide body 562 with respect to the guide axis GA. In implementations, the surgeon may position two or more outriggers 554R in respective apertures 554A (see, e.g., outriggers 554R-1, 554R-2 of FIG. 23).

Figure 25:
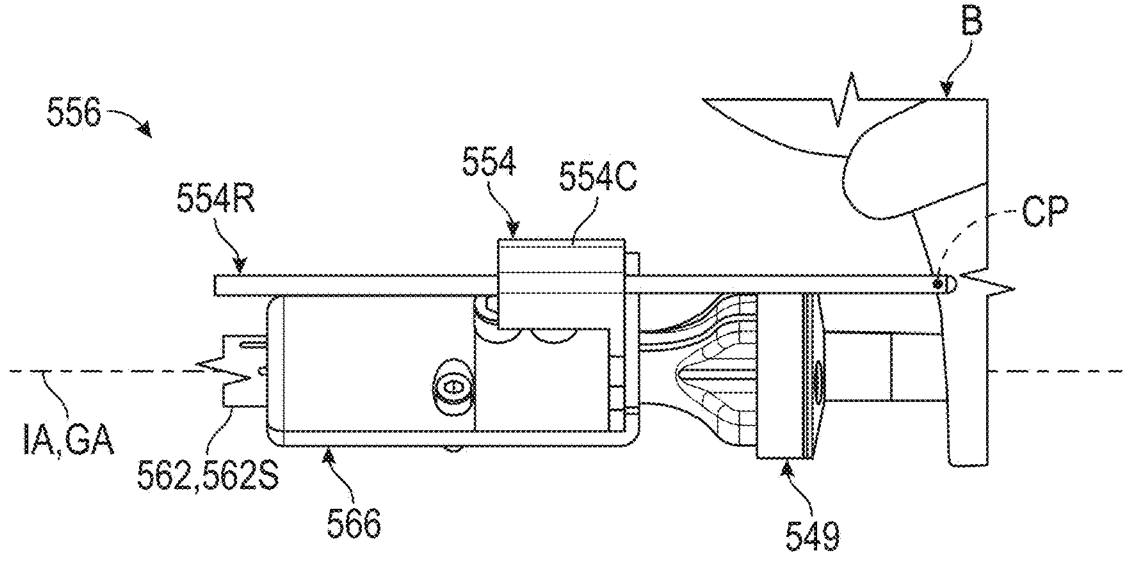
FIG. 25 illustrates a side view of the transfer guide of FIG. 22 at a first position relative to a bone.
Figure 26:
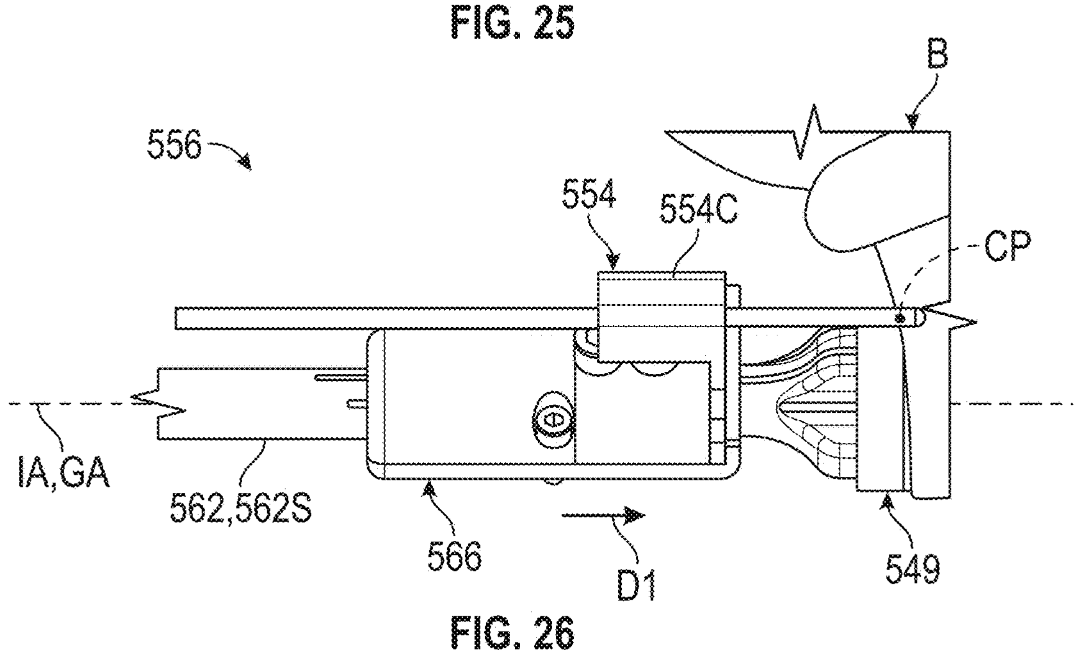
FIG. 26 illustrates a side view of the transfer guide of FIG. 22 at a second position relative to a bone.

Referring to FIGS. 25-26, the transfer guide 556 may be moveable in a first direction D1 toward a bone B to position an implant 549 against the bone B. The outrigger R may establish contact with the bone B at a respective contact point CP. The outrigger 554R may be slidably received within the carrier 554C such that the carrier 554C may slide or otherwise move along a length of the outrigger 554R in response to movement of the guide body 562 in the first direction D1 subsequent to establishing contact at the contact point CP.

Figure 27:
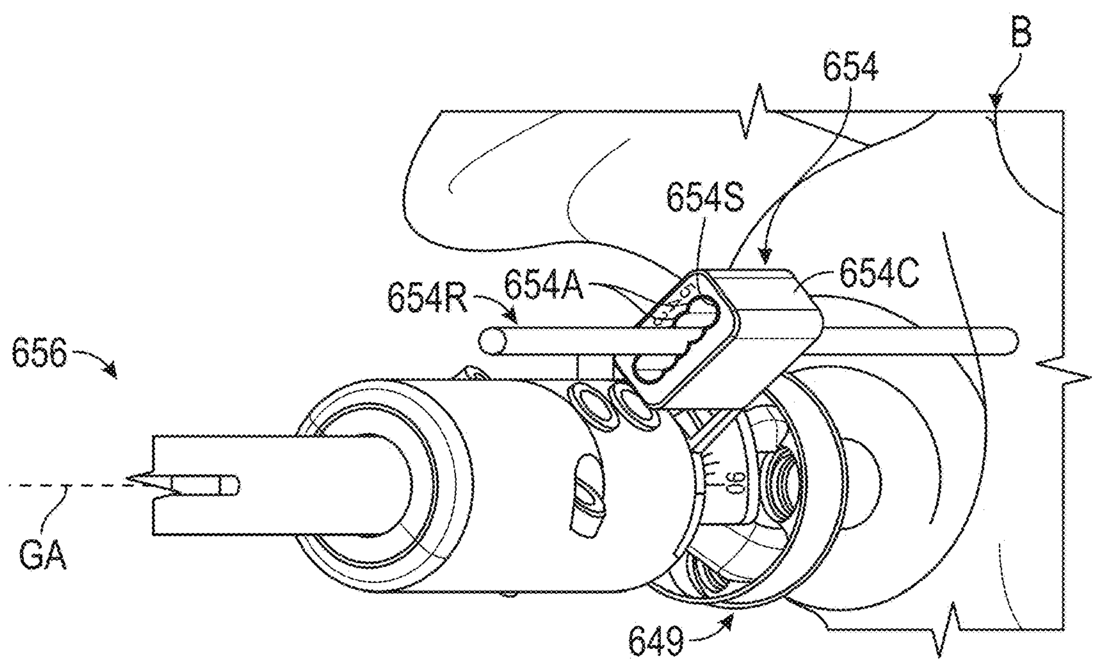
FIG. 27 illustrates a perspective view of a transfer guide coupled to an implant according to another implementation.
Figure 28:
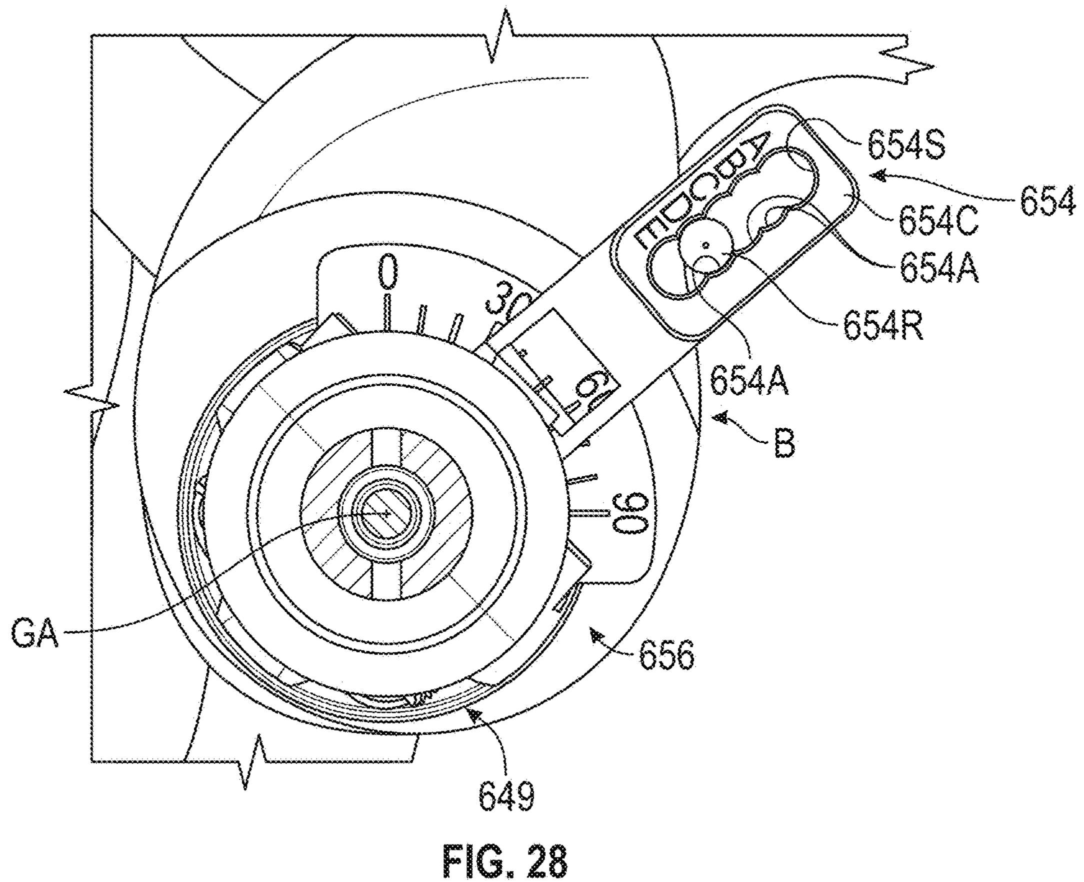
FIG. 28 illustrates a sectional view of the transfer guide of FIG. 27.

FIGS. 27-28 disclose a transfer guide 656 according to another implementation. The transfer guide 656 may include a transfer member 654 having a carrier 654C. The carrier 654C may include a plurality of apertures 654A dimensioned to receive an outrigger 654R. The apertures 654 may be dimensioned to at least partially overlap with each to establish a scalloped slot 654S. The slot 654S may provide the surgeon with improved precision and positioning of the outrigger 654R in a radial direction with respect to the guide axis GA. In implementations, the apertures 654A may be distributed in a column relative to the guide axis GA to establish the scalloped slot 654S.

Figure 29:
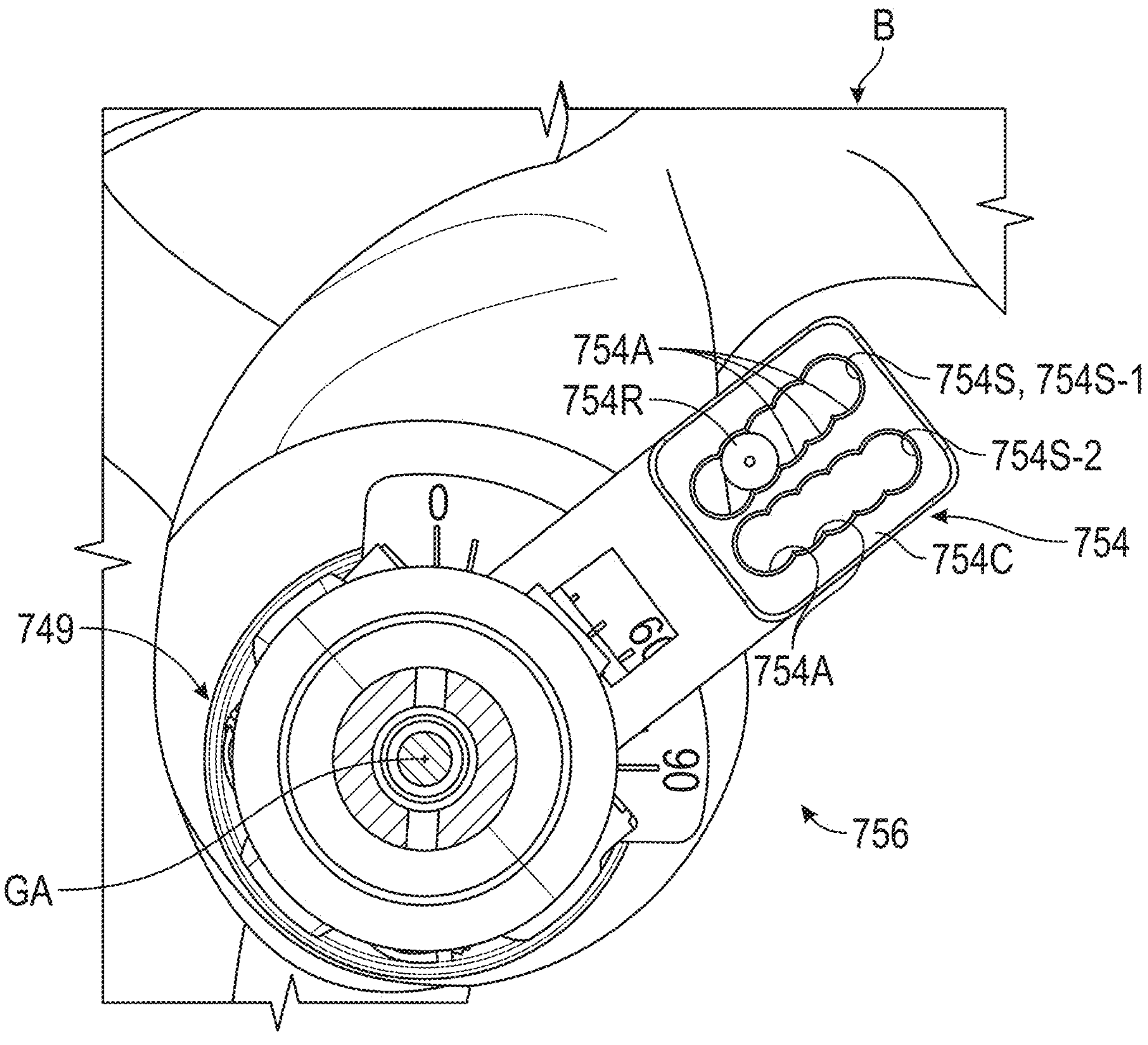
FIG. 29 illustrates a sectioned, axial view of a transfer guide according to another implementation.

In the implementation of FIG. 29, transfer guide 756 may include a carrier 754C having a plurality of slots 754S. The slots 754S may include a first slot 754S-1 and second slot 754-2 spaced apart from each other. Each of the slots 754S-1, 754S-2 may be established by a set of apertures 754A. The apertures 754A may at least partially overlap with each other to establish the respective slot 754S-1, 754-2. The slots 754S-1, 754S-2 may be circumferentially offset from each other relative to the guide axis GA. Each slot 754S may include apertures 754A circumferentially offset from each other to establish a variation in the circumferential direction relative to the guide axis GA. The slots 754S-1, 754S-2 may be dimensioned such that a circumferential spacing between the slots 754S-1, 754S-2 may diverge (e.g., increase or decrease) with respect to two or more radial positions of the slots 754S-1, 754S-2 relative to the guide axis GA.

Figure 30:
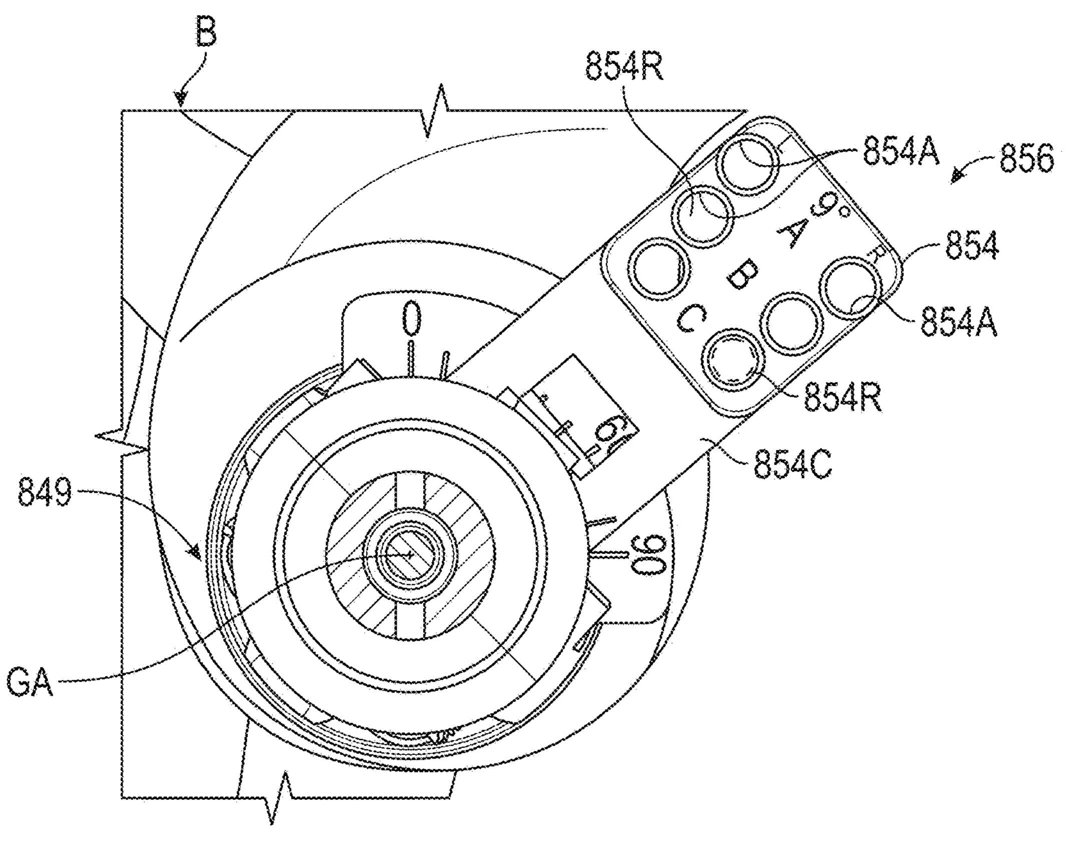
FIG. 30 illustrates a sectioned, axial view of a transfer guide according to another implementation.

In the implementation of FIG. 30, transfer member 854 may include a plurality of apertures 854A established along a carrier 854C. The apertures 854A may be spaced apart from each other along the carrier 854C. The apertures 854A may be arranged in one or more columns and rows relative to a guide axis GA of the transfer guide 856.

The transfer guides disclosed herein may be provided as a kit for an orthopaedic procedure. The kit may include at least one implant and/or a transfer guide including one or more transfer members, including any of the transfer guides disclosed herein such as the transfer guides 156/256/356/456/656/756/856 and/or implants 149/249/349/349'/549/649/749/849. The transfer members may include various shapes, sizes and configurations, including any of the transfer members disclosed herein. In implementations, the kit may include two or more implants that may differ in at least one dimension from each other (see, e.g., FIGS. 6 and 18). The implant may include a baseplate. The baseplate may include a main body and an anchor member. The anchor member may extend outwardly from the plate body. The anchor member may be securable to bone. In implementations, the implant may include an augment. The augment may extend along a rear face of the baseplate. The augment and/or another portion of the implant may be dimensioned with respect to a preoperative, patient-specific surface contour of the bone. In implementations, a rear face of the augment may substantially correspond to a surface contour of a respective bone. The baseplate and/or another portion of the implant may include a plurality of peripheral apertures. The peripheral apertures may be distributed about an axis of the implant. The implant may include an articulation member securable to the main body of the baseplate. The articulation member may include an articulation surface. The articulation surface may be configured to engage an articular surface of an opposed bone or implant.

The transfer guide may include an interface securable to the plate body of an implant selectable from the kit. The transfer guide may include at least one transfer member. In implementations, the kit may include two or more transfer members differing in at least one dimension from each other (see, e.g., FIG. 31). The transfer members may be interchangeable. Each transfer member may include a carrier and an outrigger. The outrigger may extend distally from the carrier such that the outrigger may be spaced apart from a periphery of the selected implant. The carrier may be rotatable about a periphery of the guide body to set a position of the outrigger. The outrigger may be configured to contact tissue to set an orientation of the baseplate relative to bone. The outrigger may be configured to set a position of the peripheral apertures of the implant relative to a guide axis of the transfer guide in response to contact with bone or other tissue.

Figure 31:
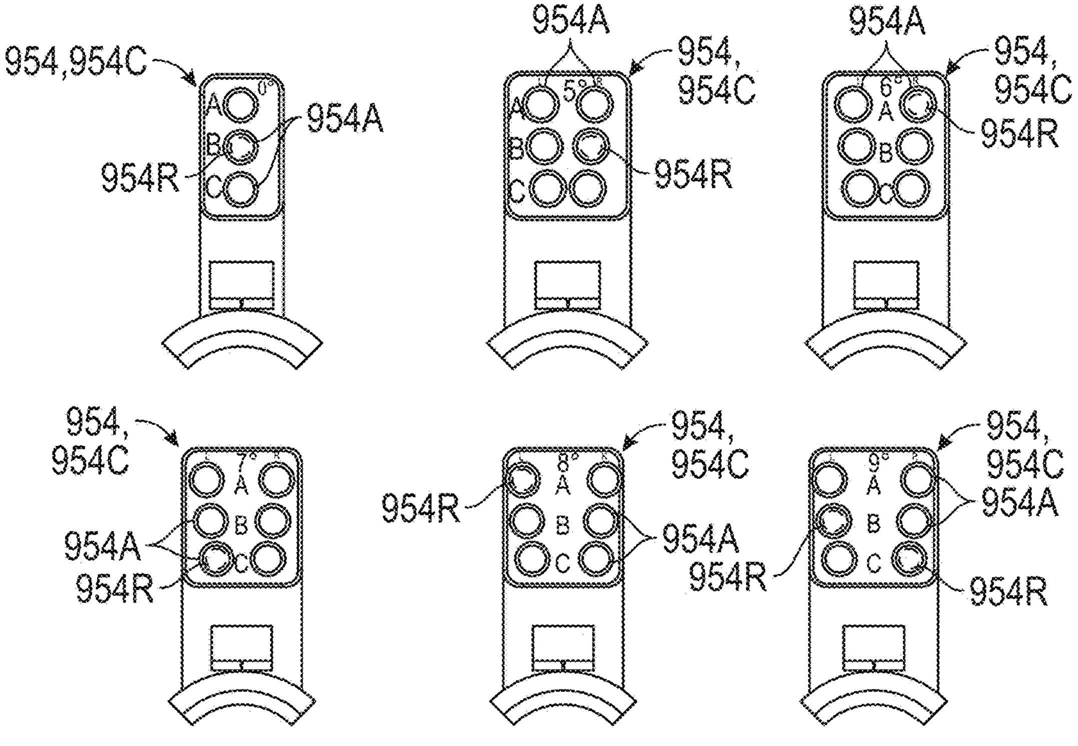
FIG. 31 illustrates transfer members including different dimensions and aperture distributions.

In implementations, the kit may include a set of transfer members releasably securable to the guide body (see, e.g., FIG. 31). The outrigger and carrier may be separate and distinct components. The carrier of each transfer member of the set of transfer members may include a plurality of apertures. The outrigger may be insertable in a selectable one of the apertures to set a position of the outrigger relative to the guide axis of the transfer guide. In implementations, the set of transfer members may be dimensioned such that a distribution of the apertures may differ for each transfer member of the set of transfer members. The apertures may be distributed utilizing any of the techniques disclosed herein.

FIG. 31 illustrates a set of transfer members 954 according to an implementation. The set of transfer members 954 may be interchangeable and may be releasably securable to the guide body of a respective transfer guide, such as the transfer guide 856 (FIG. 30). Each transfer member 954 may include a carrier 954C. The carrier 954C may be releasably secured to the guide body of a respective transfer guide, including any of the transfer guides disclosed herein, such as the transfer guide 854. Each of the carriers 954C may include one or more apertures 954A. The set of carriers 954C may be dimensioned such that a distribution of the apertures 954A may differ for each, or at least two, of the carriers 954C establishing the set of transfer members 954. The apertures 954A may be dimensioned to receive a common outrigger, such as the outrigger 854R of FIG. 30. The apertures 954A may be established at various circumferential and/or radial positions relative to the guide axis, providing the surgeon with fine increments to select from (e.g., approximately 1 to 9 degree increments). The surgeon or clinical assistant may select one of the transfer members 954 from the set of transfer members 954, which may improve accuracy in establishing a contact point associated with an orientation of the implant and/or other surgical device approved and/or otherwise specified in a surgical plan.

Figure 32:
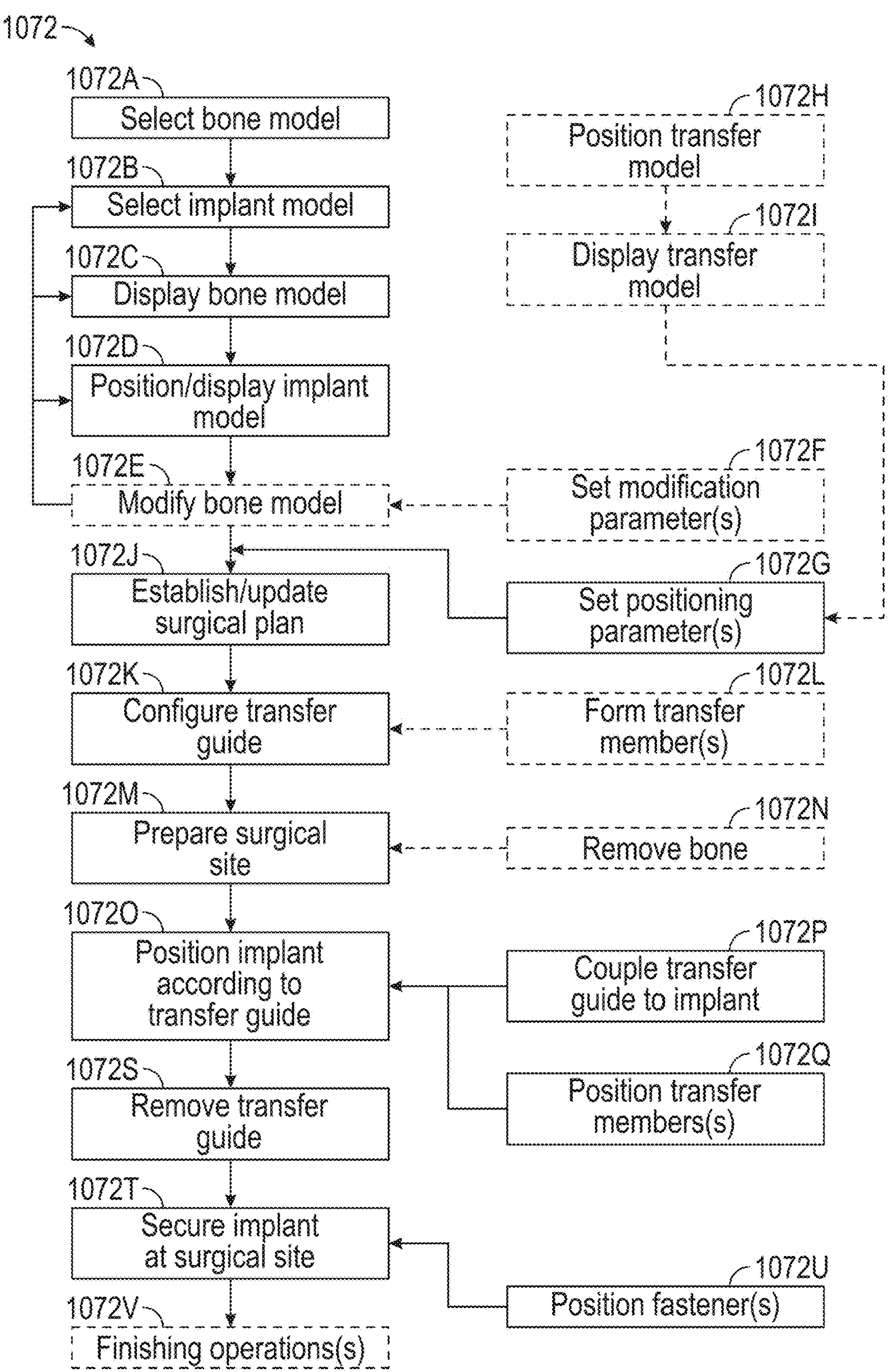
FIG. 32 illustrates a method of planning and implementing an orthopaedic procedure according to an implementation.

FIG. 32 illustrates an exemplary method of planning and implementing an orthopaedic procedure in a flowchart 1072. The method 1072 may be utilized pre-operatively, intra-operatively and/or post-operatively to create, edit, execute and/or review a respective surgical plan, including installing one or more orthopaedic implants. The method 1072 may be utilized to perform an arthroplasty for restoring functionality to shoulders and other joints. Although the method 1072 primarily refers to a shoulder reconstruction, it should be understood that the method and disclosed implants may be utilized in other locations of the patient and other surgical procedures, including any of the joints and procedures disclosed herein. The method 1072 may be utilized with any of the planning systems, assemblies, implants, transfer members, transfer guides, instruments and devices disclosed herein, including transfer guides 156, 256, 356, 456, 556, 656, 756 and/or 856. Fewer or additional steps than are recited below could be performed within the scope of this disclosure, and the recited order of steps is not intended to limit this disclosure. The planning system 20 and any of associated modules may be configured to execute each of the steps of the method 1072. Reference is made to the planning system 20 and graphical user interface 43 of FIGS. 2 and 3A-3C and the transfer guide 356 of FIGS. 12-19 for illustrative purposes.

Referring to FIG. 2, with continuing reference to FIG. 32, bone model(s) 31 may be selected from one or more bone models 31 by interacting with the user interface 43 at step 1072A. An implant model 32 may be selected from one or more implant models 32 by interacting with the user interface 43 at step 1072B. Available bone models 31, implant models 32 and surgical plans 33 in the database(s) 29 may be presented in one or more lists in the user interface 43 and may be selected in response to user interaction. The selected bone model 31 may correspond to a bone associated with a shoulder or other joint, such as a humeral head of a humerus (e.g., FIG. 3A) or a glenoid (e.g., FIG. 3B). A selected one of the bone models 31 may be initially positioned and displayed in one or more windows 44 of the user interface 43 at step 1072C. Each selected bone model 31 and selected implant model 32 may be displayed in the display window(s) 44 according to any of the techniques disclosed herein, including different orientations and 2D/3D views.

The selected implant model 32 may be positioned relative to the selected bone model 31 at step 1072D. Step 1072D may include automatically positioning the implant model 32 relative to the bone model 31 based on one or more predetermined parameters or settings and/or landmarks associated with the selected bone model 31. Step 1072D may include moving the selected implant model 32 relative to the selected bone model 31 in response to user interaction with the user interface 43. A position of the selected implant model 32 may be adjusted in one or more iterations prior to, during and/or subsequent to any of the steps of method 1072.

One or more modifications to the selected bone model 31 may be made at step 1072E. The modifications may be made in response to user interaction with the user interface 43. Step 1072E may include setting one or more modification parameters at step 1072F. The modification parameters may include a resection angle ($\alpha$) and/or resection plane RP associated with the resection angle ($\alpha$) (FIG. 3A). The resection angle ($\alpha$) may be established relative to an axis AB of the respective bone model 31. Step 1072F may include selecting a resection angle ($\alpha$) to define a resection plane RP along the selected bone model 31. Step 1072F may include selecting a position, orientation and dimension of an aperture BA along the bone B (see, e.g., FIG. 33). The aperture BA may be associated with a respective aperture BA established in a volume of the selected bone model 31 (see, e.g., FIG. 3B). The modification parameters may be stored in the respective surgical plan 33. Step 1072D may include positioning the selected implant model 32 along the resection plane RP and/or at least partially within the aperture BA such that a volume of the selected implant model 32 may be at least partially received in a volume of the selected bone model 31 (see, e.g., FIGS. 3A-3B).

Figure 33:
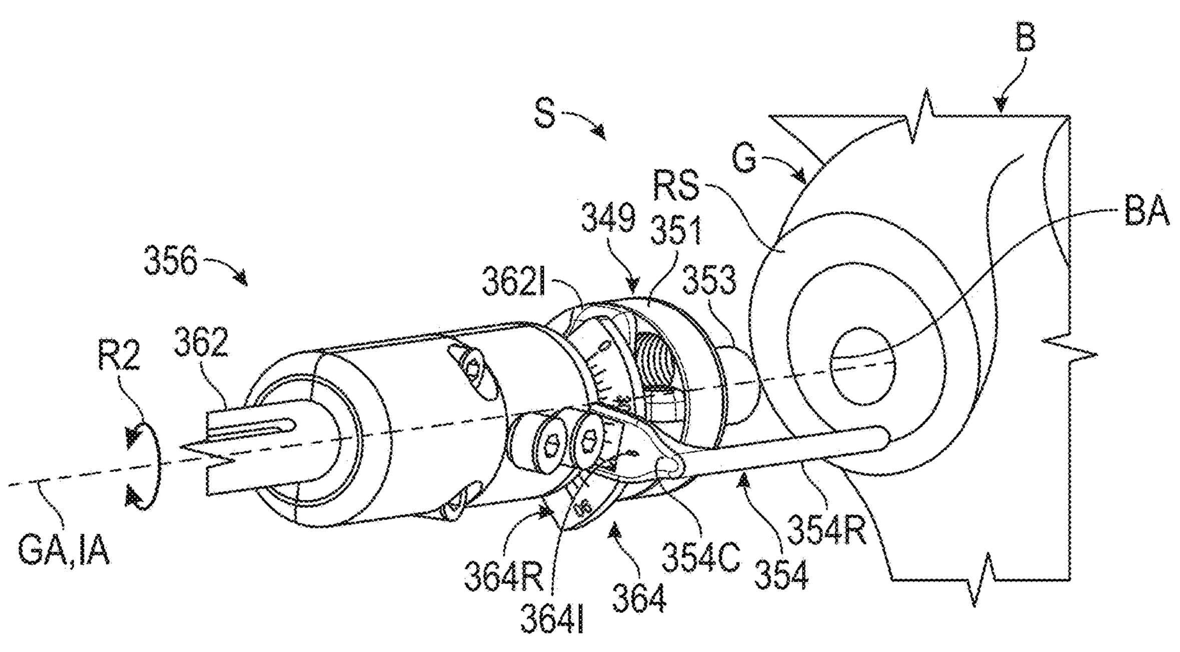
FIG. 33 illustrates the transfer guide and implant of FIG. 12 positioned relative to a surgical site.

Referring to FIGS. 2 and 3A-3B, with continuing reference to FIG. 32, at step 1072G one or more positioning parameters may be set relating to the transfer model 48 and associated transfer member(s), such as the transfer member 354 (see, e.g., FIG. 33). The positioning parameters may include any of the parameters disclosed herein, including one or more settings or dimensions associated with the transfer model 48. The parameters may be generated or set based on a virtual position VP, virtual axis VA and/or one or more contact points CP. The settings and dimensions may be communicated utilizing various techniques. Step 1072G may include storing the settings and/or dimensions in one or more records 41 in the database 29 associated with the respective transfer model 48. In implementations, step 1072G may include displaying the settings and/or dimensions in one or more graphics in the user interface 43 and/or storing the settings and/or dimensions in an output file.

Step 1072G may include displaying a geometry of the selected transfer model 48 in one or more display windows 44 of the user interface 43 at step 1072I (see, e.g., FIG. 3B). Step 1072G may include positioning the geometry of the transfer model 48 relative to a geometry of the selected bone model 31 and/or implant model 32 at step 1072H. Step 1072H may include determining the position of one or more portions of the transfer model 48 relative to the selected bone model 31 and/or implant model 32, including a surface contour associated with the selected bone model 31. Step 1072G may include situating the transfer model 48 at a specified orientation and/or position relative to the selected bone model 31 and/or selected implant model 32 such that a portion of the selected transfer model 48 contacts a surface contour of the selected bone model 31 and/or selected implant model 32 (see, e.g., FIG. 3B). Step 1072H may including positioning the transfer member(s) 54 associated with the selected transfer model 48 such that the transfer member(s) 54 may contact the surface contour of the selected bone model 31 at a respective contact point CP. The contact point CP may be associated with a circumferential and/or radial position of the transfer member 354 relative to the guide axis GA of the transfer guide 356 (see, e.g., FIG. 33).

At step 1072J, a surgical plan 33 may be established and/or updated according to the selected bone model 31, selected implant model 32, and selected transfer model 48 at step 1072E and/or according to the parameters and settings determined at step 1072F and/or step 1072G. Step 1072J may include updating a local instance of the surgical plan 33 and/or updating the surgical plan 33 in the database 29. One or more iterations of the step(s) of the method 1072 may be performed to update the surgical plan 33. The surgical plan 33 may be based on a surface profile of a bone associated with the selected bone model 31. The surgical plan 33 may include at least one or more dimensions, settings or other parameters associated with one or more transfer members 354 relative to the surface profile of the bone, which may be determined at step 1072G. The dimensions may include patient-specific information and may include a length, width and/or surface profile of the outrigger 354R associated with a respective contact point CP. Method 1072 may include one or more steps to implement a predetermined surgical plan, such as a surgical plan 33 previously established and/or updated at step 1072J.

Referring to FIG. 33, with continuing reference to FIG. 32, at step 1072K the surgeon or clinical assistant may configure the transfer guide 356. The transfer guide 356 may include a guide body 362 extending along a guide axis GA and at least one transfer member 354 coupled to the guide body 362. The transfer member 354 may include a carrier 354C and an outrigger 354R. The outrigger 354R may extend distally from the carrier 354C relative to the guide axis GA. The transfer guide 356 may include an alignment mechanism 364 for indicating a position of the transfer member 354. The alignment mechanism 364 may be established according to any of the techniques disclosed herein. The alignment mechanism 364 may configured to indicate a circumferential position of the outrigger 354R relative to the guide axis GA. The alignment mechanism 364 may include a ruler 364R and an indicator 364I adjacent the ruler 364R. In implementations, the indicator 364I may be established along the carrier 354C.

The transfer guide 356 may be associated with a respective transfer model 48 and surgical plan 33. Step 1072K may include transferring or otherwise communicating one or more parameters associated with the transfer model 48 including one or more settings, dimensions and/or other parameters determined at step 1072G or otherwise specified in the surgical plan 33.

Step 1072K may include configuring the transfer guide 356 according to one or more settings or parameters communicated or otherwise specified in the surgical plan 33. Step 1072K may include forming one or more transfer members associated with the selected transfer model 48 at step 1072L, including any of the transfer members disclosed herein such as the transfer member 354. Exemplary techniques for forming the transfer members may include injection molding, casting printing and machining techniques. Step 1072L may include forming one or more portions of the transfer member 354 according to a patient-specific surface contour of the patient anatomy. The virtual position VP, virtual axis VA and/or contact points CP and associated dimensions, settings and other parameters established at step 1072G may be utilized as design constraints in the design and formation of a physical instance of the transfer model 48 and respective transfer member(s) 354, implant 349 and/or transfer guide 356. Step 1072K may occur prior, during and/or subsequent to initially positioning the implant 349 relative to bone B. The bone B may be a portion of a glenoid G, as illustrated in FIGS. 32-39, or another bone or joint of the patient anatomy, such as a humerus.

Configuring the transfer guide 356 at step 1072K may include rotating or otherwise moving the carrier 354C about a periphery of the guide body 362 to set an orientation of the outrigger 354R relative to the guide axis GA. Step 1072K may include moving the transfer member 354 between a first position and a second position relative to the guide body 362 based on at least one parameter of a preoperative plan, such as a surgical plan 33.

Various techniques may be utilized to establish the position of the transfer member 354. The orientation of the outrigger 354R may be set according to a position of the indicator 364I relative to the ruler 364R. In implementations, the surgeon or clinical assistant may move the indicator 364I in a second rotational direction R2 relative to the guide axis GA to set a position of the indicator 364I relative to the ruler 364R. The indicator 364I may be aligned with a selected position or value along the ruler 364R. The selected position along the ruler 364R may be associated with one or more settings or parameters determined for the respective transfer model 48 at step 1072G or otherwise specified in a respective surgical plan 33 at step 1072J.

In the implementations of FIGS. 22-26, 27-28, 29, 30 and 31, the carrier 554C/654C/754C/854C/954C may include at least one or more apertures 554A/654A/754A/854A/954A. The apertures 554A/654A/754A/854A/954A may be distributed in a radial direction and/or circumferential direction relative to the guide axis GA. Configuring the transfer guide 556/656/756/856 at step 1072K may include inserting a selected outrigger 554R/654R/754R/854R/954R through a selected one of the apertures 554A/654A/754A/854A/954A to set a position of the outrigger 654R/754R/854R/954R relative to the guide axis GA (see, e.g., FIGS. 22-23, 27-28, 29 and 30).

Referring again to FIG. 33, with continuing reference to FIG. 32, implementing the surgical plan 33 may include preparing a surgical site S at step 1072M. Step 1072M may occur prior to placement of the selected implant 349. Step 1072M may include removing a portion of the bone B at step 1072N. Various techniques may be utilized to remove the portion of bone B, such as a cutting, reaming, drilling, milling and/or punching operation. Step 1072N may include resecting a portion of the bone B, such as along an articular surface of the glenoid G to establish a resection surface RS. Step 1072N may include forming an aperture BA along the bone B. The aperture BA may be established along an articular and/or non-articular surface of the bone B, such as along the articular surface of the glenoid G. The aperture BA may extend inwardly from the resection surface RS. Step 1072N may occur according to the modification parameter(s) specified at step 1072F.

Implementing the respective surgical plan 33 may include installing one or more orthopaedic implants, such as the implant 349. The implant 349 may be installed along the bone B or other tissue at a surgical site S. The bone B may be associated with a respective bone model 31 (FIG. 2). The implant 349 may be associated with a respective implant model 32 specified in the surgical plan 33 (FIG. 2). The implant 349 may include a baseplate 351 and an alignment member (e.g., anchor member or stem) 353. The alignment member 353 may extend outwardly from the baseplate 351. In implementations, the alignment member 353 may extend along an axis of the baseplate 351, which may establish the implant axis IA.

The surgeon may position the transfer guide 156 together with the implant 349 at step 1072O. Step 1072O may include coupling the transfer guide 356 and selected implant 349 to each other at step 1072P. Various techniques may be utilized to couple the transfer guide 356 and implant 349 to each other, including any of the techniques disclosed herein. The selected implant 349 may be coupled to the interface portion 362I of the transfer guide 356.

Figure 33A:
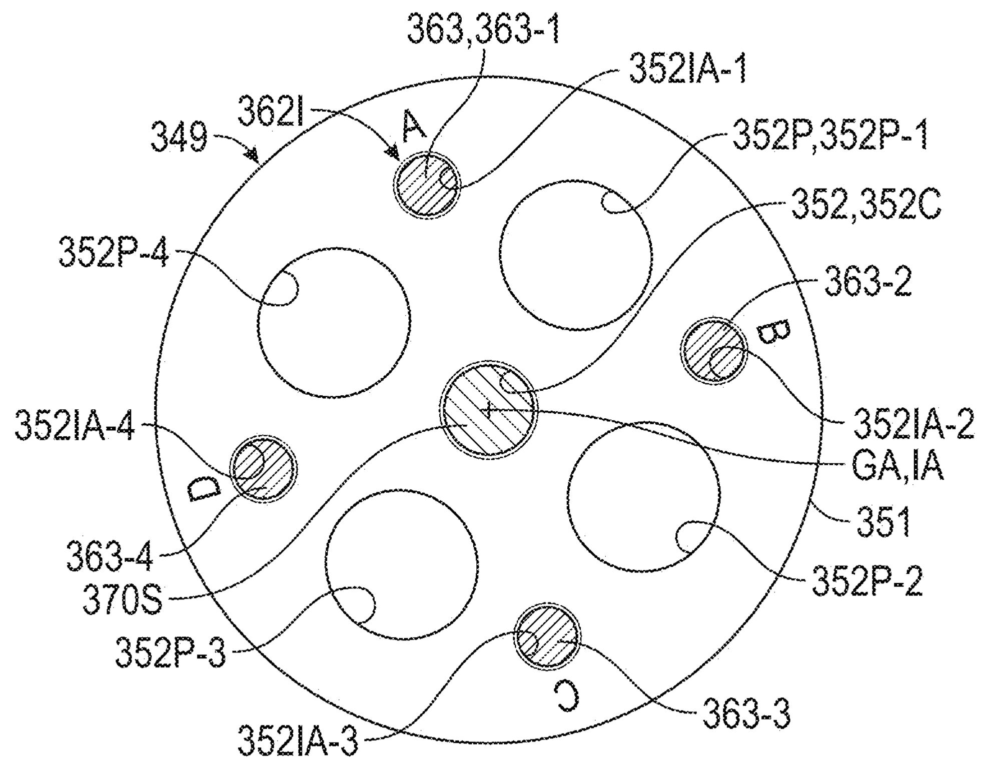
FIG. 33A illustrates a first configuration established by the transfer guide and implant of FIG. 33.
Figure 33B:
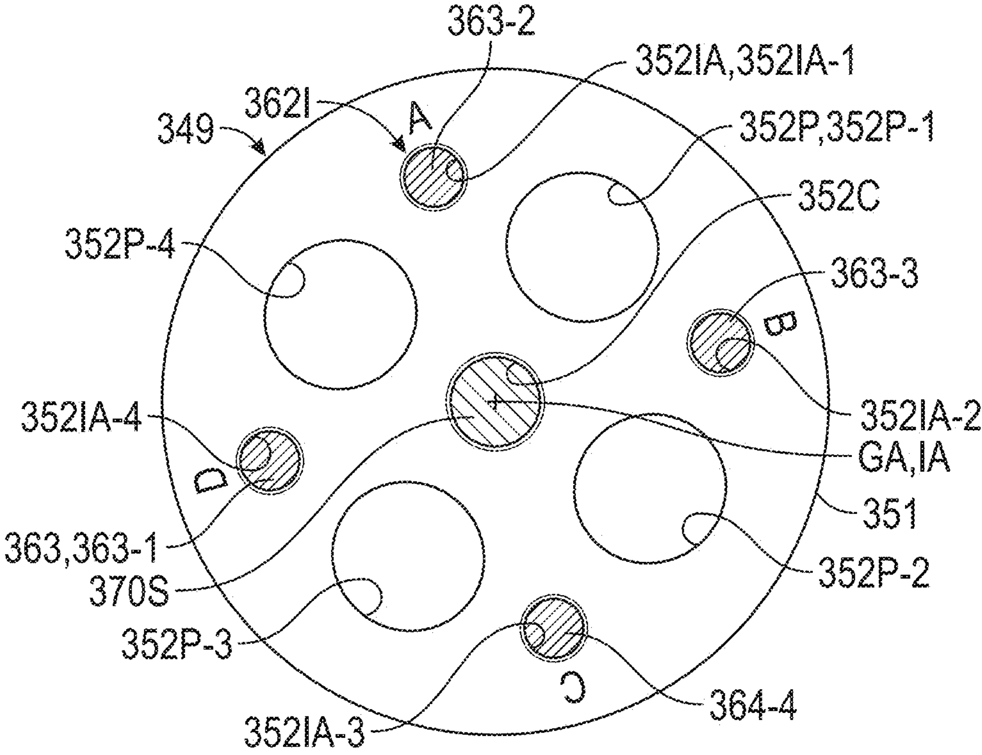
FIG. 33B illustrates a second configuration established by the transfer guide and implant of FIG. 33.

Referring to FIGS. 33A-33B, with continuing reference to FIGS. 32-33, the transfer guide 356 may include a plurality of protrusions 363 (see also FIG. 13). The protrusions 363 may be an array of protrusions 363 circumferentially distributed about the guide axis GA. The implant 349 may include an array of insertion apertures 352IA circumferentially distributed about the implant axis IA. Coupling the transfer guide 356 and the selected implant 349 together may include inserting the protrusions 363 into respective ones of the insertion apertures 352IA at the interface 362I to set the orientation of the implant 349 relative to the transfer guide 356 based on at least one parameter of the surgical plan 33.

Step 1072P may include inserting the protrusions 363 of the transfer guide 356 into the selected interface apertures 352IA to set a circumferential position of the implant 349 relative to the guide axis GA. The selection may be specified by one or more parameters of the surgical plan 33. The parameters may include specified pairings of the protrusions 363 and interface apertures 352IA. Each protrusion 363 may be associated with two or more distinct pairings. Each protrusion 363 may be paired with two or more different interface apertures 352IA to establish a respective orientation of the implant 349 relative to the guide axis GA. The transfer guide 356 and selected implant 349 may cooperate to establish a plurality of configurations associated with relative orientations between the transfer guide 356 and implant 349.

In the implementation of FIG. 33A, the transfer guide 356 and implant 349 may cooperate to establish a first configuration. The first configuration may be established by mating the protrusions 363-1 to 363-4 with the respective interface apertures 352IA-1 to 352IA-4 to position the peripheral apertures 352P-1 to 352P-4 circumferentially relative to the guide axis GA. In the implementation of FIG. 33B, the transfer guide 356 and implant 349 may cooperate to establish a second configuration. The second configuration may be established by mating the protrusions 363-1 to 363-4 with the respective interface apertures 352IA-4, 363IA-1, 363IA-2, 363IA-3 to position the peripheral apertures 352P-1 to 352P-4 circumferentially relative to the guide axis GA. Configuring the transfer guide 356 to establish two or more configurations may be utilized to provide a first (e.g., coarse) circumferential setting. Configuring the transfer member 354 may be utilized to provide a second (e.g., fine) circumferential setting. The surgeon or clinical assistant may configure the transfer guide 356 to configure and position the transfer guide 356 in a precise and reproduceable manner.

Step 1072P may include mechanically attaching or releasably securing the transfer guide 356 to the implant 349. The guide body 362 may be arranged to interface with the implant 349. Step 1092P may include mechanically attaching the transfer guide 356 and implant 349 at a connection. Step 1072P may include mechanically attaching the transfer guide 356 and implant 349 to each other at a threaded connection established by the shaft 370S and central aperture 352C (see also FIGS. 18-19). Mechanically attaching the transfer guide 356 and implant 349 to each other may occur subsequent to inserting the protrusions 363 of the transfer guide 356 into the selected interface apertures 352IA to set a circumferential position of the implant 349 relative to the guide axis GA.

Figure 34:
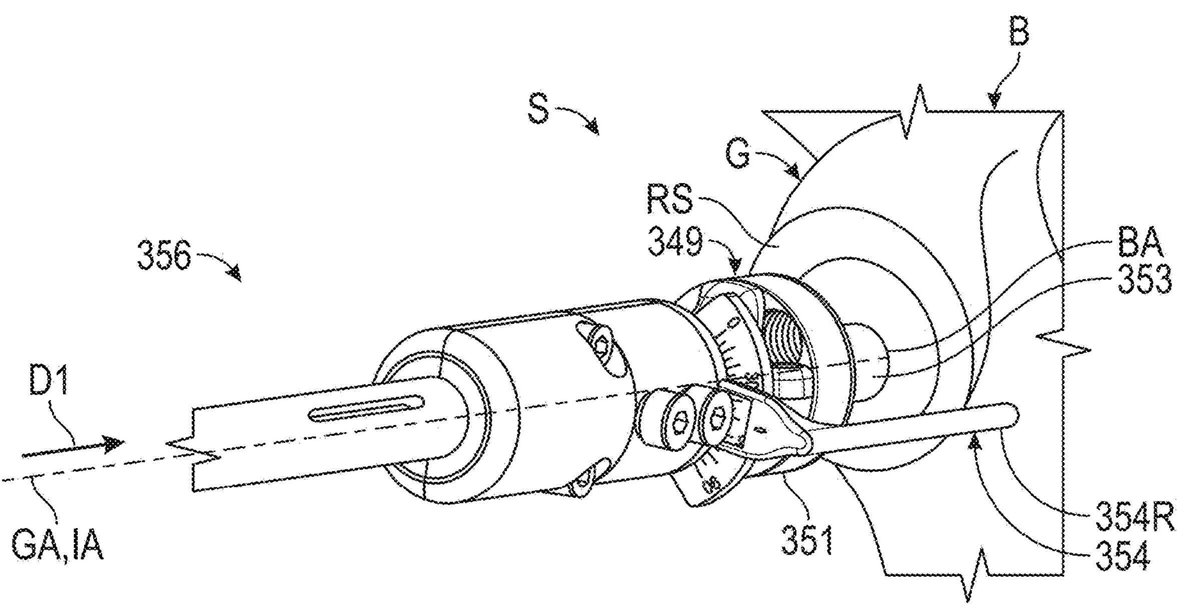
FIG. 34 illustrates the transfer guide and implant at a first position relative to a bone at the surgical site of FIG. 33.

Referring to FIG. 34, with continuing reference to FIGS. 32-33, the selected implant 349 may be positioned according to the transfer member(s) 354. Step 1072O may include positioning the implant 349 relative to the bone B based on a position of the transfer member(s) 354 relative to the guide axis GA. Step 1072O may include moving the transfer guide 356 and implant 349 as a unit in the first direction D1 towards the bone B. The surgeon may position the alignment member 353 of the implant 349 at least partially into the aperture BA to limit translation and other movement of the implant 349 relative to the bone B.

Figure 35A:
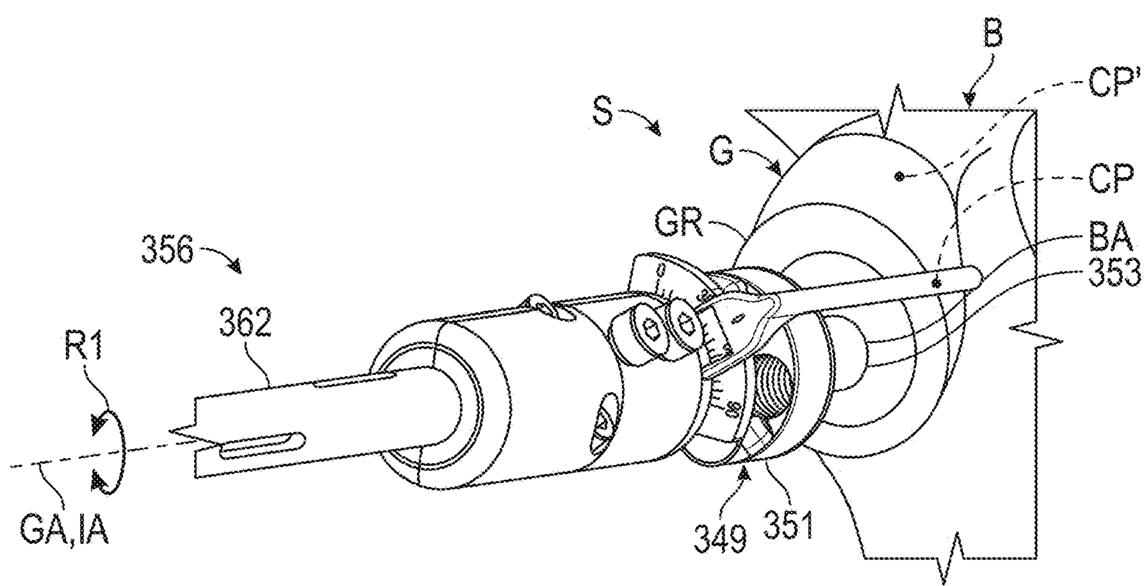
FIGS. 35A-35B illustrate the transfer guide and implant at a second position relative to the bone at the surgical site of FIG. 33.
Figure 35B:
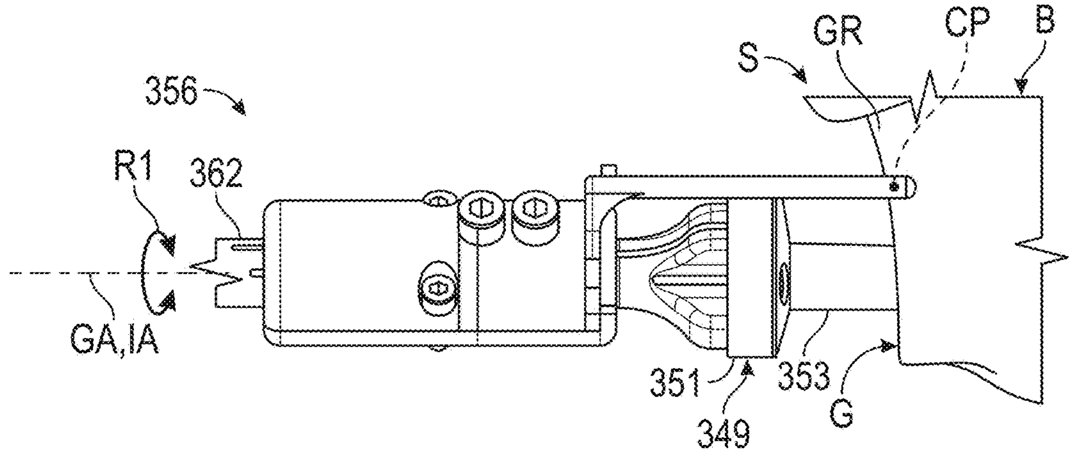

Referring to FIGS. 35A-35B, with continuing reference to FIGS. 32 and 34, step 1072O may include positioning the transfer member(s) 354 to contact the bone B or other tissue adjacent the surgical site S at step 1072Q. Step 1072Q may occur during and/or subsequent to positioning the alignment member 353 at least partially into the aperture BA. The surgeon may move the transfer guide 356 to establish contact between the outrigger 354R and bone or other tissue to set an orientation of the transfer guide 356 and implant 349 relative to the bone B. Step 1072O may include rotating the transfer guide 356 and the implant 349 together as a unit in the first rotational direction R1 about the guide axis GA and/or implant axis IA such that the outrigger 354R establishes contact with the bone B at a respective contact point CP. The contact point CP may be established at a terminal end portion of the outrigger 354R (see, e.g., FIG. 35B) or may be established along an intermediate portion of the outrigger 354R such that a distal portion of the outrigger 354R may overhang the bone B (see, e.g., FIG. 7).

Step 1072Q may occur such that the transfer member 354 may limit rotational and/or translational movement of the implant 349 relative to the bone B. Step 1072Q may occur such that the transfer member 354 may fix or set a position and/or orientation of the implant 349 relative to the bone B, which may correspond to the parameter(s) established at step 1072G, including a predetermined virtual position VP, virtual axis VA and/or contact point(s) CP of the respective transfer model 48 and implant model 32 associated with the surgical plan 33. Step 1072O may occur such that the implant axis IA may be substantially aligned with the virtual position VP and virtual position VA of the respective implant model 32 (see, e.g., FIG. 3C).

The contact point(s) CP may be predetermined prior to positioning the transfer guide 356 at the surgical site S utilizing any of the techniques disclosed herein. The contact points CP may be defined according to the surgical plan 33 and may be established along a surface of the bone B, including along an articular surface or non-articular surface of a joint. The contact points CP may correspond to one or more landmarks defined by the patient anatomy, such as a glenoid rim GR of the glenoid G. In the implementation of FIGS. 35A-35B, a contact point CP may be established along an anterior-superior region of the glenoid rim GR. In other implementations, a contact point CP may be established along another region of the glenoid rim RM, such as along a posterior-superior region of the glenoid rim GR (see, e.g., FIG. 55).

Each contact point CP may be a single point or a localized region along the bone B or other tissue. The transfer members 354 may be configured according to the parameters or settings from the surgical plan 33 such that the outrigger 354R may establish contact at only one predetermined position along the bone B or tissue in the vicinity of the predetermined contact point CP to situate the implant 349 at the predetermined position and/or orientation specified in the surgical plan 33. The contact point CP may be established along a non-articular surface of the bone B (see, e.g., FIG. 35B) or may be established along an articular surface of the bone B (see, e.g., contact point CP' of FIG. 35A).

Figure 36:
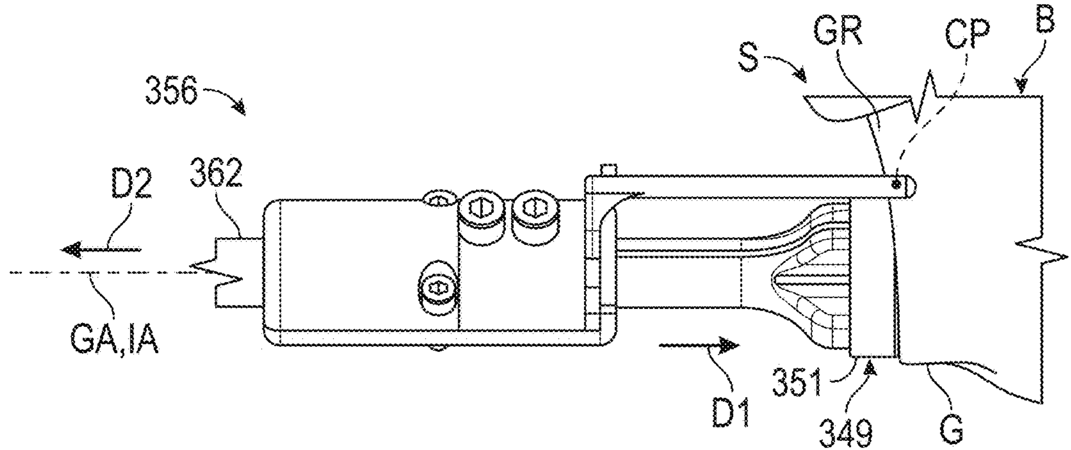
FIG. 36 illustrates the transfer guide and implant at a third position relative to the bone at the surgical site of FIG. 33.

Referring to FIG. 36, with continuing reference to FIG. 32, step 1072O may include seating or otherwise positioning the implant 349 in contact with the bone B. The implant 349 may be oriented relative to the bone B based on the orientation of the transfer guide 356 established by the outrigger 354R at the contact point CP with respect to the guide axis GA and/or implant axis IA. The anchor member 353 may be press fit or otherwise inserted in the aperture BA. The surgeon may move the guide body 362 of the transfer guide 356 and the implant 349 together as a unit in the first direction D1 to impact the anchor member 353 in the aperture BA (see FIG. 35A) and seat a rear surface of the implant 349 against a surface of the bone B. In other implementations, the implant 349 may be positioned in contact with the bone B prior to coupling the implant 349 and transfer guide 356 to each other. The rear surface of the implant 349 may be established by the baseplate 351. Step 1072O may occur such that the rear surface of the implant 349 may contact an articular and/or non-articular surface of the bone B, such as an articular surface of the glenoid G. The rear surface of the implant 349 may include a non-patient specific surface and/or may include a patient-specific surface dimensioned to substantially follow a surface contour of the bone B based on the predetermined surgical plan 33 (see, e.g., FIG. 18).

Seating the implant 349 may occur such that the circumferential position of each of the peripheral apertures 352P relative to the guide axis GA may substantially correspond to one or more parameters or settings specified in a surgical plan 33. The circumferential position of each of the peripheral apertures 352P may be established by contact between the outrigger 354R and the bone B or other tissue at the contact point CP.

Figures 37, 38:
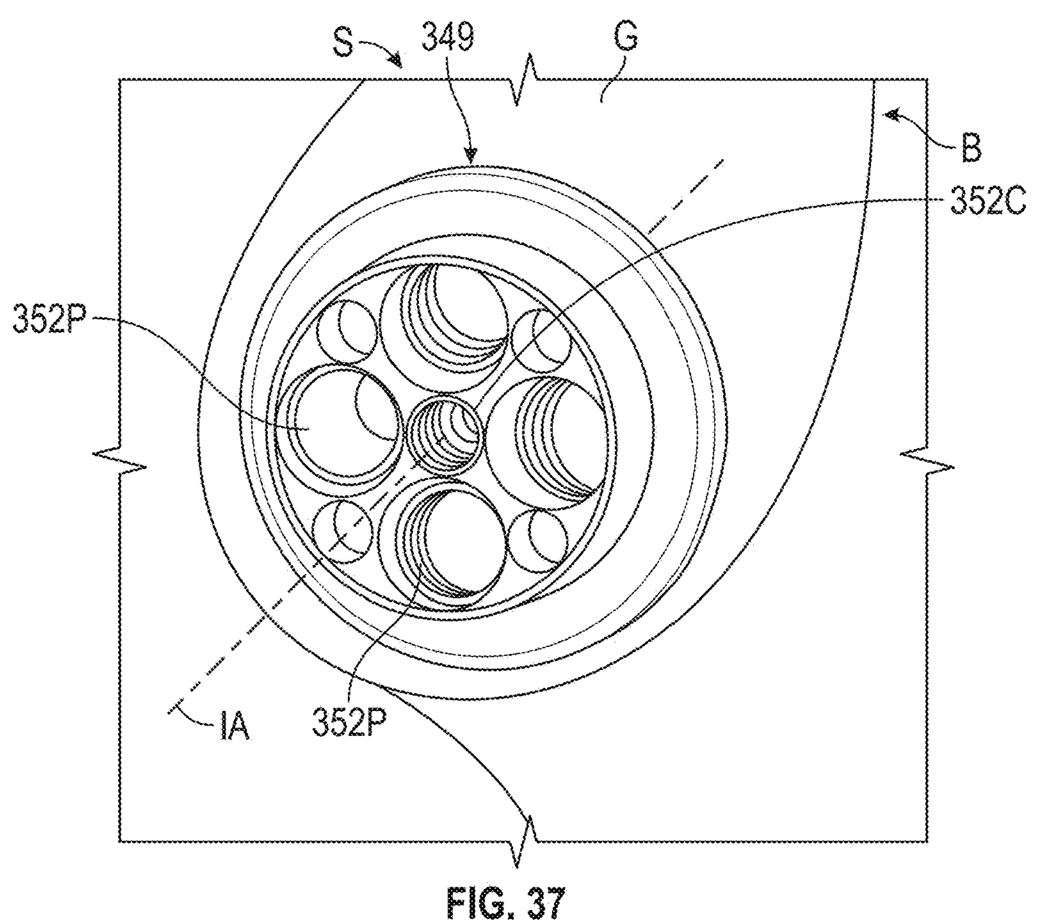
FIG. 37 illustrates the implant of FIG. 36 with the transfer guide removed from the surgical site.
FIG. 38 illustrates fasteners positioned relative to the implant of FIG. 37.

Referring to FIGS. 36-37, with continuing reference to FIG. 32, the transfer guide 356 may be removed from the implant 349 at the surgical site S at step 1072S. Step 1072S may include moving the transfer guide 356 in a second direction D2 away from the bone B (FIG. 36). In the implementation of FIGS. 17-19, step 1072S may include moving the actuator 370A in the third rotational direction R3 to decouple the coupling shaft 370S and the implant 349' from each other.

Figure 39:
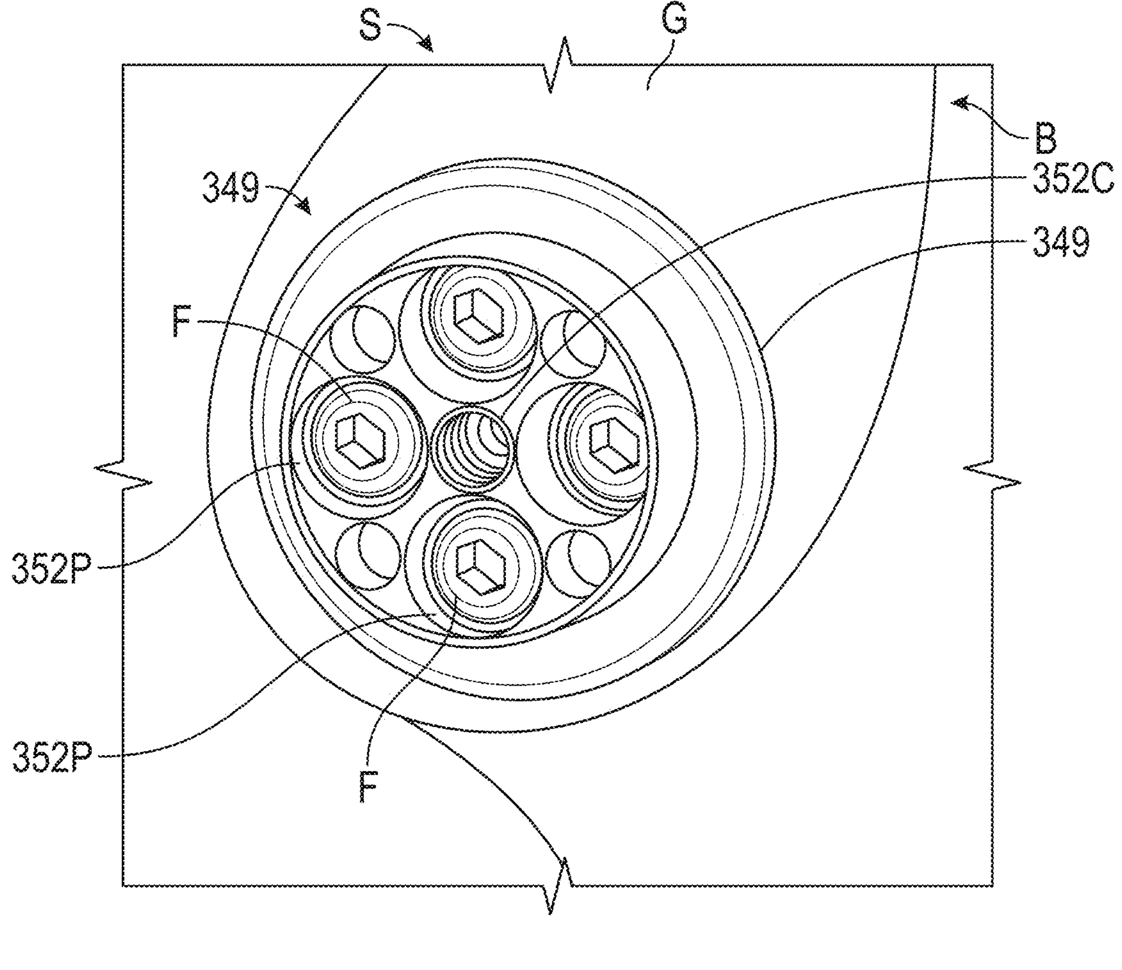
FIG. 39 illustrates the fasteners positioned in respective apertures of the implant of FIG. 38.

Referring to FIGS. 38-39, the implant 349 may be secured to the bone B at the surgical site S at step 1072T. Various techniques may be utilized to secure the implant 349. Step 1072T may include positioning one or more fasteners F in respective peripheral apertures 352P and then into the bone B to secure the implant 349 at the surgical site S at step 1072U. Securing the implant 349 at step 1072T may occur subsequent to positioning the implant 349 based upon a position of the outrigger 354R at step 1072O. The fasteners F may include any of the fasteners disclosed herein, such as compression screws.

At step 1092V, one or more finishing operations may be performed at the surgical site S. Step 1092V may include coupling an articulation member to the baseplate (see, e.g., FIG. 3B). The articulation member may include an articulation surface dimensioned to cooperate with an adjacent bone or implant. The articulation surface may have various geometries including a generally concave or convex geometry. Step 1092V may include closing an incision made in the patient to situate the implant 349.

Figure 40:
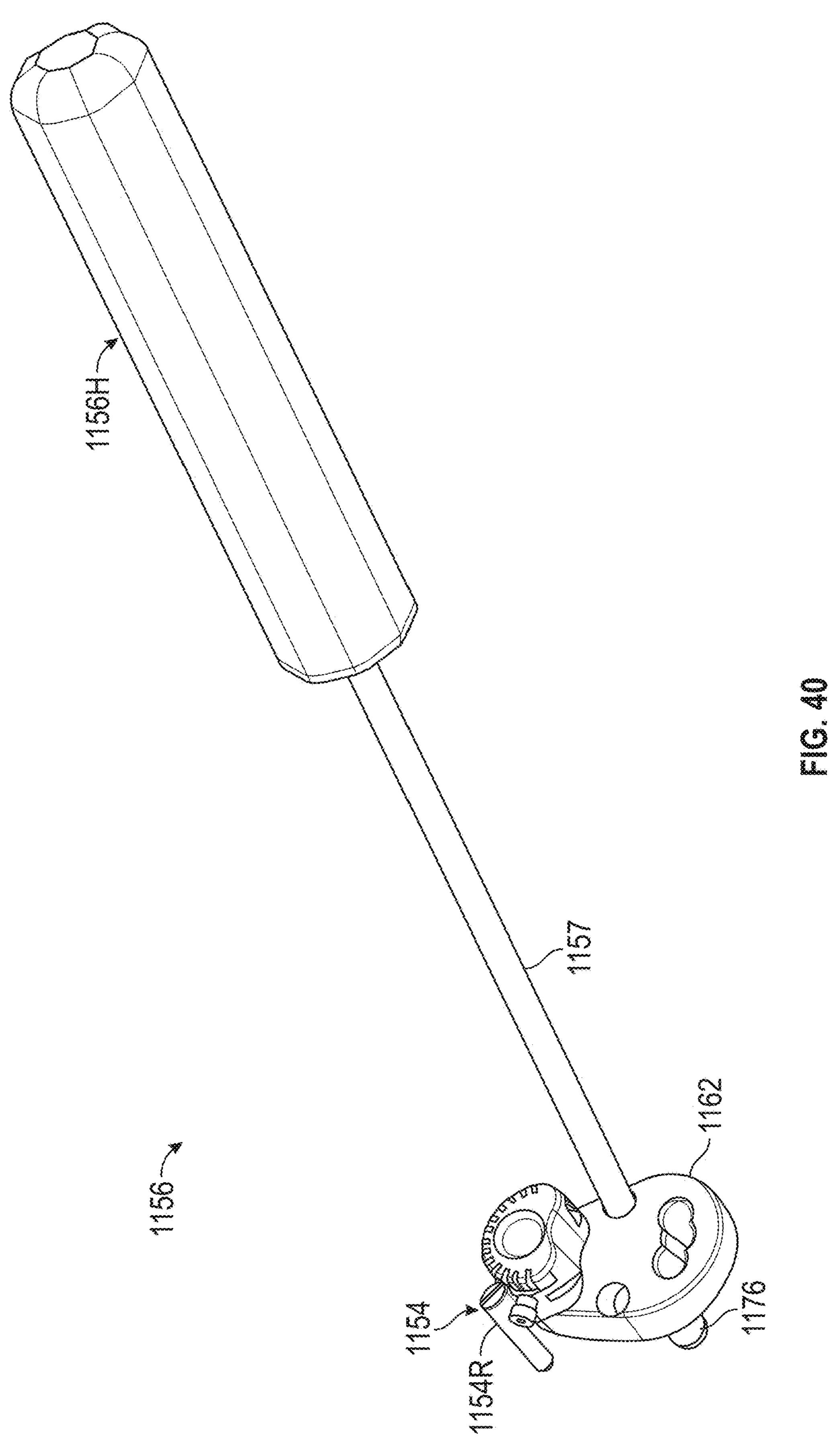
FIG. 40 illustrates a perspective view of a transfer guide according to another implementation.

FIG. 40 discloses a transfer guide 1156 for an orthopedic procedure according to an implementation. The transfer guide 1156 may be utilized to position one or more surgical devices relative to the patient anatomy. The transfer guide 1156 may be utilized to position various surgical devices, including any of the surgical devices disclosed herein.

The transfer guide 1156 may include a guide body 1162. A shaft 1157 may interconnect the guide body 1162 and a handle 1156H. The surgeon may manipulate the handle 1156H to position the transfer guide 1156 at the surgical site. The guide body 1162 may be coupled to at least one transfer member 1154. The transfer member 1154 may be moveable relative to the guide body 1162 to set an orientation of the guide body 1162 relative to the patient anatomy.

Figure 48:
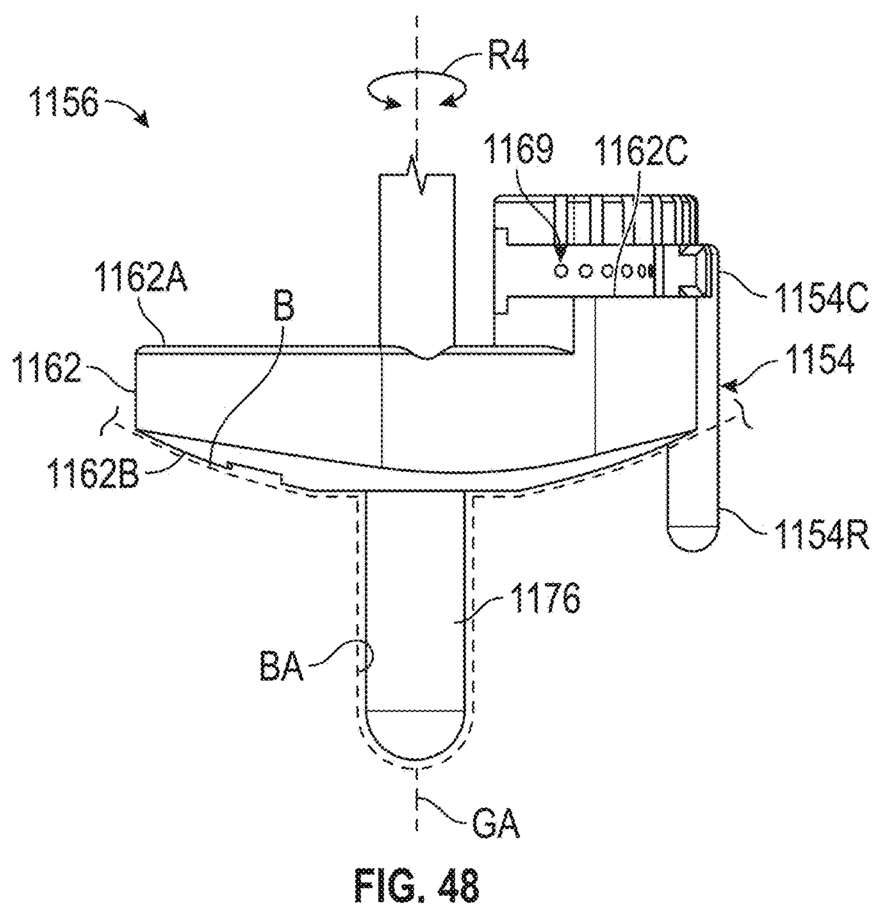
FIG. 48 illustrates a side view of the transfer guide of FIG. 46.
Figure 49:
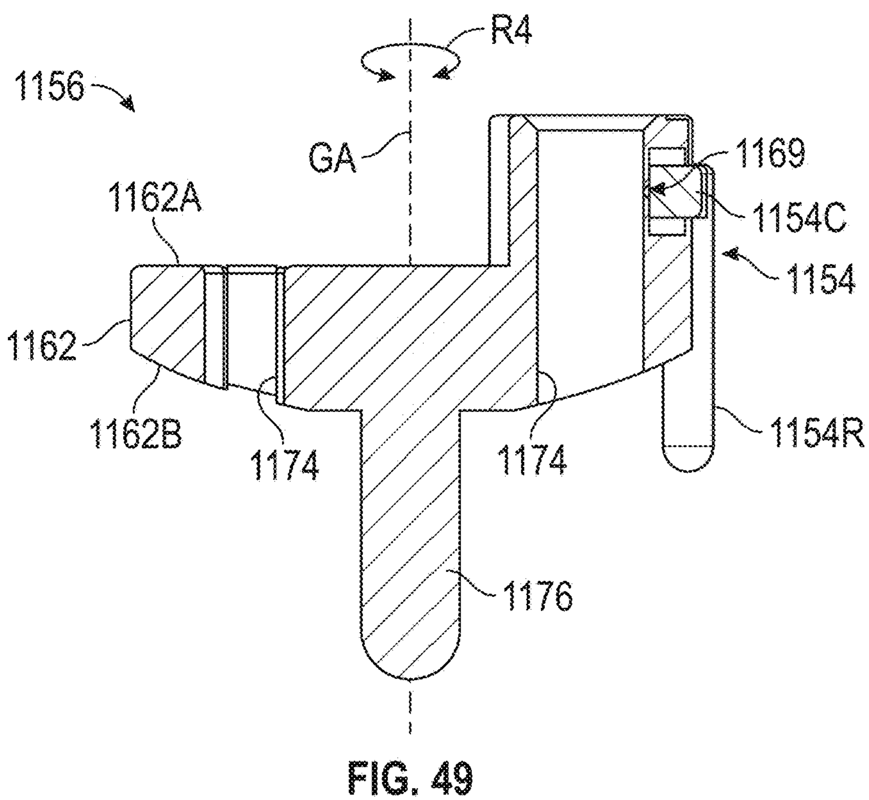
FIG. 49 illustrates a sectional view of the transfer guide of FIG. 48.

The guide body 1162 may extend along a guide axis GA between a first (e.g., front) face 1162A and a second (e.g., rear) face 1162B (see e.g., FIGS. 48-49). The rear face 1162B of the guide body 1162 may be dimensioned to contact an articular and/or non-articular surface of a bone, such as an articular surface of a glenoid (see, e.g., bone B shown in dashed lines in FIG. 48). The rear face 1162B may have symmetrical surface profile to facilitate rotation of the guide body 1162 about the guide axis GA.

Referring to FIG. 41, with continuing reference to FIG. 40, the guide body 1162 may include at least one or more guide apertures 1174. Each of the guide apertures 1174 may be dimensioned to receive one or more surgical devices. The surgical device may be insertable in bone or other tissue. The surgical devices may include any of the surgical devices disclosed herein such as a cutting, reaming, drilling, milling and/or punching instrument configured to alter the patient anatomy and/or a guide element insertable in bone. The guide element may include any of the guide elements disclosed herein. The guide element may be configured to situate another instrument or an implant relative to the patient anatomy. In implementations, the transfer guide 1156 may serve as a drill guide for positioning a drill configured to remove bone at one or more predetermined positions along the bone. The guide apertures 1174 may be configured to receive a drill bit or other instrument for removing a portion of bone or other tissue from the surgical site. The guide apertures 1174 may be established at various positions along the guide body 1162. Each of the apertures 1174 may have various geometries, such as a generally elliptical cross-sectional geometry. Each of the apertures 1174 may be established along the guide body 1162 based on a geometry of one or more features of a respective implant, such as an implant associated one or more of the implant models 32 (FIG. 2). The features may include various protrusions at least partially insertable in bone, such as a keel, post or stem (see, e.g., FIG. 35A).

The transfer guide 1156 may include at least one transfer member 1154. In implementations, the transfer guide 1156 may include more than one transfer member 1154. The transfer member 1154 may be configured to set a position of the guide body 1162 relative to the surgical site. The transfer member 1154 may incorporate any of the features of the transfer members disclosed herein.

The transfer member 1154 may include a carrier 1154C and an outrigger 1154R. The outrigger 1154R may extend distally from the carrier 1154C a distance past the rear face 1162B relative to the guide axis GA (see, e.g., FIGS. 48-49). The carrier 1154C may be movable along a periphery of the guide body 1162 to set a position of the outrigger 1154R relative to the guide axis GA. The outrigger 1154R may be configured to contact bone or other tissue to set an orientation of the guide body 1162 relative to the patient anatomy. The outrigger 1154R may be configured to have various lengths and/or diameters to engage the patient anatomy.

Figure 44:
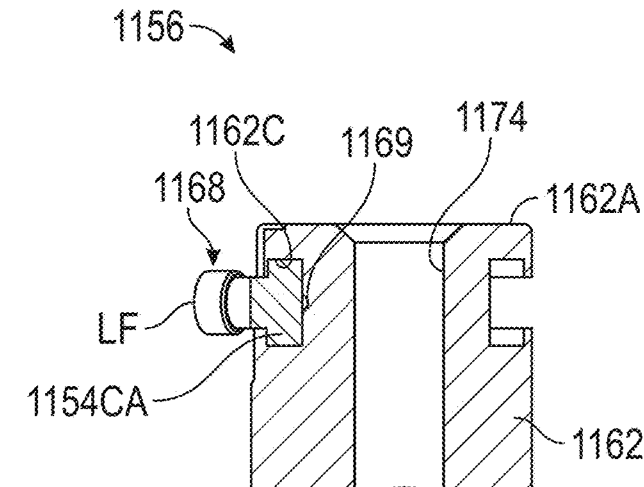
FIG. 44 illustrates a sectional view of the transfer guide of FIG. 41.

Various techniques may be utilized to secure the transfer member 1154 to the guide body 1162. The guide body 1162 may include an arcuate channel 1162C. The channel 1162C may extend along a periphery of the guide body 1162 (see also FIG. 42). The carrier 1154C may have a substantially arcuate portion 1154CA (see also FIG. 43). The channel 1162C may be dimensioned to at least partially receive the arcuate portion 1154CA of the carrier 1154C. In the implementation of FIG. 44, a cross section of the arcuate portion 1154CA may have a generally T-shaped geometry. A cross section of the channel 1162C may be dimensioned to substantially conform to a geometry of the arcuate portion 1154CA of the carrier 1154C to capture the arcuate portion 1154CA of the carrier 1154C in the channel 1162C. The arcuate channel 1162C may have a substantially T-shaped geometry that may extend along an arc path about a periphery of the guide body 1162. The carrier 1154C may be movable along the arcuate channel 1162C to position the outrigger 1154R relative to the guide axis GA.

The transfer guide 1156 may include an alignment mechanism 1164 for indicating a position of the transfer member 1154. The alignment mechanism 1164 may be established according to any of the techniques disclosed herein. The alignment mechanism 1164 may configured to indicate a circumferential position of the outrigger 1154R relative to the guide axis GA. The alignment mechanism 1164 may include a ruler 1164R and an indicator 1164I adjacent the ruler 1164R.

Referring to FIGS. 44-47, with continuing reference to FIGS. 41-43, the transfer guide 1156 may include at least one lock mechanism 1168. The lock mechanism 1168 may be configured to limit movement of the carrier 1154C along the arcuate channel 1162C of the guide body 1162. The lock mechanism 1168 may incorporate any of the features disclosed herein. In implementations, the lock mechanism 1168 may include a lock fastener (e.g., set screw) LF. The lock fastener LF may be dimensioned to engage a wall of the guide body 1162 along the arcuate channel 1162C to limit movement of the carrier 1154C along the arcuate channel 1162C of the guide body 1162. The lock fastener LF may be dimensioned to engage one or more depressions 1169 along a face of the arcuate channel 1162C (see, e.g., FIGS. 44 and 47-48).

Referring to FIGS. 48-49, with continuing reference to FIGS. 40-41, the guide body 1162 may include a guide element (e.g., anchor or alignment member) 1176. The guide element 1176 may be configured to limit movement between the transfer guide 1156 and the patient anatomy. The guide element 1176 may include any of the guide elements disclosed herein and may be insertable in bone. The guide element 1176 may be configured to secure the guide body 1162 to bone or otherwise limit relative movement. In the implementation of FIGS. 48-49, the guide element 1176 may be established by an anchor member such as a protrusion dimensioned to extend outwardly from the rear face 1162B of the guide body 1162. The guide element 1176 may be integrally formed with, or may be fixedly secured to, the guide body 1162. In implementations, the guide element 1176 may extend outwardly from the rear face 1162B of the guide body 1162 along the guide axis GA. The guide element 1176 may be insertable in an aperture BA formed in bone B (shown in dashed lines in FIG. 48). The guide body 1162 may be rotatable in a fourth rotational direction R4 about the guide axis GA of the guide element 1176 to set an orientation of the guide apertures 1174 relative to the patient anatomy. In implementations, one or more of the guide apertures 1174 may be spaced apart from the guide axis GA and/or an axis of the guide element 1176 (see, e.g., FIG. 49). In other implementations, the guide element 1176 may be omitted.

Figure 50:
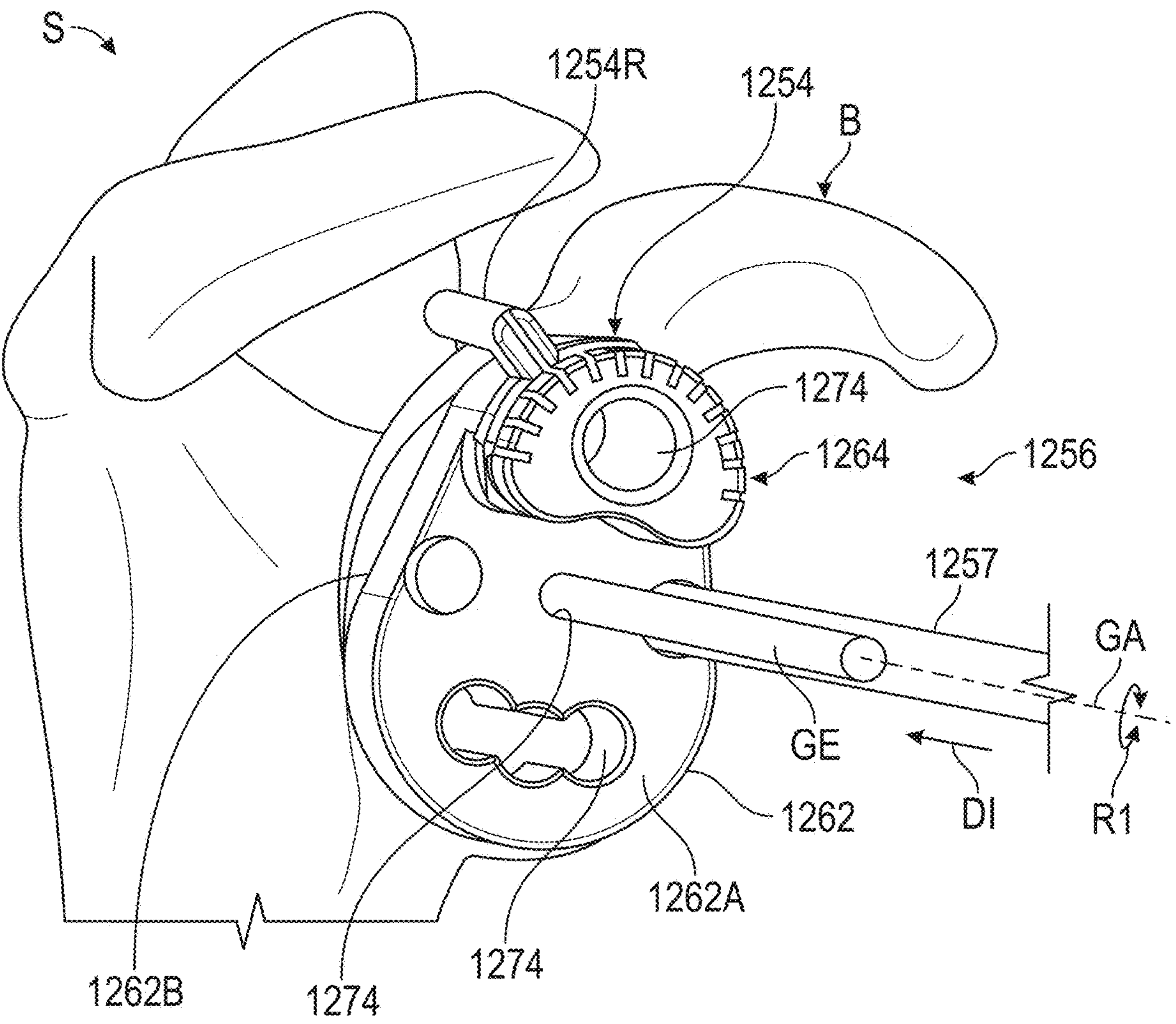
FIG. 50 illustrates a perspective view of a transfer guide according to another implementation.

FIG. 50 illustrates a transfer guide 1256 for an orthopedic procedure according to another implementation. The transfer guide 1256 may include a guide body 1262 having one or more guide apertures 1274. One of the guide apertures 1274 may be established along a guide axis GA of the guide body 1262. The guide aperture 1274 may be dimensioned to receive a guide element GE, including any of the guide elements disclosed herein such as a guide pin. The guide element GE may be insertable in bone B. The guide element GE may extend through an anchor member of the implant and/or may serve as an anchor member to limit movement between the transfer guide 1256 and the bone B. The guide body 1262 may be rotatable in a first rotational direction R1 about the guide element GE to set an orientation of the guide apertures 1274 relative to the guide axis GA.

Figure 51:
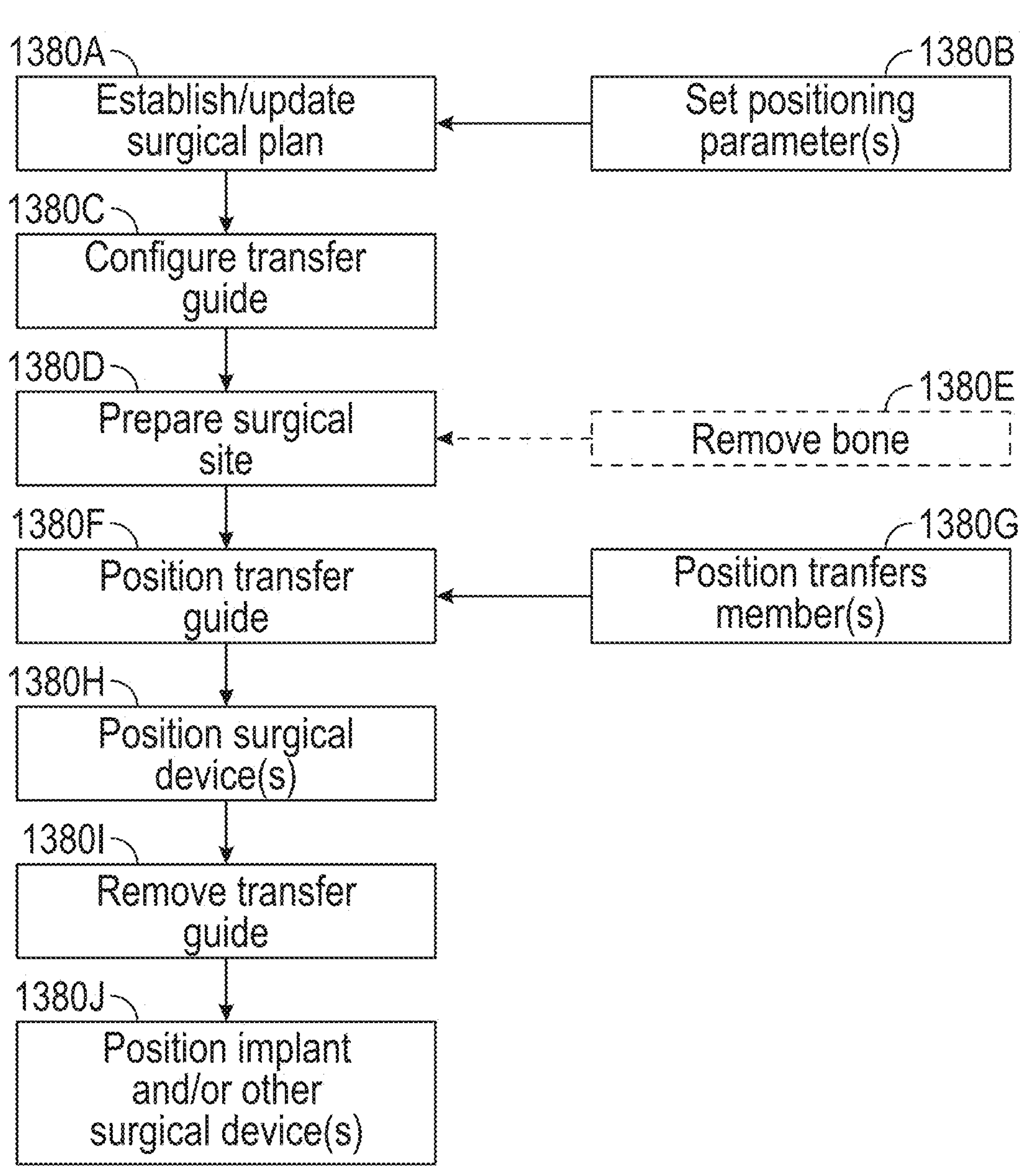
FIG. 51 illustrates a method of planning and implementing an orthopaedic procedure according to another implementation.

FIG. 51 illustrates an exemplary method of planning and implementing an orthopaedic procedure in a flowchart 1380. The method 1380 may be utilized pre-operatively, intra-operatively and/or post-operatively to create, edit, execute and/or review a respective surgical plan, including installing one or more orthopaedic implants. The method 1380 may be utilized to perform any of the surgical procedures disclosed herein. The method 1380 may be utilized to perform an arthroplasty for restoring functionality to shoulders and other joints, including any of the joints disclosed herein. The method 1380 may be utilized with any of the planning systems, assemblies, implants, transfer members, transfer guides and instruments and devices disclosed herein, including transfer guides 1156 and 1256. Method 1380 may incorporate any of the steps of method 1072. Fewer or additional steps than are recited below could be performed within the scope of this disclosure, and the recited order of steps is not intended to limit this disclosure. The planning system 20 and any of associated modules may be configured to execute each of the steps of the method 1380. Reference is made to the planning system 20 and graphical user interface 43 of FIGS. 2 and 3A-3B and the transfer guide 1156 of FIGS. 40-49 and the transfer guide 1256 of FIG. 50 for illustrative purposes.

At step 1380A, a surgical plan 33 may be established and/or updated for a patient. The surgical plan 33 may be established according to any of the techniques disclosed herein, including any of features of steps 1072A to 1072J of the method 1072 of FIG. 32. Step 1380A may include setting or otherwise establishing one or more positioning parameters relating to a transfer model 48 and associated transfer member(s) at step 1380B. A transfer model 48 may be associated with the transfer guide 1156 and/or transfer guide 1256. The positioning parameters may include any of the parameters disclosed herein, including one or more settings or dimensions associated with the transfer model 48. Step 1380B may incorporate any of the features of step 1072G of FIG. 32.

At step 1380C, the surgeon or clinical assistant may configure the transfer guide 1156. Step 1380C may incorporate any of the features of step 1072K of FIG. 32. Step 1380C may include configuring the transfer guide 1156 according to one or more settings or parameters specified in the surgical plan 33.

Configuring the transfer guide 1156 at step 1380C may include rotating or otherwise moving the carrier 1154C about a periphery of the guide body 1162 to set an orientation of the outrigger 1154R relative to the guide axis GA. Step 1380C may include moving the transfer member 1154 between a first position and a second position relative to the guide body 1162 based on at least one parameter of a preoperative plan, such as a surgical plan 33.

Figure 45:
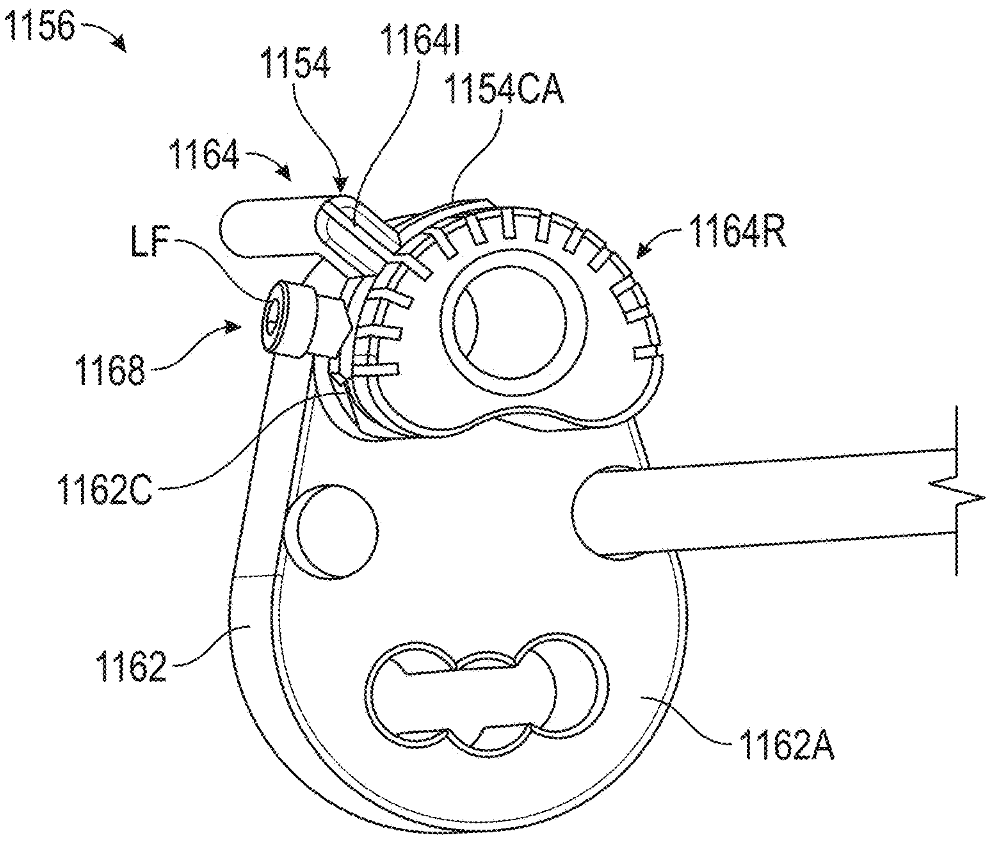
FIG. 45 illustrates a perspective view of the transfer guide of FIG. 41 including the transfer member in a second position.

In the implementation of FIGS. 41 and 45, the guide body 1162 may include an arcuate channel 1162C along the periphery of the guide body 1162. Configuring the transfer guide 1156 at step 1380C may include moving the carrier 1154C along the arcuate channel 1162C to set the position of the outrigger 1154R relative to the guide axis GA (see also FIG. 55).

Figure 46:
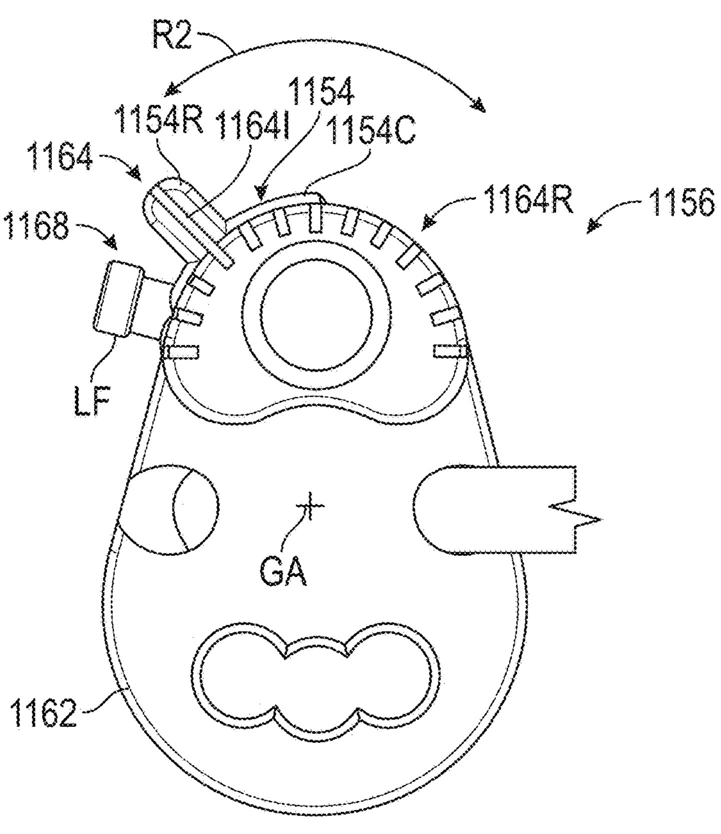
FIG. 46 illustrates a plan view of the transfer guide of FIG. 45.
Figure 47:
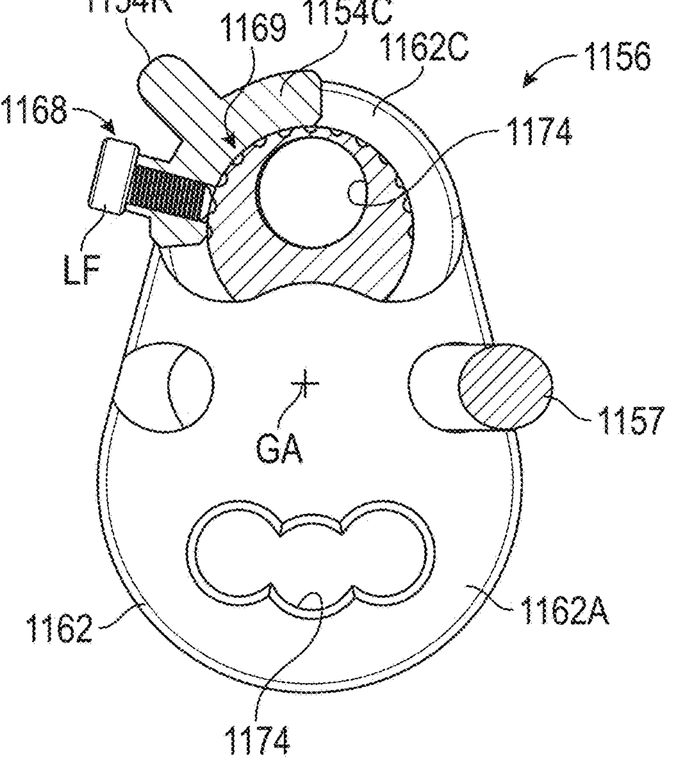
FIG. 47 illustrates a sectional view of the transfer guide of FIG. 46.

Various techniques may be utilized to establish the position of the transfer member 1154. The orientation of the outrigger 1154R may be set according to a position of the indicator 1164I relative to the ruler 1164R of the alignment mechanism 1164. In the implementation of FIG. 46, the surgeon or clinical assistant may move the indicator 164I in a second rotational direction R2 relative to the guide axis GA to set a position of the indicator 1164I relative to the ruler 1164R. The indicator 1164I may be aligned with a selected position or value on the ruler 1164R. The selected position along the ruler 1164R may be associated with one or more settings or parameters determined for the respective transfer model 48 at step 1380B or otherwise specified in a respective surgical plan 33 at step 1380A.

Figures 52, 53, 54, 55:
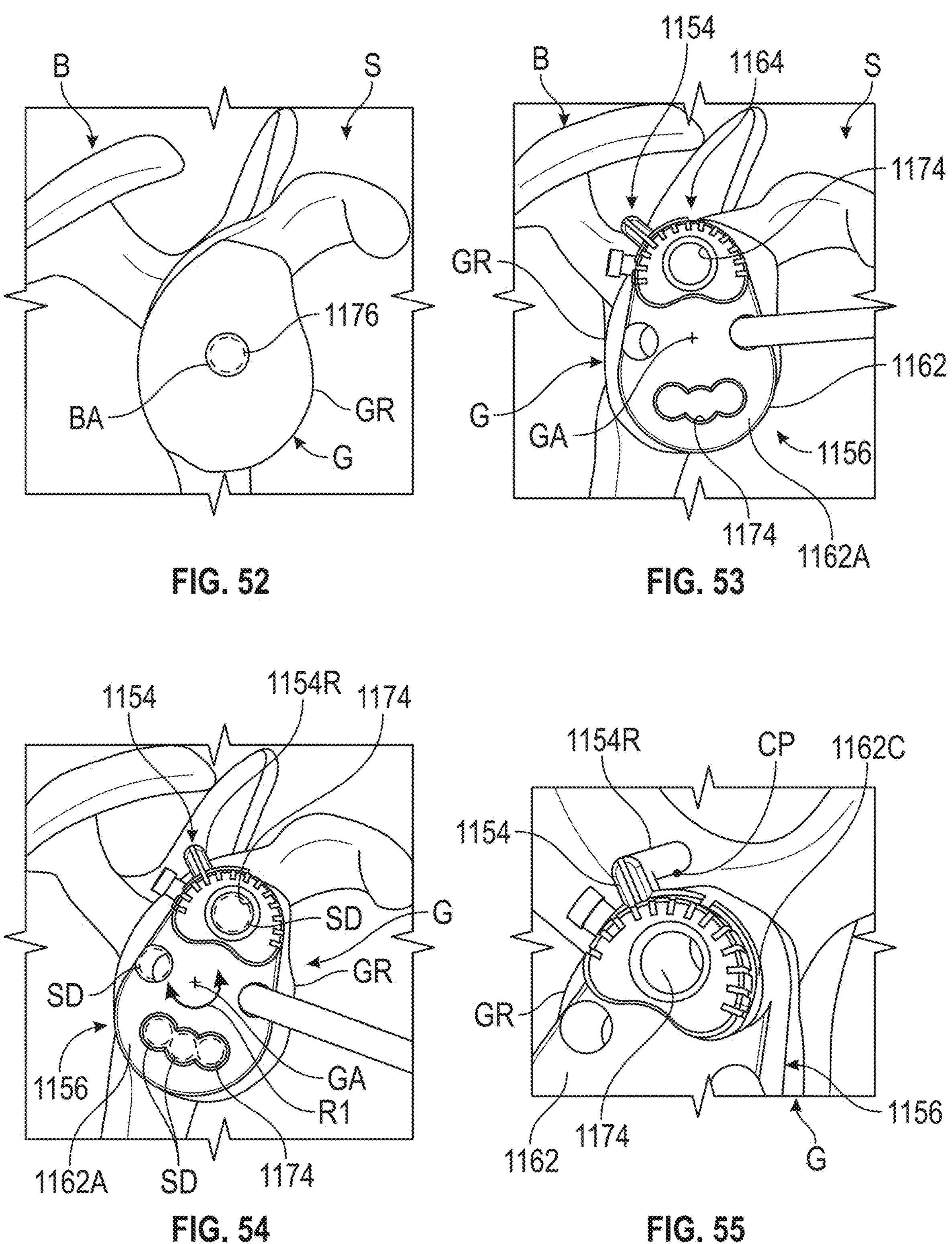
FIG. 52 illustrates a surgical site including removal of bone.
FIG. 53 illustrates a plan view of the transfer guide of FIG. 46 at a first position relative to the bone of FIG. 52.
FIG. 54 illustrates a plan view of the transfer guide at a second position relative to the bone of FIG. 53.
FIG. 55 illustrates a perspective view of portions of the transfer guide of FIG. 54.

Referring to FIG. 52, with continuing reference to FIG. 51, implementing the surgical plan 33 may include preparing the surgical site S at step 1380D. Step 1380D may incorporate any of the features of step 1072M. Step 1380D may include removing a portion of the bone B at step 1380E. Various techniques may be utilized to remove the portion of bone B, such as a cutting, reaming, drilling, milling and/or punching operation. Step 1380D may include forming an aperture BA along the bone B. The bone B may be a portion of a glenoid G. The aperture BA may be established along an articular and/or non-articular surface of the bone B, such as along an articular surface of a glenoid G.

Referring to FIG. 53, with continuing reference to FIGS. 51-52, the surgeon may position the transfer guide 1156 at step 1380F. The transfer guide 1156 may include a guide body 1162. The guide body 1162 may extend along a guide axis GA between a first (e.g., front) face 1162A and a second (e.g., rear) face 1162B (see, e.g., FIGS. 48-49). The guide body 1162 may include at least one or more apertures 1174.

Step 1380F may include positioning the guide body 1162 of the transfer guide 1156 in abutment with an articular and/or non-articular surface of the bone B, such as along the articular surface of the glenoid G. Step 1380F may include at least partially inserting the guide element 1176 in the aperture BA (shown in dashed lines in FIG. 52).

In the implementation of FIG. 50, step 1380F may include positioning the surgical guide 1376 at the surgical site S. Step 1380F may include inserting or otherwise positioning a guide element GE at a selected position along the bone B. The selected position may be specified in the surgical plan 33. The guide body 1262 may include one or more (e.g., guide) apertures 1274. Step 1380F may include positioning the guide element GE in the selected aperture 1274 and into the bone B. Step 1380F may include moving the guide body 1262 in the first direction D1 along the guide element GE such that the rear face 1262B of the guide body 1262 may abut a surface of the bone B.

Referring to FIGS. 54-55, with continuing reference to FIGS. 51 and 53, step 1380F may include positioning the transfer guide 1156 relative to the bone B based on a position of the transfer member(s) 1154 relative to the guide axis GA. Step 1380F may include rotating the transfer guide 1156 in a first rotational direction R1 about the guide axis GA and/or guide element GE (FIG. 50) such that the outrigger 1154R may establish contact with the bone B at a respective contact point CP (FIG. 55). In the implementation of FIG. 50, step 1380F may include rotating the guide body 1262 in the first rotational direction R1 about the guide element GE to establish an orientation of the transfer guide 1256 relative to the bone B.

At step 1380H, the surgeon may position one or more surgical devices SD through one or more selected apertures 1174 (shown in dashed lines in FIG. 54). The surgical device SD may be a tool or instrument utilized to remove a portion of the bone B. Step 1380H may include causing the surgical device SD to remove a portion of the bone B subsequent to positioning the surgical device SD in the respective aperture 1174. The surgical devices SD may include any of the instruments and other surgical devices disclosed herein. The surgeon may remove the portion(s) of bone B based on one or more parameters specified in the surgical plan 33, such as one or more dimensions and/or a predetermined position and/or orientation of an implant associated with the surgical plan 33. The transfer guide 1156 may be removed from the surgical site S at step 1380I. In the implementation of FIG. 50, step 1380I may include removing the guide element GE from the bone B.

The method 1380 may include one or more subsequent steps, including any of the steps 1072T to 1072V of FIG. 32. In implementations, an implant and/or other surgical device may be positioned at the surgical site S at step 1380J. The implant may include one or more features at least partially insertable in regions of the removed portion of the bone B, such as a stem or keel. The implant may be secured to the bone B utilizing any of the techniques disclosed herein.

The novel planning systems, assemblies and methods of this disclosure can be incorporated into a practical application by providing improved positioning of implants and other surgical devices relative to patient anatomy. The disclosed techniques may reduce a complexity in preparing for and performing a surgical procedure according to a predetermined surgical plan, including implementing the surgical plan by positioning implants and other surgical devices in a manner that may closely corresponds to one or more parameters specified in the surgical plan. The disclosed techniques may more accurately orient associated implants and other surgical devices, which may lead to improved implant seating and fixation, fastener to bone fixation and patient healing. The disclosed transfer guides may be reusable, which may reduce cost and training associated with implementing different surgical plans.

Although the different non-limiting implementations are illustrated as having specific components or steps, the implementations of this disclosure are not limited to those particular combinations. It is possible to use some of the components or features from any of the non-limiting implementations in combination with features or components from any of the other non-limiting implementations.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A transfer guide for an orthopaedic procedure comprising:

a guide body including an interface portion configured to be securable to a surgical device, wherein the surgical device includes an implant securable to bone;

a flange extending radially from the guide body relative to a guide axis of the guide body; and at least one transfer member coupled to the guide body, the at least one transfer member including a carrier and an outrigger extending from the carrier, the carrier rotatable about a periphery of the guide body to set a circumferential position of the outrigger relative to the guide axis, the outrigger configured to contact tissue to set an orientation of the guide body, and the outrigger is configured to set an orientation of the surgical device securable to the interface portion;

wherein one of the flange and the carrier includes an indicator, and another one of the flange and the carrier includes a ruler;

wherein the indicator is moveable relative to the ruler to indicate the circumferential position of the outrigger relative to the guide axis of the guide body; and wherein a first portion of the carrier extends from the guide body radially beyond the flange relative to the guide axis, and the outrigger extends distally from the first portion of the carrier at a position radially outward of a periphery of the flange relative to the guide axis.

2. The transfer guide as recited in claim 1, wherein:

the guide body includes an elongated guide shaft extending along the guide axis between a proximal end and a distal end; and the interface portion is established adjacent the distal end of the guide shaft.

3. The transfer guide as recited in claim 2, further comprising:

the implant; and wherein the interface portion is adapted to limit relative rotation between the guide shaft and the implant with respect to the guide axis.

4. The transfer guide as recited in claim 3, wherein:

the interface portion includes an inserter adjacent to the distal end of the guide shaft;

the inserter includes a plurality of protrusions distributed about the guide axis; and the protrusions are adapted to mate with an array of insertion apertures of the implant to limit relative rotation between the guide shaft and the implant with respect to the guide axis.

5. The transfer guide as recited in claim 3, wherein:

the transfer guide and the implant are rotatable together as a unit in a first rotational direction about an implant axis of the implant.

6. The transfer guide as recited in claim 3, wherein:

the indicator and the ruler cooperate to establish a protractor;

the ruler includes indicia associated with circumferential positions of the outrigger relative to the guide axis; and the indicator is moveable in a second rotational direction relative to the ruler in response to rotation of the carrier about the periphery of the guide body to indicate the circumferential position of the outrigger relative to the guide axis of the guide body.

7. The transfer guide as recited in claim 1, wherein:

the carrier includes at least one aperture; and the outrigger is slidably received in the at least one aperture to set a position of the outrigger relative to the guide body.

8. The transfer guide as recited in claim 7, wherein:

the at least one aperture includes a plurality of apertures distributed in a radial direction and/or circumferential direction relative to the guide axis of the guide body; and the outrigger is insertable in a selectable one of the plurality of apertures to set a position of the outrigger relative to the guide axis.

9. The transfer guide as recited in claim 8, wherein:

the at least one transfer member includes a set of transfer members releasably securable to the guide body; and the set of transfer members are dimensioned such that a distribution of the plurality of apertures differs for each transfer member of the set of transfer members.

10. The transfer guide as recited in claim 1, wherein:

the guide body is dimensioned to contact an articular surface and/or a non-articular surface of a bone.

11. A kit for an orthopaedic procedure comprising:

at least one implant including a baseplate, the baseplate including a main body and an anchor member extending outwardly from the main body, the anchor member securable to bone; and the transfer guide according to claim 1, wherein:

the interface portion is securable to the main body of the baseplate; and wherein the outrigger extends from the carrier such that the outrigger is spaced apart from a periphery of the at least one implant.

12. The kit as recited in claim 11, wherein the baseplate includes a plurality of peripheral apertures distributed about an axis of the main body, and the outrigger is configured to set a position of the peripheral apertures in response to contact with tissue.

13. The kit as recited in claim 11, wherein the at least one implant includes an articulation member securable to the baseplate, and the articulation member includes an articulation surface configured to engage an articular surface of an opposed bone or implant.

14. The kit as recited in claim 11, wherein:

the at least one transfer member includes a set of transfer members releasably securable to the guide body, and the carrier of each transfer member of the set of transfer members includes a plurality of apertures;

the outrigger is insertable in a selectable one of the plurality of apertures to set a position of the outrigger relative to the guide axis of the guide body; and the set of transfer members are dimensioned such that a distribution of the plurality of apertures differs for each transfer member of the set of transfer members.

15. A method of performing an orthopaedic procedure comprising:

providing the transfer guide as recited in claim 1;

configuring the transfer guide, wherein the guide body extends along the guide axis, and the configuring step includes moving the carrier relative to the periphery of the guide body to set the orientation of the outrigger relative to the guide axis; and positioning the transfer guide, including establishing contact between the outrigger and tissue to set the orientation of the transfer guide relative to a bone.

16. The method as recited in claim 15, wherein the configuring step includes moving the transfer member between a first position and a second position relative to the guide body based on at least one parameter of a preoperative plan.

17. The method as recited in claim 15, further comprising:

coupling the transfer guide and an implant to each other; and positioning the implant in contact with the bone, including orienting the implant relative to the bone based on the orientation of the transfer guide.

18. The method as recited in claim 15, wherein the bone is a portion of a glenoid.

* * * * *